(12) United States Patent
Skubatch

(10) Patent No.: US 7,858,586 B2
(45) Date of Patent: *Dec. 28, 2010

(54) METHOD OF TREATING CONDITION IN ANIMAL

(75) Inventor: Hanna Skubatch, Seattle, WA (US)

(73) Assignee: NeoPro Labs, LLC, Seattle, WA (US)

(*) Notice: Subject to any disclaimer, the term of this patent is extended or adjusted under 35 U.S.C. 154(b) by 554 days.

This patent is subject to a terminal disclaimer.

(21) Appl. No.: 11/681,649

(22) Filed: Mar. 2, 2007

(65) Prior Publication Data

US 2007/0185029 A1 Aug. 9, 2007

Related U.S. Application Data

(62) Division of application No. 11/287,157, filed on Nov. 25, 2005.

(60) Provisional application No. 60/630,880, filed on Nov. 24, 2004, provisional application No. 60/652,287, filed on Feb. 10, 2005, provisional application No. 60/658,859, filed on Mar. 4, 2005.

(51) Int. Cl.
A61K 38/07 (2006.01)
(52) U.S. Cl. .................................. 514/18.4
(58) Field of Classification Search ............... None
See application file for complete search history.

(56) References Cited

U.S. PATENT DOCUMENTS

| | | | |
|---|---|---|---|
| 5,189,064 | A | 2/1993 | Blum et al. |
| 5,328,836 | A | 7/1994 | Shima et al. |
| 5,492,894 | A | 2/1996 | Bascom et al. |
| 5,506,202 | A | 4/1996 | Vertesy et al. |
| 5,705,621 | A | 1/1998 | Ravikumar |
| 5,760,044 | A | 6/1998 | Archer |
| 5,854,226 | A | 12/1998 | Penkler et al. |
| 6,419,931 | B1 | 7/2002 | Vitiello et al. |
| 6,689,363 | B1 | 2/2004 | Sette et al. |
| 6,794,144 | B1 | 9/2004 | Saksela et al. |
| 6,849,714 | B1 | 2/2005 | Bridon et al. |
| 7,244,599 | B2 | 7/2007 | Tanner et al. |
| 7,557,088 | B2 | 7/2009 | Skubatch |
| 2004/0254343 | A1 | 12/2004 | Miyakaki et al. |
| 2006/0154863 | A1 | 7/2006 | Skubatch |
| 2007/0254811 | A1 | 11/2007 | Skubatch |
| 2007/0259818 | A1 | 11/2007 | Skubatch |
| 2009/0069237 | A1 | 3/2009 | Skubatch |
| 2009/0170784 | A1 | 7/2009 | Skubatch |
| 2010/0137227 | A1 | 6/2010 | Skubatch |

FOREIGN PATENT DOCUMENTS

| | | |
|---|---|---|
| DE | 4433564 A1 | 4/1996 |
| EP | 0514268 A1 | 11/1992 |
| EP | 0966975 A2 | 12/1999 |
| EP | 0966975 A3 | 4/2002 |
| EP | 0966975 B1 | 9/2005 |
| JP | 6-107683 A | 4/1994 |
| WO | WO 97/44447 A2 | 11/1997 |
| WO | WO 97/44447 A3 | 11/1997 |
| WO | WO 00/54805 A1 | 9/2000 |
| WO | WO 00/69900 A2 | 11/2000 |
| WO | WO 00/69900 A3 | 11/2000 |
| WO | WO 02/19986 A1 | 3/2002 |
| WO | WO 02/060432 A1 | 8/2002 |
| WO | WO 02/066625 A1 | 8/2002 |
| WO | WO 03/006654 A2 | 1/2003 |
| WO | WO 03/006654 A3 | 10/2003 |
| WO | WO 2004/054614 A1 | 7/2004 |
| WO | WO 2004/058804 A1 | 7/2004 |
| WO | WO 2004/098644 A1 | 11/2004 |
| WO | WO 2004/099135 A2 | 11/2004 |
| WO | WO 2004/099135 A3 | 11/2004 |
| WO | WO 2004/101797 A1 | 11/2004 |
| WO | WO 2006/000034 A1 | 1/2006 |
| WO | WO 2006/006172 A2 | 1/2006 |
| WO | WO 2006/006172 A3 | 5/2006 |
| WO | WO 2006/045313 A2 | 5/2006 |
| WO | WO 2006/045314 A2 | 5/2006 |
| WO | WO 2006/045314 A3 | 5/2006 |
| WO | WO 2006/045319 A2 | 5/2006 |
| WO | WO 2006/068768 A2 | 6/2006 |
| WO | WO 2006/068768 A3 | 6/2006 |
| WO | WO 2006/045313 A3 | 8/2006 |
| WO | WO 2006/045319 A3 | 9/2006 |

OTHER PUBLICATIONS

H. Unlugenc et al. Br. J. Anaest. (2003) 91(2), pp. 209-213.*
J. Reimer-Kent. Am. J. Crit. Care. (2003) 12(2), pp. 136-143.*
U.J. Moore et al. Br. J. Clin. Pharmacol. (1994) 37(3), pp. 227-230.*
E.A. Kiyatkin and R.A. Wise. J. Neurosci. (2002) 22(3), pp. 1072-1080.*
K. Lufty et al. Psychopharm. (2002) 164, pp. 168-176.*
J. Gimbel and H. Ahdieh. Anesth. Analg. (2004) 99, pp. 1472-1477.*
Chen, et al. Epsin is an EH-domain-binding protein implicated in clathrin-mediated endocytosis. Nature. 1998; 394:793-7.
Dinkova-Kostova, A., et al. (+)-Pinoresinol/(+)-Lariciresinol Reductase from Forsythia Intermedia. J. Biol. Chem. 1996; 271(46):29473-82.

(Continued)

Primary Examiner—Andrew D Kosar
(74) Attorney, Agent, or Firm—Wilson Sonsini Goodrich & Rosati

(57) ABSTRACT

The invention relates to compositions comprising of SEQ NO: 1-244, 248-249, and any homologs, analogs, and fragments thereof. Such compositions can be used to treat, prevent, and modulate pain, inflammation, and metabolic processes in various organisms including plants and animals. Such compositions can be formulated with an acceptable pharmaceutical excipient for administration to a human or a plant. The compositions can be administered topically or for systemic use.

10 Claims, 6 Drawing Sheets

OTHER PUBLICATIONS

Fujita, et al. Recombinant pinoresinol-lariciresinol reductases from western red cedar (*Thuja plicata*) catalyze opposite enantiospecific conversions. J. Biol. Chem. 1999; 274(2):618-27.

Gang, D. et al. Evolution of Plant Defense Mechanism. J. Biol. Chem. 1999; 274(11):7516-7527.

Horikawa, et al. Isolation and structural organization of the human preproenkephalin B gene. Nature. 1983; 306:611-4.

Latvala-Kilby, et al. The complete nucleotide sequence of RNA2 of blackcurrant reversion nepovirus. Virus Research. 1999; 65:87-92.

Lers, et al. The expression of a grapefruit gene encoding an isoflavone reductase-like protein is induced in response to UV irradiation. Plant Mol. Biol. 1998; 36:847-56.

Messer, W. S. Vasopressin and Oxytocin. This page was last updated on Monday, Apr. 3, 2000. Available at http://www.neurosci.pharm.utoledo.edu/MBC3320/vasopressin.htm. Accessed Dec. 19, 2006.

NCBI Database Accession No. AAC50454, Feb. 28, 2006.

NCBI Database Accession No. AAD09329, Feb. 28, 2006.

NCBI Database Accession No. NP_001017915, Feb. 28, 2006.

NCBI Database Accession No. NP_005532, Feb. 28, 2006.

Shorter, et al. GRASP55, a second mammalian GRASP protein involved in the stacking of *Golgi cisternae* in a cell-free system. EMBO J. 1999; 18(18):4949-60.

Bertoletti, et al. Definition of minimal optimal cytotoxic T-cell epitope within the hepatitis B virus nucleocapsid protein. J Virol. 1993;67(4):2376-80.

Hawks, et al. Opioid Peptides. Drug Abuse Research Monograph. # 70, 1986.

Hruby, et al. Design of novel peptide ligands which have opioid agonist activity and CCK antagonist activity for the treatment of pain. 2003; 73:699-704.

Hruby, et al. Conformation-activity relationships of opioid peptides with selective activities at opioid receptors. Biopolymers. 1999; 51(6):391-410.

McPherson. A comparison of salts for the crystallization of macromolecules. Protein Sci. 2001; 10(2):418-22.

Pikal, et al. The stability of insulin in crystalline and amorphous solids: observation of greater stability for the amorphous form. Pharm Res. 1997; 14(10):1379-87.

Shenoy, et al. Stability of crystalline proteins. Biotechnol Bioeng. 2001; 73(5):358-69.

International search report dated Oct. 29, 2008 for PCT Application No. US2008/064171.

International search report dated Nov. 13, 2007 for PCT Application No. US2005/42682.

International search report dated Feb. 10, 2009 for PCT Application No. US2008/70534.

International search report dated Sep. 29, 2008 for PCT Application No. US2007/65404.

Keinath, et al. Evaluation of biological and chemical seed treatments to improve stand of snap bean across the southern United States. Crop Protection. 2000; 19(7):501-509.

Larkindale, et al. Protection against Heat Stress-Induced Oxidative Damage in Arabidopsis Involves Calcium, Abscisic Acid, Ethylene, and Salicylic Acid. Plant Physiol, Feb. 2002, vol. 128, pp. 682-695.

Syamsuwida, et al. Time and method of floral initiation and effect of paclobutrazol on flower and fruit development in *Shorea stenoptera* (Dipterocarpaceae). Tree Physiol. Apr. 1997;17(4):211-9.

Weiss, et al. A tricyclic ring system replaces the variable regions of peptides presented by three alleles of human MHC class I molecules. Chem Biol. Jun. 1995;2(6):401-7.

Salzet, M. Neuroimmunology of opioids from invertebrates to human. Neuro Endocrinol Lett. Dec. 2001;22(6):467-74.

Catania, et al. Peptide modulation of fever and inflammation within the brain. Ann N Y Acad Sci. Sep. 29, 1998;856:62-8.

Emel'ianova, et al. Effect of dermorphin analogs on thermoregulation of rats under various thermal conditions. Biology Bulletin. 2002; 29(3):284-289. (Translated from Izv Akad Nauk Ser Biol. May-Jun. 2002;(3):348-54.).

European search report dated Jun. 7, 2010 for Application No. 5852156.8.

Kalliomaki, et al. Prolactin-releasing peptide affects pain, allodynia and autonomic reflexes through medullary mechanisms. Neuropharmacology. Mar. 2004;46(3):412-24.

Le Guen, et al. Pain management by a new series of dual inhibitors of enkephalin degrading enzymes: long lasting antinociceptive properties and potentiation by CCK2 antagonist or methadone. Pain. Jul. 2003;104(1-2):139-48.

Tatro, et al. The central melanocortin system and fever. Ann NY Acad Sci. Jun. 2003;994:246-57.

Wollemann, et al. Non-opioid actions of opioid peptides. Life Sci. Jun. 4, 2004;75(3):257-70.

* cited by examiner

* Significantly different from saline group.

METHOD OF TREATING CONDITION IN ANIMAL

CROSS-REFERENCE TO RELATED APPLICATIONS

This application is a Divisional of U.S. application Ser. No. 11/287,157 filed Nov. 25, 2005, which claims priority to U.S. Provisional Application Nos. 60/630,880, filed Nov. 24, 2004, 60/652,287, filed Feb. 10, 2005, and 60/658,859 filed Mar. 4, 2005, which are hereby incorporated by reference for all purposes.

BACKGROUND

Pain is a condition that affects everyone at some point in his lifetime. The pain signaling pathway can be modulated by endogenous and synthetic opioid peptides and by small molecules. Pain is induced by multiple types of stimuli such as temperature and tissue damage suggesting that these pathways have at least one common component. Currently, the therapeutic choice in the management of severe acute and chronic pain is at the plasma membrane site, where the opioid peptides act as agonists for different opioid receptors.

As the world is experiencing an increase in life expectancy and population size, there is a significant need to identify new compositions and methods to treat and/or prevent different physiological conditions associated with pain, inflammation, thermoregulation, and other mitochondria-associated condition in both animals and plants.

INCORPORATION BY REFERENCE

All publications and patent applications mentioned in this specification are herein incorporated by reference to the same extent as if each individual publication or patent application was specifically and individually indicated to be incorporated by reference.

SUMMARY OF THE INVENTION

The invention herein involves compositions comprising, consisting essentially of, or consisting of a polypeptide of the invention or a homolog, analog, mimetic, salt, prodrug, metabolite, or fragment thereof. In some embodiments, a polypeptide comprises, consists essentially of, or consists of one or more amino acid sequences of SEQ ID NOs: 1-244, 248-249 or a reverse sequence of SEQ ID NOs: 1-244, 248-249. For example, in some embodiments, a composition comprises a polypeptide having amino acid sequence of SEQ ID NO: 1-14 or 50-244, 248-249, or SEQ ID NO: 1 or 2, or SEQ ID NO: 1. In some embodiments, a composition comprises a polypeptide having an amino acid sequence which is the reverse of SEQ ID NO: 1. The invention herein also contemplates homologs, analogs, mimetics, salts, prodrugs, metabolites, and fragments of the above polypeptides and compositions comprising the same.

The compositions herein can be used to modulate, prevent, or treat pain, inflammation, infections (e.g., bacterial fungi, viruses, etc.), and metabolic processes or conditions in an organism (plant or animal). Examples of metabolic conditions include, but are not limited to, pain, wound healing, inflammation, heat production, fever, homeothermy, breakdown of triglycerides, glycolysis, Krebs cycle, fermentation, photosynthesis, metabolic rate, biotic and abiotic stress, secretions, oxidative stress, stress, neoplastic growth, skin condition, cardiovascular conditions, neurological and neurodegenerative conditions, mental and behavioral disorders. Such processes or conditions can occur in a cell, group of cells, or an entire organism.

The compositions herein can be used for modulating, preventing, treating condition(s) in organisms. Such organisms can be animals and/or plants.

In some embodiments, the compositions herein (e.g., a composition comprising a polypeptide of SEQ ID NOs: 1-244, 248-249, or more preferably SEQ ID NO: 1 are used to modulate or treat pain, such as nociceptive (non-chronic) pain, neuropathic (chronic) pain, idiopathic pain, headaches, low back pain, cancer pain, arthritis pain, sprains, bone fractures, pain resulting from burns, pain associated with bumps, pain associated with bruises, inflammatory pain (e.g., from an infection or arthritic disorder), pain from obstructions, myofascial pain, pain from nerve trauma (e.g., dystrophy/causalgia), phantom limb pain, entrapment neuropathy (e.g., carpal tunnel syndrome), and peripheral neuropathy.

Preferably, a composition comprising SEQ ID NO: 1 or a salt, metabolite, or prodrug thereof is administered to an animal to treat pain. Such pain can be non-chronic pain, neuropathic pain, or idiopathic pain. It is further contemplated a compositions comprising a polypeptide described herein (e.g., SEQ ID NO: 1) is co-administered with one or more other pain relief medications. For example, a polypeptide described herein, such as SEQ ID NO: 1 can be administered simultaneously with, co-formulated with, or administered in the same therapy as a pain reliever selected from the group consisting of small molecules (e.g., non-narcotic and narcotic analgesics) and peptide opioids.

In some embodiments, the compositions herein (e.g., a composition comprising a polypeptide comprising, consisting essentially, or consisting of SEQ ID NOs: 1-244, 248-249, or more preferably SEQ ID NO: 1) are used to modulate or treat inflammatory conditions that may or may not cause pain. Such conditions may show one or more of the following symptoms: redness, heat, tenderness and swelling. Examples of such conditions include, but are not limited to, chronic inflammatory diseases, such as rheumatoid arthritis, inflammatory bowel disease, systemic lupus erythematosus, multiple sclerosis, and type I and II diabetes, asthma, and inflammatory diseases of the central nervous system such as multiple sclerosis, abscess, meningitis, encephalitis and vasculitis.

In some embodiments, the compositions herein (e.g., a composition comprising a polypeptide comprising, consisting essentially, or consisting of SEQ ID NOs: 1-244, 248-249, or more preferably SEQ ID NO: 1) are used to modulate or treat cardiovascular conditions. Examples of cardiovascular conditions associated with pain and/or inflammation include, but are not limited to, angina, arrhythmia, high blood pressure, stroke, congestive heart failure, atherosclerosis, peripheral artery diseases, high cholesterol levels, and heart attacks.

In some embodiments, the compositions herein (e.g., a composition comprising a polypeptide comprising, consisting essentially, or consisting of SEQ ID NOs: 1-244, 248-249, or more preferably SEQ ID NO: 1) are used to modulate or treat a neurological or neurodegenerative condition or a mental or behavioral disorder. Examples of neurological conditions associated with pain and/or inflammation include, but are not limited to, Alzheimer's disease, amnesia, Aicardi syndrome, amyotrophic lateral sclerosis (Lou Gehrig's disease), anencephaly, anxiety, aphasia, arachnoiditis, Arnold Chiari malformation, attention deficit syndrome, autism, Batten disease, Bell's Palsy, bipolar syndrome, brachial plexus injury, brain injury, brain tumors, childhood depress ion, Charcol-Marie tooth disease, depression, dystonia, dyslexia, encephalitis, epilepsy, essential tremor, Guillain-Barre syndrome, hydrocephalus, hyperhidrosis, Krabbes disease, learning disabilities, leukodystrophy, meningitis, Moebius syndrome, multiple sclerosis, muscular dystrophy, Parkinson's disease, peripheral neuropathy, obsessive compulsive disorder, postural orthostatic tachycardia syndrome, progressive supranuclear palsy, prosopagnosia, schizophrenia, shingles, Shy-Drager syndrome, spasmodic torticollis, spina bifida, spinal muscular atrophy, stiff man syndrome, synesthesia, syringomyelia, thoracic outlet syndrome, tourette syndrome, toxoplasmosis, and trigeminal neurolagia.

Examples of mental and behavioral disorders include, but are not limited to, anxiety disorder, panic disorder, obsessive-compulsive disorder, post-traumatic stress disorder, social phobia (or social anxiety disorder), specific phobias, and generalized anxiety disorder. Any of the above conditions can also be accompanied by or manifested by other conditions such as depression, drug abuse, or alcoholism.

In some embodiments, the compositions herein are used to treat fever that occurs with many different conditions such as inflammation and infectious diseases.

In some embodiments, the compositions herein are used to modulate or treat neoplastic growth. Examples of neoplastic growth include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell leukemia, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforme, leukemias, lymphomas, malignant melanomas, epidermoid carcinomas, and other carcinomas and sarcomas.

Thus, in some embodiments, a composition herein (e.g., SEQ ID NO: 1) can be administered simultaneously with, co-formulated with, or administered in the same therapy as an anti-neoplastic agent.

In some embodiments, the compositions herein are used to modulate and treat abnormal temperature associated with non-rapid eye movement (NREM) during sleep, thermotaxis of human spermatozoa toward fertilization site (isthmic-ampullary junction) at ovulation, and hot flashes in postmenopausal women.

In some embodiments, the compositions herein are used to treat or prevent plants/crops from yield losses. Examples of plants that may be treated with the compositions herein include major crops (corn, soybeans, hay, wheat, cotton, sorghum, rice, etc.) Examples of conditions resulting in crop losses are diseases caused by bacteria, viruses, and fungi. Other examples of conditions that may result in crop losses that can be preventable or diminished by the compositions herein include stress conditions such as drought, freezing, oxidative stress, unfavorable or reduced temperatures, infection by pathogens and other unfavorable environmental conditions.

In some embodiments, the compositions herein are used to modulate (e.g., increase, decrease or control) mitochondrial activity in plants. Examples of plants that may be treated with the compositions herein include ornamental crops: flower bulbs (e.g., Tulips, Daffodils, Hyacinths, Crocus, Dutch iris, Allium etc.), cut flowers (e.g., roses, carnation, lily, gladiolus, bird of paradise, etc); vegetable crop (e.g., tomato, cucumber, celery, eggplants, pumpkins, carrot, lettuce, zucchini, etc.); fruit crops (e.g., apple, citrus, peach, pear, plums, banana, pineapple, olive, avocado, papaya, mango, nuts, berries, and other types of agricultural crops such as grain (e.g., corn, soybeans, hay, wheat, barley, corn, cotton, sorghum, and rice) and trees used for lumber (e.g., Douglas fir, cedar, maple, oak, poplar).

In some embodiments, the compositions herein are used to modulate (e.g., increase, decrease or control) seed production that is regulated by plant temperature. Examples of plants that may be treated with the compositions herein include seeds of ornamental crops, vegetable crops, fruit and nut crops, seeds of other types of agricultural crops, or other plants disclosed herein.

In some embodiments, the compositions herein are used to modulate (e.g., increase, decrease or control) secretory products in plants or animals that are associated with changes in temperature. Such secretary products include, but are not limited to, small volatiles and non-volatile compounds such as terpenes, fatty acid oxidative products, and amines, as well as high molecular weight molecules such as polypeptides and polysaccharides. Such secretions can be, for example, involved in inter-, intra-cellular communications and/or diseases.

The invention herein also provides for nucleic acids that encode the compositions herein and nucleic acid that are complementary to nucleic acids that encode the compositions herein. Nucleic acids that encode the compositions herein can be inserted into a vector to express the polypeptides herein recombinantly. Nucleic acids that are complementary to the polypeptides herein can be used as diagnostics or research tools or to modulate the expression of certain polypeptides.

The compositions herein can be formulated with one or more carriers or excipients for delivery to an organism, such as an animal or a plant. Such carriers can be, for example, pharmaceutical carriers, veterinary carriers, and agricultural carriers. For delivery to an animal, the compositions herein may be administered in a therapeutically effective dose to reduce, inhibit, eliminate, ameliorate or prevent a condition. Similarly, for delivery to a plant (e.g., a crop plant), the compositions herein can be delivered in an effective dose to reduce, inhibit, eliminate, ameliorate or prevent a condition.

The invention also provides for antibodies or antibody fragments that are specific to the polypeptides herein. Such antibodies or antibody fragments can be used therapeutically, prophylactically, or for research purposes. Such antibodies or antibody fragments are preferably humanized and/or monoclonal.

The invention herein also provides for methods for screening for binding polypeptides (receptors) and for agents that modulate the composition herein, or their analogs (ligands) binding to the receptors. Binding affinity is determined by a competitive assay using labeled agents (e.g., biotinylated or fluorescent) incubated with the receptors in the presence of various concentrations of a composition of the invention. The affinity binding constant, $K_a$, has to be of greater than or equal to about $10^5$ to $10^7$ $M^{-1}$, preferably of greater than or equal to about $10^8$ $M^{-1}$, more preferably of greater than or equal to about $10^9$ $M^{-1}$ and still more preferably of greater than or equal to about $10^{10}$ $M^{-1}$. In certain embodiments binding affinity constants of peptides for the binding polypeptides may exceed $10^{11}$ to $10^{12}$ M$^{-1}$. Affinities of binding polypeptides for ligands according to the present invention can be readily determined using conventional techniques, for example those described by Scatchard et al. (1949 *Ann. N.Y. Acad. Sci.* 51:660), or by other various techniques described in the scientific literature.

The invention herein also provides for methods for preparing a peptidomimetic of the polypeptides herein.

DETAILED DESCRIPTION OF INVENTION

Figure 1:
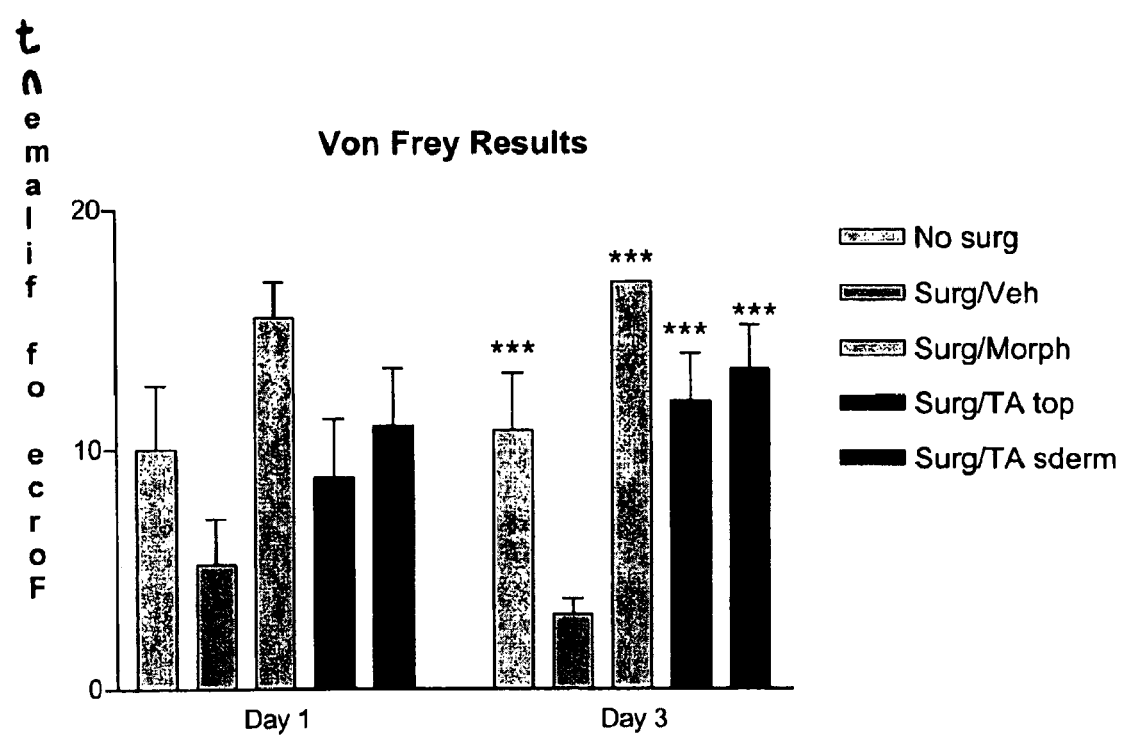
FIG. 1 illustrates the efficacy of SEQ ID NO: 1 in relieving pain in rats 3 days after surgery.

The present invention relates to compositions and methods for modulating mitochondria and mitochondrial related or metabolic related conditions.

In one aspect, a composition herein includes a polypeptide comprising, consisting essentially of, or consisting of a polypeptide selected from the group consisting of: SEQ ID NOs: 1-256, or more preferably selected from the group consisting of: SEQ ID NOs: 1-24, 50-244, and 248-249; or more preferably selected from the group consisting of: SEQ ID NOs: 1-2, or more preferably SEQ ID NO: 1.

In one aspect, a composition comprises a nucleic acid sequence encoding one or more of the above.

In one aspect, a composition comprises an antibody that specifically binds an epitope comprising one or more of the above polypeptides.

In one aspect, the present invention relates to a method for identifying novel compositions (e.g., polypeptides, peptide nucleic acids, nucleic acids, and small molecules) that modulate the mitochondria. Such methods include administering a test agent to a thermogenic plant; measuring temperature of said thermogenic plant; and determining if said test agent modulates temperature in said plant.

In one aspect, the compositions herein are used to treat a mitochondrial or metabolic condition selected from the group consisting of: innate immune response activation and ability to fight parasites and pathogens, pain, inflammation, temperature regulation, neoplastic growth (e.g., cancer), skin and dermatological conditions, and neurological and neurodegenerative conditions.

DEFINITIONS

The term "agonist" as used herein refers to a compound, molecule, or agent that stimulates a biological activity.

Examples of agonist molecules include, but are not limited to, agonists that stimulate receptors, e.g., morphine antagonist of the opiate μ receptors.

The term "amino acid" or "amino acid residue" refers to an amino acid, which is preferably in the L-isomeric form. When an amino acid residue is part of a polypeptide chain, the D-isomeric form of the amino acid can be substituted for the L-amino acid residue, as long as the desired functional property is retained. $NH_2$ refers to the free amino group present at the amino terminus of a polypeptide. COOH refers to the free carboxyl group present at the carboxyl terminus of a polypeptide. The amino acids herein can be represented by their standard 1-letter code or 3-letter code. An amino acid residue represented by "X" or "Xxx" refers to any one of the naturally occurring or non-naturally occurring amino acid residues known in the art or to a modification of a nearby residue. In keeping with standard protein nomenclature described in J. Biol. Chem., 1969, 247:3552-59, and adopted at 37 C.F.R. §§1.821-2461.822, all amino acid residue sequences represented herein by formulae have a left to right orientation in the conventional direction of amino-terminus to carboxyl-terminus. In addition, the phrase "amino acid residue" is broadly defined to include modified and unusual amino acids, such as those referred to in 37 C.F.R. §§1.821-1.822, and incorporated herein by reference. In a peptide or polypeptide, suitable conservative substitutions of amino acids are known to those of skill in this art and can be made generally without altering the biological activity of the resulting molecule. Watson et al., book (1987, *Molecular Biology of the Gene*, 4th Edition, The Benjamin Cummings Pub. Co., p. 224), is incorporated herein by references. Amino acid substitutions are typically of single residues, such substitutions are preferably made with those set forth in Table I, but may be of multiple residues, either clustered or dispersed. An amino acid can be replaced with a different naturally occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Additions encompass the addition of one or more naturally occurring or non-conventional amino acid residues. Deletion encompasses the deletion of one or more amino acid residues.

TABLE I

Conservative amino acid substitution

| Original residue | Conservative substitution(s) |
| --- | --- |
| Ala | Gly; Ser |
| Arg | Lys |
| Asn | Gln; His |
| Cys | Ser |
| Gln | Asn |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr, Ile |
| Phe | Met; Leu; Tyr |
| Ser | Thr |
| Thr | Ser |
| Trp | Tyr |
| Tyr | Trp; Phe |
| Val | Ile; Leu |

Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino acid with alanine), or alternatively, in which a naturally-occurring amino acid is substituted with a non-conventional amino acid.

The term "analog(s)" as used herein refers to a composition that retains the same structure or function (e.g., binding to a receptor) as a polypeptide or nucleic acid herein, such as the same gene from a different organism. Examples of analogs include mimetics or peptidomimetics, peptide, nucleic acids, small and large organic or inorganic compounds, as well as derivatives and variants of a polypeptide or nucleic acid herein. Such derivatives and variants refer to peptides and nucleic acids that differ from the naturally occurring polypeptides and nucleic acids by one or more amino acid or nucleic acid deletions, additions, substitutions or side-chain modifications. In some embodiments, a peptide analog is a peptide in which one or more of the amino acids has undergone side-chain modifications. Examples of side-chain modifications contemplated by the present invention include modifications of amino groups such as by reductive alkylation by reaction with an aldehyde followed by reduction with NaBH4; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$. In some embodiments, a peptide analog is one in which the guanidine group of arginine residue(s) is modified by the formation of heterocyclic condensation products with reagents such as 2,3-butanedione, phenylglyoxal and glyoxal; carboxyl group(s) is modified by carbodiimide activation via O-acylisourea formation followed by subsequent derivitisation, for example, to a corresponding amide; sulphydryl group(s) may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. In any of the analogs herein, any modification of cysteine residues preferably do not affect the ability of the peptide to form the necessary disulphide bonds. In some embodiments, a peptide analog comprises tryptophan residue(s) that are modified by, for example, by oxidation with N-bromosuccinimide or alkylation of the indole ring with 2-hydroxy-5-nitrobenzyl bromide or sulphenyl halides; tyrosine residues altered by nitration with tetranitromethane to form a 3-nitrotyrosine derivative; imidazole ring(s) of a histidine residue modification accomplished by alkylation with iodoacetic acid derivatives or N-carbethoxylation with diethylpyrocarbonate; proline residue(s) modified by, for example, hydroxylation in the 4-position; glycosylation variants from a completely unglycosylated molecule to a modified glycosylated molecule; and altered glycosylation patterns as a result from expression of recombinant molecules in different host cells.

The term "antagonist" as used herein refers to a compound, molecule, or agent that inhibits a biological activity. Examples of antagonist molecules include, but are not limited to, peptides, small molecules, antibodies, antisense nucleic acids, siRNA nucleic acids, and other binding agents.

The term "antibody" is used in the broadest sense and specifically covers, for example, polyclonal antibodies, monoclonal antibodies (mAbs) (including agonist, antagonist, and neutralizing antibodies), chimeric antibodies, antibody compositions with mono and polyepitopic specificity, single chain antibodies, anti-idiotypic (anti-Id) antibodies to antibodies that can be labeled in soluble or bound form, polymers and conjugates of immunoglobulins, as well as fragments, regions or derivatives thereof (e.g., separate heavy chains, light chains, Fab, F(ab')2, Fabc, and Fv). Antibody fragments can be prepared for example by enzymatic cleavage of antibodies with enzymes such as pepsin or papain. Antibody aggregates, polymers and conjugates can be generated by diverse methods, e.g. by thermal treatment, reaction with substances such as glutaraldehyde, reaction with immunoglobulin-binding molecules, biotinylation of antibodies and subsequent reaction with streptavidin or avidin. The term "monoclonal antibody" as used herein refers to an antibody obtained from a population of substantially homogeneous antibodies, i.e., the individual antibodies comprising the population are identical except for possible naturally-occurring mutations that may be present in minor amounts.

The term "antigens" includes monovalent and polyvalent antigens. A polyvalent antigen is a molecule or a molecule complex to which simultaneous binding of more than one immunoglobulin is possible, whereas a monovalent antigen can bind only a single antibody at each particular time. Hapten is normally the designation given to a molecule which is not immunogenic per se but which is normally bound to a carrier for immunization purposes.

The term "effective amount" as used herein when referring to a composition means the amount or dosage of that composition that is required to induce a desired effect. In some embodiments, an effective dose refers to an amount that is required to induce a local analgesic, anti-pyrogenic, flowering, pesticide, anti-dementia, and/or anti-inflammatory effect.

The term "fragment" as used herein refers to a portion of a composition. For example, when referring to a polypeptide, a fragment of a polypeptide is some but not the entire amino acid polymer that comprises the polypeptide. A polypeptide fragment can have up to 99, 95, 90, 85, 80, 75, 70, 65, or 60% of the sequence of the parent polypeptide. In some embodiments, a fragment has between 3-40, 3-30, 4-20, or 4-10 amino acids of the parent sequence.

The terms "gene therapy" and "genetic therapy" refer to the transfer of heterologous nucleic acids to the certain cells, target cells, of a mammal, particularly a human, with a disorder or conditions for which such therapy is sought. The nucleic acid is introduced into the selected target cells in a manner such that the heterologous DNA is expressed and a therapeutic product encoded thereby is produced. Alternatively, the heterologous nucleic acids can in some manner mediate expression of a nucleic acid that encodes the therapeutic product; it can encode a product such as a peptide or RNA that in some manner mediates, directly or indirectly, expression of a therapeutic product. Genetic therapy can also be used to nucleic acid encoding a gene product replace a defective gene or supplement a gene product produced by the mammal or the cell in which it is introduced.

The term "homolog" when referring to a polymer (e.g., a peptide or a nucleic acid) refers to a second polymer that has at least about 50 sequence identity, more preferably at least 55% sequence identity, more preferably at least 60% sequence identity, more preferably at least 65% sequence identity, more preferably at least 70% sequence identity, more preferably at least 55% sequence identity, more preferably at least 80% sequence identity; or preferably at least about 81% sequence identity, more preferably at least about 82% sequence identity, yet more preferably at least about 83% sequence identity, yet more preferably at least about 84% sequence identity, yet more preferably at least about 85% sequence identity, yet more preferably at least about 86% sequence identity, yet more preferably at least about 87% sequence identity, yet more preferably at least about 88% sequence identity, yet more preferably at least about 89% sequence identity, yet more preferably at least about 90% sequence identity, yet more preferably at least about 91% sequence identity, yet more preferably at least about 92% sequence identity, yet more preferably at least about 93% sequence identity, yet more preferably at least about 94% sequence identity, yet more preferably at least about 95% sequence identity, yet more preferably at least about 96% sequence identity, yet more preferably at least about 97% sequence identity, yet more preferably at least about 98% sequence identity and yet more preferably at least about 99% sequence identity and preferably the same function. For example, a polypeptide homologous to any of the polypeptides herein (e.g., SEQ ID NOs: 1-256) is one that preferably has at least 80% sequence identity and similar function of modulating mitochondrial activity, or more preferably acting as an agonist or antagonist to SEQ ID NO: 5 or agonist to heat production of 2,6-DHBA.

The term "isolated" means altered from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. For example, with respect to polynucleotides, the term isolated means that it is separated from the nucleic acid and cell in which it naturally occurs.

The term "protein", "peptide", "oligopeptides" or "polypeptide" as used herein refers to any composition that includes two or more amino acids joined together by a peptide bond. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention include, but are not limited to, acetylation, acylation, ADP-ribosylation, amidation, covalent attachment of a flavanoid or a heme moiety, covalent attachment of a polynucleotide or polynucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycation, glycosylation, glycosylphosphatidyl inositol (GPI) membrane anchor formation, hydroxylation, iodination, methylation, myristoylation, oxidation, proteolytic processing, phosphorylation, prenylation, racemization, selenoylation, sulfation, transfer-RNA mediated addition of amino acids to polypeptides such as arginylation, and ubiquitination. The term "protein" also includes "artificial proteins" which refers to linear or non linear polypeptides, consisting of alternating repeats of a peptide (e.g., SEQ ID NO: 1-256), and a spacer. A DNA-construct encoding the peptide and a spacer alternate repeats can be synthesized using methods known in the art. (Rötzschke et al., 1997, Proc. Natl. Acad. Sci. USA 94:14642-14647). The above methods allow for the amplification of the antigenicity of the peptide and for insertion into an expression vector at high levels.

The term "opioid" as used herein means all agonists and antagonists of opioid receptors, such as mu (µ), kappa (κ), and delta (δ) opioid receptors and subtypes thereof. For a discussion of opioid receptors and subtypes see Goodman and Gilman's *The Pharmacological Basis of Therapeutics* 9th ed. J. G. Harman and L. E. Limird Eds., McGraw-Hill N.Y., 1996, pp. 521-555, which is incorporated herein by reference for all purposes. The opioid can be any opioid receptor agonist or antagonist known or to be developed. Preferred opioids interact with the µ-opioid receptor or the κ- and δ-opioid receptors. Preferably, the opioid is an opioid-receptor agonist.

The term "organism" as used herein can be, for example, a microorganism (e.g., virus or bacteria), plant (e.g., crop plants such as soy, wheat, barley, rice, corn, sugar, etc.), or animal. Animals include both mammals (e.g., farm animals, donkeys, goats, chicken, rabbits, dogs, cats, swine, cattle, sheep, horses, or primates) and non-mammals, e.g., (e.g., insects and birds). Preferably an animal is a mammal, or more preferably a human.

The term "purified" as used herein to describe a polypeptide, polynucleotide, or other compositions, refers to such polypeptide, polynucleotide, or other composition separated from one or more compounds which are usually associated with it in nature. Such other compositions can be, for example, other polypeptides or polynucleotides, carbohydrates, lipids, etc. The term "purified" can also be used to specify the separation of monomeric polypeptides of the invention from oligomeric forms such as homo- or heterodimers, trimers, etc. The term "purified" may also be used to specify the separation of covalently closed (i.e. circular) polynucleotides from linear polynucleotides. A substantially pure polypeptide or polynucleotide typically comprises at least about 50%, 60%, 70%, 80%, or 90% weight/weight of a polypeptide or polynucleotide sample, or more preferably at least about 95%, 96%, 97%, 98%, 99%, or 99.5% weight/weight of a polypeptide or polynucleotide sample. As a preferred embodiment, a polypeptide or polynucleotide of the present invention is at least 10%, 20%, 30%, 40%, 50%, 60%, 70%, 80%, 90%, 95%, 96%, 96%, 98%, 99%, or 100% pure relative to heterologous polypeptides and polynucleotides, respectively.

Compositions

The compositions herein are based on a class of phylogenetically related plant reductases: pinoresinol-lariciresinol reductase, isoflavone reductase, and phenylcoumaran benzylic ether reductase (Gang et al., J. Biol. Chem., 1999, 274: 7516-7527) having sequences SEQ ID NOs: 245-247, human beta-neoendorphin-dynorphin precursor (Proenkephalin B) having sequence SEQ ID NO: 250; protein from *Arabidopsis thaliana* (E71436) having sequence SEQ ID NO: 253, Epsin 1, EPS-15 interacting protein 1 derived from human having sequence SEQ ID NO: 254, phosphatidylinositol polyphosphate 5-phosphatase isoform derived from human having sequence SEQ ID NO: 255, and RNA2 polyprotein (P2) derived from ssRNA positive-strand viruses, having sequence SEQ ID NO: 256.

SEQ ID NO: 245 *Arabidopsis* phenylcoumaran benzylic ether reductase homolog Tp1 [Thuj plicata (ACCESSION AAF64183) having sequence

MDKKSRVLIVGGTGFIGKRIVKASLALGHPTYVLFRPEALSYIDKVQMLISFKQLGAKLLEASLDDHQG

LVDVVKQVDVVISAVSGGLVRHHILDQLKLVEAIKEAGNIKR*FLPS*FGMDPDVVEDPLEPGNITFIDK

RKVRRAIEAATIPYTYVSSNMFAGFFAGSLAQLQDAPRMMPARDKVLIYGDGNVKGVYVDEDDAGIY

IVKSIDDPRTLNKTVYIRPPMNILSQKEVVEIWERLSGLSLEKIYVSEDQLLNMKDKSYVEKMARCHLY

HFFIKGDLYNFEIGPNATEGTKLYPEVKYTTMDSYMERYL

SEQ ID NO 246 is pinoresinol-lariciresinol reductase from *Arabidopsis thaliana* (ACCESSION NM_102944) having sequence

MGESKRTEKTRVLVVGATGYIGKRIVRACLAEGHETYVLQRPEIGLEIEKVQLFLSFKKLGARIVEGSFS

DHQSLVSAVKLVDVVVSAMSGVHFRSHNILVQLKLVEAIKEAGNVKR *FLPS*EFGMDPPRMGHALPPG

RETFDQKMERQAIEAAGIPYTYVVGACFAAYFAGNLSQMVTLLPPKEKVNIYGDGNVKVVFADEDDI

AKYTAKTLNDPRTLNKTVNIRPPDNVLTQLELVQIWEKLTGKELEKTNIAAQDFLANIEQMEIPHQAGI

GHFYHIFYEGCLTDHEVGEDEEASSLYPDVKYKRMDDYLRMFL

SEQ ID NO: 247 is *Arabidopsis thaliana* mRNA for isoflavonoid reductase homologue (ACCESSION Z49777) having sequence

MATEKSKILVIGGTGYIGKFLVEASAKAGHSTFALVREATLSDPVKGKTVQSFKDLGVTILHGDLNDHE

SLVKAIKQVDVVISTVGSMQILDQTKIISAIKEAGNVKR*FLPS*EFGVDVDRTSAVEPAKSAFAGKIQIRR

TIEAEGIPYTYAVTGCFGGYYLPTLVQFEPGLTSPPRDKVTILGDGNAKAVINKEEDIAAYTIKAVDDPR

TLNKILYIKPSNNTLSMNEIVTLWEKKIGKSLEKTHLPEEQLLKSIQESPIPINVVLSINHAVFVNG

DTNISIEPSFGVEASELYPDVKYTSVDEYLSYFA

SEQ ID NO: 250 is human beta-neoendorphin-dynorphin precursor (Proenkephalin B) (Preprodynorphin), (ACCESSION P01213) having sequence

MAWQGLVLAACLLMFPSTTADCLSRCSLCAVKTQDGPKPINPLICSLQCQAALLPSEEWERCQSFSFFT

PSTLGLNDKEDLGSKSVGEGPYSELAKLSGSFLKELEKSK*FLPS*ISTKENTLSKSLEEKLRGLSDGFREG

AESELMRDAQLNDGAMETGTLYLAEEDPKEQVKRYGGFLRKYPKRSSEVAGEGDGDSMGHEDLYKR

YGGFLRRIRPKLKWDNQKRYGGFLRRQFKVVTRSQEDPNAYSGELFDA

SEQ ID NO: 253 is a protein from *Arabidopsis thaliana* (E71436) having sequence:

MVKKIANDVSNKLFPLPKGFGDFVGIEDHIKAIKSLLCLESKEARIMVGIWGQSGIGKSTIGRALFSQLSS

QFHHRAFITYKSTSGSDVSGMKLSWEKELLSEILGQKDIKIDHFGVVEQRLKHKKVLILLDDVDNLEFL

KTLVGKAEWFGSGSRIIVITQDKQLLKAHEIDLVYEVELPSQGLALKMISQYAFGKDSPPDDFKELAFE

VAELVGSLPLGLSVLGSSLKGRDKDEWVKMMPRLRNDSDDKIEETLRVGYDRLNKKNRDNVKELLE

-continued

DDVGLTMLADKSLIRITPDGDIEMHNLLEKLGREIDRAKSKGNPAKRQFLTNFEDIQEVVTEKTGTETV

LGIRVPPTVLFSTRPLLVINEESFKGMQIGLWSKIDLPQGLVYLPLKLKLLKWNYCPLKSLPSTFKAEYL

VNLIMKYSKLEKLWEGTLPLGSLKKMDLGCSNNLKEIPDLSLAINLEELNLSKCESLVTLPSSIQNAIKL

RTLYCSGVLLIDLKSLEGMCNLEYLSVDWSSMEGTQGLIYLPRKLKRLWWDYCPVKRLPSNFKAEYL

VELRMENSDLEKLWDGTQPLGSLKEMYLHGSKYLKEIPDLSLAINLERLYLFGCESLVTLPSSIQNATK

LINLDMRDCKKLESFPTDLNLESLEYLNLTGCPNLRNFPAIKMGCSYFEILQDRNEIEVEDCFWNKNLP

AGLDYLDCLMRCMPCEFRPEYLTFLDVSGCKHEKLWEGIQIHALLDGYELAGHLDGSIETPAPTLTTN

NVVSANPQYTLWKRQDRLIFSALIGAISPPVQPLVSRATKASQIWKTLTNTYAKSSYDHIKQLRTQIKQL

KKGTKTIDEYVLSHTTLLDQLAILGKPMEHEEQVERILEGLPEDYKTVVDQIEGKDNTPSITEIHERLINH

EAKLLSTAALSSSSLPMSANVAQQRHHNNNRNNNQNKNRTQGNTYTNNWQPSANNKSGQRPFKPYL

GKCQICNVQGHSARRCPQLQAMQPSSSSSASTFTPWQPRANLAMGAPYTANNWLLDSGATHHITSDL

NALALHQPYNGDDVMIADGTSLKITKTGST _FLPS_NARDLTLNKVLYVPDIQKNLVSVYRLCNTNQVSV

EFFPASFQVKDLNTGTLLLQGRTKDELYEWPVTNPKATALFTTPSPKTTLSSWHSRLGHPSSSILNTLIS

KFSLPVSVSASNKLACSDCFINKSHKLPFSISSIKSTSPLEYIFSDVWMSPILSPDNYKYYLQKSQVKSTFI

AFKALVENRFQAKIRTLYSDNGGEFIALREFLVSNGISHLTSPPHTPEHNGLSERKHRHIVETGLTLLTQ

ASVPREYWPYAFAAAVYLINRMPTPVLSMESPFQKLFGSKPNYERLRVFGCLCFPWLRPYTHNKLEER

SRRCVFLGYSTQTAYLCFDVEHKRLYTSRHVVFDEASFPFSNLTSQNSLPTVTFEQSSSPLVTPILSSSSV

LPSCLSSPCTVLHQQQPPVTTPNSPHSSQPTTSPAPLSPHRSTTMDFQVPQPTAPNENGPEPEAQSPPIGP

LSNPTHEAFIGPLPNPNRNPTNEIEPTPAPHPKPVKPTTTTTTPNRTTVSDASHQPTAPQQNQHNMKTRA

KNNIKKPNTKFSLTATLPNRSPSEPTNVTQALKDKKWRFAMSDEFDAQQRNHTWDLVPHESQLLVGC

KWVFKLKYLPNGAIDKYKARLVAKGFNQQYGVDYAETFSPVIKSTTIRLVLDVAVKKDWEIKQLDVN

NAFLQGTLTEEVYMAQPPGFIDKDRPTHVCRLRKAIYGLKQAPRAWYMELKQHLFNIGFVNSLSDASL

FIYWSDKSSIDAVLTSLAERFSIKDPTDLHYFLGIEATRTKQGLHLMQRKYIKDLLAKHNMADAKPVLT

PLPTSPKLTLHGGTKLNDASEYRSVVGSLQYLAFTRPDIAYAVNRLSQLMPQPTEDHWQAAKRVLRYL

AGTSTHDWAGDSDDYVSTNAYVIYLGKNPISWSSKKQRGVARSSTESEYRAVANAASEVKWLCSLLS

KLHIRLPIRPSIFCDNIGATYLCANPVFHSRMKHIAIDYHFVRNMIQSGALRVSHVSTRDQLADALTKPL

SRAHFQSARFKIGVRQLPPS

SEQ ID NO: 254 is Epsin 1, EPS-15 interacting protein 1 derived from human (Accession No. O88339) having sequence:

MSTSSLRRQMKNIVHNYSEAEIKVREATSNDPWGPSSSLMSEIADLTYNVVAFSEIMSMIWKRLNDHG

KNWRHVYKAMTLMEYLIKTGSERVSQQCKENMYAVQTLKDFQYVDRDGKDQGVNVREKAKQLVA

LLRDEDRLREERAHALKTKEKLAQTATASSAAVGSGPPPEAEQAWPQSSGEEELQLQLALAMSKEEA

DQPPSCGPEDDVQLQLALSLSREEHDKEERIRRGDDLRLQMAIEESKRETGGKEESSLMDLADVFTTPA

PPQASDPWGGPASVPTAVPVAAAASDPWGAPAVPPAADPWGGAAPTPASGDPWRPAAPTGPSVDPW

GGTPAPAAGEGPTSDPWGSADGGAPVSGPPSSDPWAPAPAFSDPWGGSPAKPSSNGTAVGGFDTEPDE

FSDFDRLRTALPTSGSSTGELELLAGEVPARSPGAFDMSGVGGSLAESVGSPPPAATPTPTPPTRKTPESF

LGPNAALVDLDSLVSRPGPTPPGAKASNP _FLPS_GAPATGPSVTNPFQPAPPATLTLNQLRLSPVPPVPGA

PPTYISPLGGGPGLPPM MPPGPPAPNT NPFLL

SEQ ID NO: 255 is phosphatidylinositol polyphosphate 5-phosphatase isoform derived from human (Accession No. NP_000267) having sequence:

MEPPLPVGAQPLATVEGMEMKGPLREPCALTLAQRNGQYELIIQLHEKEQHVQDIIPINSHFRCVQEAE

ETLLIDIASNSGCKIRVQGDWIRERRFEIPDEEHCLKFLSAVLAAQKAQSQLLVPEQKDSSSWYQKLDT

KDKPSVFSGLLGFEDNFSSMNLDKKINSQNQPTGIHREPPPPPPFSVNKMLPREKEASNKEQPKVTNTMR

KLFVPNTQSGQREGLIKHILAKREKEYVNIQTFRFFVGTWNVNGQSPDSGLEPWLNCDPNPPDIYCIGF

QELDLSTEAFFYFESVKEQEWSMAVERGLHSKAKYKKVQLVRLVGMMLLIFARKDQCRYIRDIATET

VGTGIMGKMGNKGGVAVRFVFHNTTFCIVNSHLAAHVEDFERRNQDYKDICARMSFVVPNQTLPQLN

IMKHEVVIWGDLNYRLCMPDANEVKSLINKKDLQRLLKFDQLNIQRTQKKAFVDFNEGEIKFIPTYKY

DSKTDRWDSSGKCRVPAWCDRILWRGTNVNQLNYRSHMELKTSDHKPVSALFHIGVKVVDERRYRK

VFEDSVRIMDRMEND ___FLPS___LELSRREFVFENVKFRQLQKEKFQISNNGQVPCHFSFIPKLNDSQYCKPW

LRAEPFEGYLEPNETVDISLDVYVSKDSVTILNSGEDKIEDILVLHLDRGKDYFLTISGNYLPSCFGTSLE

ALCRMKRPIREVPVTKLIDLEEDSFLEKEKSLLQMVPLDEGASERPLQVPKEIWLLVDHLFKYACHQED

LFQTPGMQEELQQIIDCLDTSIPETIPGSNHSVAEALLIFLEALPEPVICYELYQRCLDSAYDPRICRQVIS

QLPRCHRNVFRYLMAFLRELLKFSEYNSVNANMIATLFTSLLLRPPPNLMARQTPSDRQRAIQF

LLGFLLGSEED

SEQ ID NO: 256 is RNA2 polyprotein (P2) derived from ssRNA positive-strand viruses, Comoviridae (Accession No. Q9YK98) having sequence:

MSESGNTTSMPGCGRMCALRSTWSKRAFLVACKDGALTSDGRCPQYGCGALVSITKGVQQPKKTAS

AKVVKCLCWVQPARWCEKHSKGPASPNGSVTTKRSNSARAAPAPLPYKKQTCDVVVTVGPLELVYP

ALVSEELPTPVAATPTKVEEVPIPELPLWLAPAWMVEQPYAATPEVLCLTQREEFALLKKRLTRKGKLL

QRRATHARFEARAALARVRAATQRKVEEVTALVIKGRRILAAHQLLRELEEVAPLSQAQEQLVASSCA

AAAARQEECASFLRRAKAWRKSISATPPVAATAVASKVVSATMPWAHLGLSLGGLLAVPTLDGTLGA

KQWNAKTIATWVLKPVVSCVQSVHAKVRDWLHSQPEVGVTNTKVPLVLPEVCLGVLSPPSLSEEIVD

NPQETSQSGIWHPEMGVRNIYVFHDDSWETSPEEDENYTYTFSRQCGIPYLLVEGRGAEERKNTILGW

DFSLHNDGFE ___FLPS___PEEGYTKELVTPVALEEEDKYSTASSCGFFSLDDVSSAITIQCPGLLSADADVHFF

DGPGYRCSSRPRDFRPPVVRGCDYESRVKASIQRKIENPLQERFITVLREKRKKNKKKEFHSFSACFAFK

RKQIQWPPTPNEMVNEWEEYCIAQAWLPFEVVVTDEIEDVTPLYPGGRDYNCNSQLLFPLAPLSTVYC

DDSCFHPNDGWTTDGNGKHFRLSPQFVLPDVPIPIVHRVTRQLPQFLYDLGIGDLTCNSGYQAENLQEE

IQERMEDRSEEKPVPSLDTLISKLSKRSTKVKGAGENRYADRHSLTEKAIFHQPGALSRMRSGKEKTIV

AANHNSDQISVRMAECGKPVFTPLPRMSDEMLRKFLEKGLGSTSTVALDIGIQSHIPQGMPTVAFVNV

MDTRIEDPLYSSLCGSYIDLGRDRAKTLCLPLVNFPMSKLAEDVDDVLNGLMLCTHFQDSTKFGVGKP

AFQYGTLEFQEFKPSAYSDFSRVRDNWDAIAKQQNTPNDRILAGFSVLGAVSQAYNQALPVFKSVELV

APPKRKPVVATFQNPTTLGRSNTTRSFRMPTMDLPRSTGRDAPIPIVHRRNNNDVHFDEATPARFSTCD

SGLVADTTLAFAKMYQCKKDAKAGHVLATIDIQECVFEDNRRVALDWLAHGLASFKYDLQLTVDSN

PFVGVTLGITVDAFDRLLPQISDEVIAVPLAFQLPTYLFPISKKGTFTQTIDFAAIAGYNFFPHVAAFGRP

KIIVYIVSDNDLPASDTWMCLVELHMTRLESSTLACSPTLVLPQAFGGDLPLDLWRGPYTFPLGGGTKR

LSTSLDIGTSTTTVSGWRTVSPAAYALFLQGHGGSLVGEVVHTGSAAVSCALHLCISFGGAPPTLEEAL

-continued

```
VFPGERLPSGEGKFHIKVQTPYGRLSTLTPDCALYVYLAGGPIAVAPMSVPYQFCIHLERLVDDGAPPR

TIGLIREFNWATINNFKSDDITFAIPARLSDLVLTCGDVTMSTNPLALLIGSCGFFRGNLTVVLEWATFL

KAGDKEGTVQLTTCRGMINNVKGVRNAIQKKVVNLSLVGSVSRYLNVGDFTGFAQSGGQVGYDEIFL

EFSTNKAKQIRYLNINVELDENFELYGRTIIPLKNTAPAFASTSSAPNES
```

Peptides opioids derived from SEQ ID NOs: 245-247 include those of SEQ ID NOs: 1-24 and 50-152. Known peptides opioids derived from SEQ ID NO: 250 are β-neoendorphin (SEQ ID NO: 16); Dynorphin A (SEQ ID NO: 19); Leumorphin (SEQ ID NO: 249); Rimorphin (SEQ ID NO: 248); Leu-enkephalin (SEQ ID NO: 15). In addition, SEQ ID NO: 1 is also derived from SEQ ID NO: 250, and 253-256. These peptides are shown highlighted in the sequence listing above.

In some embodiments, the compositions herein are synthetic peptides derived from or fragments of the above gene sequences. Such peptide fragments include those having an amino acid sequence comprising, consisting essentially of or consisting of SEQ ID NOs: 1-14, 50-152 and 248-249 including homologs and analogs thereof. When a polypeptide of the invention comprises any of the above peptide sequences, additional amino acid residues in its C-terminus or N-terminus can be derived from any of the above gene sequence or any sequences that are homologs or analogous to the above gene sequences. For example, SEQ ID NO: 1 is derived from SEQ ID NO: 250 as well as SEQ ID NO: 246. Thus, in some embodiments, the present invention contemplates a 5-mer derived from SEQ ID NO 250 such as KFLPS (SEQ ID NO: 257) or FLPSI (SEQ ID NO: 258) or a 5-mer derived from SEQ ID NO: 246 such as RFLPS (SEQ ID NO: 259) or FLPSE (SEQ ID NO: 260). In any of the embodiments herein, a polypeptide can be a 3-mer, 4-mer, 5-mer, 6-mer, 7-mer, 8-mer, 9-mer, 10-mer, 11-mer, 12-mer, 13-mer, 14-mer, 15-mer, or larger polypeptides, but is preferably up to 40, 30, 20, or 10 amino acids long.

To eliminate vulnerability to degradation once inside the cell, the reverse sequences of any of the polypeptides herein can be used (with or without D-amino acids), especially the polypeptides comprising, consisting essentially of, or consisting of: SEQ ID NOs: 1-152, and 245-256. Such reverse sequences include those in SEQ ID NOs: 153-244. The reverse polypeptides can retain essentially the same function (e.g., relieving pain) but are resistant to degradation.

In preferred embodiments, a composition comprises a polypeptide consisting of SEQ ID NOs: 1-14, 50-152, 248-249, or more preferably SEQ ID NOs: 1, 2, and 15 or homologs, analogs, or fragments thereof. The sequence of SEQ ID NOs: 1 and 2 is found in both humans and plants. In some embodiments, the invention relates to SEQ ID NO: 3 and various fragments of SEQ ID NO: 3, such as SEQ ID NOs: 2-14.

In some embodiments, the compositions herein include a peptide having the reverse amino acid sequence of any of the above amino acid sequences, such as SEQ ID NOs: 153-244.

In one aspect, the present invention contemplates the above synthetic peptides and all other peptide fragments and derivatives from pinoresinol-lariciresinol reductase, isoflavone reductase, and phenylcoumaran benzylic ether reductase. In one embodiment, the present invention relates to a peptide fragment from pinoresinol-lariciresinol reductase, which is between 3-50, 3-40, 3-30, 3-20, or 3-10 amino acids in length. In another embodiment, the present invention relates to a peptide fragment from isoflavone reductase which is between 3-50, 3-40, 3-30, 3-20, or 3-10 amino acids in length. In another embodiment, the present invention relates to a peptide fragment from phenylcoumaran benzylic ether reductase which is between 3-50, 3-40, 3-30, 3-20, or 3-10 amino acids in length. Preferably, such peptides have at least one phenylalanine or at least two phenylalanines. In some embodiments, such peptides comprise the sequence Phe-Leu-Pro-Ser (SEQ ID NO: 1). Any of the peptides herein are contemplated in both their forward and reverse sequences. SEQ ID NOs: 152-244 are the reverse sequences of SEQ ID NOs: 1-14 and 50-151.

In another aspect, the present invention relates to nucleic acids that encode any of the above peptides and antibody that specifically bind any of the above peptides.

In some embodiments, the above compositions (e.g., peptides) can be used to modulate effects of SEQ ID NO: 49, which is the Alzheimer's peptide, Aβ 1-42.

In some embodiments, the above compositions (e.g., peptides) can be used modulate or enhance the effects of SEQ ID NOs: 15-48, 248-249, which are known opioid peptides.

In some embodiments, the above compositions (e.g., peptides) can be used to create a library to analyze functionality of compounds and compositions that regulate mitochondria activities.

In some embodiments, the above compositions (e.g., peptides) can be used for screening antagonists, agonists, and modulators of different mitochondrial activities.

1. Polypeptides

The present invention relates to composition comprising, consisting essentially of, or consisting of one or more polypeptides that comprise, consist essentially of, or consist of an amino acid sequence selected from the group of SEQ ID NOs: 1-244, 248-249, as well as the sequences which are the reverse of the above and any homologs, analogs, salts, prodrugs, fragments, metabolites, and combination thereof. Preferably, a composition herein comprises a polypeptide having an amino acid sequence comprising SEQ ID NOs 1-14 or 50-244, 248-249, or consisting essentially of a polypeptide having an amino acid sequence comprising SEQ ID NOs: 1-14 or 50-244, 248-249, or consisting of a polypeptide having an amino acid sequence comprising SEQ ID NO: 1-14 or 50-244, 248-249, or comprising SEQ ID NOs: 1-2, or consisting essentially of SEQ ID NOs: 1-2, or consisting of SEQ ID NOs: 1-2, or comprising of SEQ ID NO: 1, or consisting essentially of SEQ ID NO: 1, or consisting of SEQ ID NO: 1.

In some embodiments, a composition comprises more than 1, 2, 3, 4, and 5 of the polypeptides above.

The polypeptides herein may be created synthetically by any means known in the art (synthetically synthesized or using recombinant DNA technology). In some embodiments, they may include an additional methionine at the N-terminus (e.g., SEQ ID NO: 105, MFAGYFAG) or an N-terminus methionine may be included on to them.

In some embodiments, a polypeptide herein has up to about 100, 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, or more preferably 4 amino acids residue; or at least about 3, 4, 5, 6, 7, 8, 9, 10, 11, 12, 12, 13, 14, 15, 16, 17, 18, 19, 20, 25, 30, 35, 40, 45, or 50, amino acid residues; or between about 2-50, 2-40, 2-30 or 2-10 amino acid residues. In some embodiments, a polypeptide herein has up to 500,000, 100,000, 75,000, 50,000, 15,000, 14,000, 13,000, 12,000, 11,000, 10,000, 9,000, 8,000, 7,000, 6,000, 5,000, 4,000, 3,000, 2,000, 1,000, 900, 800, 700, 600, 500, 400, 300, or 200 Daltons. In some embodiments, a polypeptide herein has between 200-200,000, 300-100,000, 400-50,000, or 500-1000 Daltons.

The polypeptides herein are preferably isolated such that it is free of other compounds or molecules that it normally is associated with in vivo. For example, an isolated peptide of the invention can constitute at least about 50%, more preferably about 55%, more preferably about 60%, more preferably about 65%, more preferably about 70%, more preferably about 75%, more preferably about 80%, more preferably about 85%, more preferably about 90%, more preferably about 95%, or more preferably about 99% w/w of a sample containing it. In some embodiments, a polypeptide of the invention is purified.

In some embodiments, a polypeptide herein is modified or adapted for slow-release. Such modification can include substitution of one or more, 2 or more, 3 or more, or 4 or more amino acids residues from an L-amino acid residue to a D-amino acid residue. In some embodiments at least about 10%, 20%, 30%, 40%, 50%, 60%, 70%, 80%, 90% or 100% of the residue in a polypeptide are D-amino acids.

In some embodiments, a polypeptide of the present invention includes one or more post-translational modifications, e.g., N-linked or O-linked carbohydrate chains, processing of N-terminal or C-terminal ends, attachments of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the polypeptide.

Also provided by the invention are chemically modified derivatives of the polypeptides of the invention, which may provide additional advantages such as increased solubility, stability and circulating time of the polypeptide, or decreased immunogenicity. See U.S. Pat. No. 4,179,337. The chemical moieties for derivitization may be selected. See, U.S. Pat. No. 4,179,337, which is hereby incorporated by reference in its entirety. The chemical moieties for derivitization may be selected from water-soluble polymers such as polyethylene glycol (PEG), copolymers, carboxymethylcellulose, dextran, polyvinyl alcohol and the like. Such derivitization may occur at random positions within the molecule, or at predetermined positions within the molecule and may include one, two, three or more attached chemical moieties.

For example, in some embodiments the chemical moiety used for derivitization may be a polymer of any molecular weight, and may be branched or unbranched. If PEG is used for derivitization, the preferred molecular weight is between about 1 kDa and about 100 kDa (the term "about" indicating that in preparations of PEG, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the PEG to a therapeutic polypeptide or analog).

The PEG molecules (or other chemical moieties) should be attached to the polypeptide with consideration of effects on functional or antigenic domains of the polypeptide. There are a number of attachment methods available to those skilled in the art, e.g., EP 0 401 384, (coupling PEG to Granulocyte Colony Stimulating Factor (G-CSF)), Malik et al., (1992), Exp. Hematol. 20:1028-1035. This article reports on pegylation of Granulocyte/Macrophage Colony Stimulating Factor (GM-CSF) using tresyl chloride, which its disclosures is hereby incorporated by reference in its entireties. For example, PEG may be covalently bound through amino acid residues via a reactive group, such as, a free amino or carboxyl group. Reactive groups are those to which an activated PEG molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the PEG molecules. Preferred for therapeutic purposes is attachment at an amino group, such as attachment at the N-terminus or lysine group.

The polypeptides herein can be chemically modified at the N-terminus. Using PEG as an illustration of the present composition, one may select from a variety of PEG molecules (by molecular weight, branching, etc.), the proportion of PEG molecules to polypeptide (polypeptide) molecules in the reaction mix, the type of pegylation reaction to be performed, and the method of obtaining the selected N-terminally pegylated polypeptide. The method of obtaining the N-terminally pegylated preparation (i.e., separating this moiety from other monopegylated moieties if necessary) may be by purification of the N-terminally pegylated material from a population of pegylated polypeptide molecules. Selective polypeptides chemically modified at the N-terminus modification may be accomplished by reductive alkylation, which exploits differential reactivity of different types of primary amino groups (lysine versus the N-terminal) available for derivitization in a particular polypeptide. Under the appropriate reaction conditions, substantially selective derivitization of the polypeptide at the N-terminus with a carbonyl group containing polymer is achieved.

In any of the embodiments herein, a polypeptide of the present invention may be modified in its N-terminus. Examples of N-terminus modifications include an N-terminus methionine, N-terminus signal peptide, or a prosequence. An N-terminus methionine may be used for expression of a polypeptide recombinantly. A "signal sequence" or "presequence" refers to any sequence of amino acids bound to the N-terminal portion of a polypeptide herein (e.g., an amino acid sequence of SEQ ID NOs: 1-244, 248-249, or any homolog or analog thereof), which may participate in the secretion of the polypeptide. The term "prosequence" as used herein refers to a sequence of amino acids bound to the mature form of a polypeptide herein (e.g., an amino acid sequence of SEQ ID NOs: 1-244, 248-249, or any homolog or analog thereof), which when removed results in the appearance of the "mature" form of the polypeptide (e.g., an amino acid sequence of SEQ ID NOs: 1-244, 248-249, or any homolog or analog thereof). Preferably, a prosequence is autocleaved/ cleaved by naturally occurring enzymes, which are found at an area in which the mature polypeptide needs to be active.

In some embodiments a polypeptide herein includes one or more conservative substitutions. Such substitutions are selected from the Table I. Other known conserved substitutions may also be known to a person of ordinary skill in the art.

In some embodiments, a polypeptide of the present invention is modified to be more resistant to proteolysis. For example, a polypeptide comprising, consisting essentially of, or consisting of an amino acid sequence of (or encoded by) SEQ ID NOs: 1-244, 248-249, (any of the above with a methionine at the N-terminus) or any homolog, analog or fragment thereof may include one or more peptide bonds in which the —CONH— peptide bond is modified and replaced by a non-cleavable bond, e.g., a ($CH_2NH$) reduced bond, a (NHCO) retro inverso bond, a ($CH_2$—O) methylene-oxy bond, a ($CH_2$—S) thiomethylene bond, a ($CH_2CH_2$) carba bond, a (CO—$CH_2$) cetomethylene bond, a (CHOH—$CH_2$) hydroxyethylene bond), a (N—N) bound, a E-alkene bond or also a —CH—CH— double bond.

In some embodiments, a polypeptide sequence herein is constructed in its reverse sequence to prevent degradation. Examples of reverse sequence include those of SEQ ID NO: SEQ ID NOs: 153-244.

2. Nucleic Acids

The present invention also provides for a nucleic acid that encodes any of the polypeptides herein. For example, in some embodiments, the present invention relates to a nucleic acid sequence that encodes a polypeptide comprising, consisting essentially of, or consisting of an amino acid sequence selected from the group of SEQ ID NOs: 1-256, or selected from the group of SEQ ID NOs: 1-244, 248-249, or selected from the group of SEQ ID NOs SEQ ID NOs: 1-14 or 50-244, 248-249, or selected from the group of SEQ ID NOs: 1, 2, and 15 or more preferably SEQ ID NO: 1 (and any of the above with a methionine at the N-terminus) or a fragment, homolog, or analog thereof.

For example, the present invention provides for a polynucleotide sequence comprising, consisting essentially of, or consisting of the following sequence: [SEQ ID NO: 251: ttt ctg ccc tca]; SEQ ID NO: 252: ttt ctg ccc tca gaa ttt gga gta gac gta gac aga] or other nucleic acid sequence that encodes a peptide of the invention including all nucleic acid sequences permitted under codon degeneracy which is the divergence in the genetic code which permits variation of nucleotide sequence without effecting the amino acid sequence of an encoded polypeptide. Accordingly, the instant invention relates to any nucleic acid sequence that encodes all or a substantial portion of the amino acid sequences set forth herein.

Preferably any of the nucleotide sequences herein are preferably isolated and/or purified.

The present invention also includes recombinant constructs comprising one or more of the nucleotide sequences described herein. Such constructs comprise a vector, such as a plasmid or viral vector, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, *Molecular Cloning: A Laboratory Manual*, Cold Spring Harbor Press).

Examples of such expression vectors include chromosomal, nonchromosomal and synthetic DNA sequences, e.g., derivatives of or Simian virus 40 (SV40); bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides herein is inserted into an appropriate restriction endonuclease site(s) by procedures known in the art. Such procedures and related sub-cloning procedures are deemed to be within the scope of those skilled in the art.

The nucleic acid sequence in the expression vector is preferably operatively linked to an appropriate transcription control sequence (promoter) to direct mRNA synthesis. Examples of such promoters include: the retroviral long terminal (LTR) or SV40 promoter, the *E. coli* lac or trp promoter, the phage lambda PL promoter, and other promoters known to control expression of genes in prokaryotic or eukaryotic cells or their viruses. The expression vector also contains a ribosome binding site for translation initiation, and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

The vector containing the appropriate nucleic acid sequences as described above, as well as an appropriate promoter or control sequence, may be employed to transform an appropriate host to permit the host to express the peptides herein (e.g., SEQ ID NOs: 1-256 more preferably SEQ ID NOs: 1-24, 50-244, and 248-249, or more preferably SEQ ID NOs: 1-2, or more preferably SEQ ID NO: 1). Such vectors can be used in gene therapy.

Examples of appropriate expression hosts include: bacterial cells, such as *E. coli, Streptomyces, Salmonella typhimurium*; fungal cells, such as yeast; insect cells such as *Drosophila* and *Spodoptera frugiperda* (Sf9); animal cells such as CHO, COS, HEK 293 or Bowes melanoma; adenoviruses; plant cells, etc. The selection of an appropriate host is deemed to be within the scope of those skilled in the art from the teachings herein. The invention is not limited by the host cells employed.

Thus, in some embodiment, the present invention relates to methods for producing an analgesic peptide by transfecting a host cell with an expression vector comprising a nucleotide sequence that encodes a peptide comprising, consisting essentially of, or consisting of an amino acid sequence of (or encoded by) SEQ ID NOs: 1-244, 248-249, or any of the above with a methionine at the N-terminal, or any analgesic fragment thereof, or any homolog or analog thereof. Such host cells are then cultured under a suitable condition, which allows for the expression of such peptides.

The present invention further contemplates gene therapy using nucleic acids encoding one or more of the polypeptides herein (e.g., SEQ ID NOs: 1-256 more preferably SEQ ID NOs: 1-24, 50-244, and 248-249, or more preferably SEQ ID NOs: 1-2, or more preferably SEQ ID NO: 1) or an analog or homolog thereof. Preferably, such gene therapy is targeted. Targeted gene therapy involves the use of vectors (organ- and tumor-homing peptides) that are targeted to specific organs or tissues after systemic administration. The vector consisted of a covalent conjugate of avidin and a monoclonal antibody to a receptor. For example, for delivery to the brain, a chimeric peptide had been monobiotinylated, to a drug transport vector. The vector consisted of a covalent conjugate of avidin and the OX26 monoclonal antibody to the transferrin receptor. Owing to the high concentration of transferrin receptors on brain capillary OX26 targets brain and undergoes receptor-mediated transcytosis through the blood-brain barrier (Bickel et al., 1993, Proc. Nat. Acad. Sci. 90:2618-2622). Another example is vector-mediated delivery of opioid peptides to the brain (NIDA Res Monogr. 1995, 154:28-46).

In some embodiments, such nucleic acids are used to create a transgenic plant or animal, wherein the transgenic plant or animal is transgenic for a polynucleotide of the present invention and expresses a polypeptide of the present invention. For introducing a nucleic acid encoding one or more of the peptides herein into a plant cell, introduction can be carried out by conventional gene engineering techniques, for example, *Agrobacterium* infection, electroporation into protoplasts, particle gun methods, and the like. In some embodiments, the nucleic acids above are introduced along with a second nucleic acid sequence or gene. In some embodiments, the second nucleic acid sequence can act as a promoter, etc.

Preferably, the nucleic acid that is introduced into a plant cell is integrated into a vector having a selection marker gene. For example, the nucleic acids encoding SEQ ID NOs: 1-256 more preferably SEQ ID NOs: 1-24, 50-244, and 248-249, or more preferably SEQ ID NOs: 1-2, or more preferably SEQ ID NO: 1, or a homolog or analog thereof can be integrated into one of such vectors (e.g., pGEM-T and pBIN binary vectors). The vectors are then introduced into a chromosome of a plant cell by homologous recombination (Fraley et al., 1983, Proc. Natl. Acad. Sci. USA, 80; 4803). Plant cells expressing the nucleic acids can then be selected. Alternatively, the nucleic acids can be introduced into a plant cell in a vector that it is operably linked to a promoter and optionally a terminator both of which can function in the plant cell.

Non-limiting examples of promoters that can function in a plant cell include constitutive promoters derived from T-DNA such as nopaline synthase gene promoter, octopine synthase gene promoter, etc., promoters derived from plant viruses such as 19S and 35S promoters derived from cauliflower mosaic virus, etc., inductive promoters such as phenylalanine ammonia-lyase gene promoter, chalcone synthase gene promoter, pathogenesis-related polypeptide gene promoter, etc., and the like.

Non-limiting examples of terminators that can function in a plant cell include terminators derived from T-DNA such as nopaline synthase terminator, terminators derived from plant viruses such as terminators derived from garlic viruses GV1, GV2, and the like.

Plant cells into which such nucleic acids are introduced include plant tissues, whole plants, cultured cells, seeds and the like. Examples of the plant species into which the genes are introduced include dicotyledones such as tobacco, cotton, rapeseed, sugar beet, *Arabidopsis thaliana*, canola, flax, sunflower, potato, alfalfa, lettuce, banana, soybean, pea, legume, pine, poplar, apple, grape, citrus fruits, nuts, etc.; and monocotyledones such as corn, rice, wheat, barley, rye, oat, sorghum, sugar cane, lawn, etc. The second gene may also be introduced into such plant cells.

The transformant plant cells expressing one or more of the polypeptides herein or homologs thereof can be obtained by culturing cells into which the gene is transferred in a selection culture medium corresponding to a selection marker joined to the locus on the gene, for example, a culture medium containing a cell growth inhibitor, or the like, and isolating a clone capable of growing in the culture medium. Further, the selection culture medium should also correspond to a selection marker joined to the locus of the second gene when the altered form of enzymatic activity is also present in the transformant plant cells. Alternatively, the above transformant plant cells can be selected by culturing plant cells into which the gene is introduced in a culture medium containing the weed control compound to which the resistance is given, and isolating clones capable of growing in the culture medium.

The plant expressing the desired peptide can be obtained from the transformant cells thus obtained by regenerating the whole plant according to a conventional plant cell culture method, for example, that described in *Plant Gene Manipulation Manual, Method for Producing Transgenic Plants,* 1996, UCHIMIYA, Kodansha Scientific). Thus, the transformed plants such as plant tissues, whole plants, cultured cells, seeds and the like can be obtained.

For example, rice and *Arabidopsis thaliana* expressing a gene encoding a desired peptide having the characteristics of having (i) anti-pyrogenic, (ii) anti-inflammatory, (iii) anti-neoplastic activity, or (iv) expressing resistance against pathogen, or (v) expressing developmental changes such as an increase in the number of flowers (e.g., SEQ ID NOs: 1-256 more preferably SEQ ID NOs: 1-24, 50-244, and 248-249, or more preferably SEQ ID NOs: 1-2, or more preferably SEQ ID NO: 1, or a homolog or analog thereof) can be obtained according to the method described in *Experimental Protocol of Model Plants, Rice and Mouse-Ear Cress Edition,* Chapter 4 (1996, Supervisors: Shimamoto and Okada, Shujun-sha), Further, according to the method, soybean expressing a gene encoding a desired peptide by introducing the gene into soybean adventitious embryo with a particle gun. Likewise, according to the method described by Fromm et al., 1990, Bio/Technol., 8:838, corn expressing the gene can be obtained by introducing the gene into adventitious embryo with a particle gun. Wheat expressing the gene by introducing the gene into sterile-cultured wheat immature scutellum with a particle gun according to a conventional method described by Takumi, 1995, J. Breeding Soc., 44: Extra, 1:57. Likewise, according to a conventional method described by Hagio et al., 1995, J. Breeding Soc., 44; Extra, 1:67, barley expressing the gene encoding the above polypeptide can be obtained by introducing the gene into sterile-cultured barley immature scutellum with a particle gun.

Another embodiment is directed to fragments of the correspondent nucleic acid sequences, or the complement thereof, which may find use as, for example, hybridization probes or as antisense oligonucleotides. Such nucleic acid fragments are usually at least about 10 nucleotides in length, preferably at least about 20 nucleotides in length, preferably at least about 30 nucleotides in length, more preferably at least about 40 nucleotides in length, yet more preferably at least about 50 nucleotides in length, yet more, wherein in this context the term "about" means the referenced nucleotide sequence length plus or minus 10% of that referenced length.

In some embodiments, the present invention relates to methods for isolating a gene or gene fragment encoding a peptide of the invention (SEQ ID NOs: 1-256 more preferably SEQ ID NOs: 1-24, 50-244, and 248-249, or more preferably SEQ ID NOs: 1-2, or more preferably SEQ ID NO: 1, or a homolog or analog thereof) and homologs or analogs thereof from various organisms. Such gene or gene fragment can have (i) anti-pyrogenic, (ii) anti-inflammatory, (iii) anti-neoplastic activity, or (iv) expressing resistance against pathogen, or (v) expressing developmental changes such as an increase in the number of flowers. Such gene or gene fragment can be identified by performing PCR using genomic DNA or cDNA of an organism having the desired gene as a template and primers produced on the basis of nucleotide sequences corresponding to those about the N- and C-termini of the polypeptide to amplify the desired gene. Further, genes encoding a peptide can be obtained different organisms (e.g., a clone, a plant, an animal, etc.). For example, first, a cDNA library is constructed by obtaining mRNA from an organism and synthesizing cDNA by using the mRNA as template with reverse transcriptase and integrating the cDNA into a phage vector such as ZAP II, etc. or a plasmid vector such as pUC, etc. The cDNA library may be introduced into *Escherichia coli* followed by subjecting a complementation test to select clones containing the desired gene derived from the desired organism. Further, for amplifying a DNA fragment containing at least a part of the desired gene, PCR can be carried out by using the above-constructed cDNA library as a template and primers designed and synthesized on the basis of nucleotide sequences of the peptide. Screening of the cDNA library can be carried out by using the DNA fragment thus obtained as a probe to select positive clones. The desired gene, i.e., a gene encoding a peptide substantially having at least one characteristics of (i) to, (v), can be confirmed by determination of the nucleotide sequence of the selected clone.

3. Antibodies

In another embodiment, the invention provides for antibodies that specifically bind to any of the polypeptides herein. For example, the present invention contemplates an antibody that specifically binds to a peptide of having an amino acid sequence comprising, consisting essentially of, or consisting of an amino acid sequence of SEQ ID NOs: 1-244, 248-249, or more preferably SEQ ID NOs: 1-14 and 50-244, or more preferably SEQ ID NOs: 1-2 or more preferably SEQ ID NO: 1, or any of the above with a methionine at the N-terminus, or any fragment, homolog, or analog thereof. The term "antibodies" is meant to include polyclonal antibodies, monoclonal antibodies, fragments thereof such as F(ab')$_2$, and Fab fragments, as well as any recombinantly produced binding-partners.

Antibody can be prepared by conventional methods, e.g. by immunization of a human or of an animal, such as, for example, mouse, rat, guinea pig, rabbit, horse, sheep, goat, chicken (see also Messerschmid, 1996, BIOforum, 11:500-502), and subsequent isolation of the antiserum; or by establishing hybridoma cells and subsequent purification of the secreted antibodies; or by cloning and expression of the nucleotide sequences, or modified versions thereof, which encode the amino acid sequences which are responsible for the binding of the natural antibody to the antigen and/or hapten. Antibodies of the invention are in particular those antibodies which bind to a polypeptide comprising, consisting essentially of, or consisting of an amino acid selected from the group consisting of: SEQ ID NOs: 1-256, more preferably selected from the group consisting of SEQ ID NOs: 1-24, 50-244, and 248-29, more preferably selected from the group consisting of SEQ ID NOs: 1-24, 50-163, 248-249, more preferably selected from the group consisting of SEQ ID NOs: 1-2, or more preferably SEQ ID NO: 1. In some embodiments, such polypeptide has less than 100 amino acid residues, 90, 80, 70, 60, 50, 40, 30, 20, 10, 9, 8, 7, 6, 5, or 4 amino acid residues. In some embodiments, such polypeptide has between 4-100, 4-50, 4-40, 4-30, or 4-20 amino acid residues. Preferably, such antibody selectively binds to the amino acid sequence Phe-Leu-Pro-Ser-Glu-Phe-Gly-Val-Asp-Val-Asp-Arg (SEQ ID NO: 2) or more preferably amino acid sequence Phe-Leu-Pro-Ser (SEQ ID NO: 1)

The antibodies herein preferably specifically bind with a $K_a$ of greater than or equal to about $10^4$ M$^{-1}$, preferably about $10^5$ M$^{-1}$, more preferably about $10^6$ M$^{-1}$ and still more preferably about $10^7$ M$^{-1}$. Affinities of binding-partners or antibodies can be readily determined using conventional techniques, for example those described by Scatchard et al., 1949 (Ann. N.Y. Acad. Sci. 51:660) or, by surface plasmon resonance described by Wolff et al., 1993 (Cancer Res. 53:2560; BIAcore/Biosensor, Piscataway, N.J.), which are incorporated herein by reference for all purposes.

Polyclonal antibodies can be readily generated from a variety of sources, for example, horses, cows, goats, sheep, dogs, chickens, rabbits, mice or rats, using procedures that are well known in the art. In general, an isolated polypeptide of the invention (e.g., a polypeptide comprising, consisting essentially of, or consisting of an amino acid sequence of (or encoded by) SEQ ID NOs: 1-244, 248-249, or any of the above with an N-terminal methionine) that is appropriately conjugated, is administered to the host animal typically through parenteral injection. The immunogenicity of the polypeptide may be enhanced through the use of an adjuvant, for example, Freund's complete or incomplete adjuvant. Following booster immunizations, small samples of serum are collected and tested for reactivity to the polypeptide. Examples of various assays useful for such determination include those described in *Antibodies: A Laboratory Manual*, Harlow and Lane (eds.), Cold Spring Harbor Laboratory Press, 1988; as well as procedures such as countercurrent immuno-electrophoresis (CIEP), radioimmunoassay (RIA), radioimmunoprecipitation, enzyme-linked immunosorbent assays (ELISA), dot blot assays, and sandwich assays, see, e.g., U.S. Pat. Nos. 4,376,110 and 4,486,530, or other similar assays known in the art.

Monoclonal antibodies specific for a desired polypeptide antigen (such as the peptides described herein) may be readily prepared using well-known procedures, see for example, the procedures described in *Current Protocols in Immunolog* (Wiley & Sons, NY, Coligan et al., eds., 1994; U.S. Pat. Nos. RE 32,011, 4,902,614, 4,543,439 and 4,411,993; *Monoclonal Antibodies, Hybridomas: A New Dimension in Biological Analyses*, 1980, Plenum Press, Kennett et al., eds.). Briefly, the host animals, such as mice are injected intraperitoneally at least once, and preferably at least twice at about three-week intervals with isolated and purified polypeptide herein (e.g., a polypeptide comprising, consisting essentially of, or consisting of an amino acid sequence of (or encoded by) SEQ ID NOs: 1-244, 248-249, or, conjugated polypeptide herein, optionally in the presence of adjuvant. Mouse sera are then assayed by conventional dot blot technique or antibody capture (ABC) to determine which animal is most suitable as a source of splenocytes for fusion to a myeloma partner cell-line. Approximately 2-3 weeks later, the mice are given an intravenous boost of the polypeptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, PEG. The cell suspension containing fused cells is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as, $^{125}$I-conjugated polypeptide (e.g., a polypeptide comprising, consisting essentially of, or consisting an amino acid sequence of (or encoded by) SEQ ID NOs: 1-244, 248-249, or any of the above with an N-terminal methionine) is added to each well followed by incubation. Positive wells can be subsequently detected by autoradiography. Positive clones can be grown in bulk culture and supernatants are subsequently purified over a Polypeptide A column (Pharmacia).

The monoclonal antibodies of the invention can be produced using alternative techniques, such as those described by Alting-Mees et al., 1990 (*Monoclonal Antibody Expression Libraries: A Rapid Alternative to Hybridomas, Strategies*, Mol. Biol. 3:1-2469). Similarly, binding partners can be constructed using recombinant DNA techniques to incorporate the variable regions of a gene that encodes a specific binding antibody. Larrick et al. describe such technique in Biotechnol, 7:394, 1989.

Other types of antibodies may be produced using the information provided herein in conjunction with the state of knowledge in the art. For example, antibodies that have been engineered to contain elements of human antibodies that are capable of specifically binding any of the peptide or to a polypeptide containing the peptide sequence herein are also encompassed by the invention. An additional method for selecting antibodies that specifically bind to a polypeptide, peptide or fragment thereof is by phage display, e.g., Winter et al., 1994, Annu. Rev. Immunol. 12: 433; Burton et al., 1994, Adv. Immunol. 57:191. Human or murine immunoglobulin variable region gene combinatorial libraries may be created in phage vectors that can be screened to select Ig fragments (Fab, Fv, sFv, or multimers thereof) that bind specifically to a polypeptide, peptide, or fragment thereof. See, e.g., U.S. Pat. No. 5,223,409; Huse et al., 1989, Science: 1275; Kang et al., 1991 Proc. Natl. Acad. Sci. USA 88:4363; Hoogenboom et al., 1992, J. Molec. Biol. 227:381; Schlebusch et al., 1997, Hybridoma 16:47, and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat polypeptide, for instance, gene III or gene VIII of M13, to create an M13 fusion polypeptide. A fusion polypeptide may be a fusion of the coat polypeptide with the light chain variable region domain and/or with the heavy chain variable region domain. Once isolated and purified, the antibodies may be used to detect the presence of a polypeptide, or a peptide of the present invention in a sample using established assay protocols. Further, the antibodies of the invention may be used therapeutically to bind to the peptides of the invention and alter their activity in vivo.

Formulations

Any of the composition herein may be formulated into pharmaceutical, veterinary, cosmetic and/or agricultural formulations for administration to an organism.

Typically such formulations will include one or more acceptable carriers, excipients, or diluents. Pharmaceutically acceptable carriers for therapeutic use are well known in the pharmaceutical art, and are described, e.g., in *Remington's Pharmaceutical Sciences*, Gennaro, A R, ed., 20th edition, 2000: Williams and Wilkins Pa., USA. which is incorporate herein by reference for all purposes. Agriculturally acceptable carriers for therapeutic or prophylactic treatment of plants are also known in the art. Cosmetic and veterinary excipients are also known in the art.

For example, the compositions herein may be combined with one or more natural or synthetic, organic or inorganic material to facilitate their application into the plant. Such a carrier will generally be inert and acceptable in agriculture. Such carrier can be solid (e.g., clays, natural or synthetic silicates, silica, resins, waxes, or solid fertilizers) or liquid (e.g., water, alcohols, ketones, petroleum fractions, aromatic or paraffinic hydrocarbons, chlorinated hydrocarbons, or liquefied gases).

A pharmaceutical or agricultural formulation can also contain any kind of other compatible ingredients such as, for example, protective colloids, adhesives, thickening agents, thixotropic agents, penetrating agents, stabilizing agents, sequestering agents, fertilizers, anti-freeze agents, repellents, color additives, corrosion inhibitors, water-repelling agents, UV-stabilizers, pigments, dyes or polymers.

In some embodiments, the compositions herein may be formulated as a salt and be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5 that is combined with buffer prior to use. After pharmaceutically and physiologically acceptable compositions have been prepared, they can be placed in an appropriate container and labeled for treatment of an indicated condition.

While any suitable carrier known may be employed in a pharmaceutical formulation of this invention, the type of carrier will vary depending on the mode of administration and whether a sustained release is desired. Routes of delivery may include oral, inhaled, buccal, intranasal, and transdermal routes, as well as novel delivery systems such as the protective liposomes for oral delivery of peptides.

For agricultural uses, formulations are preferably in a liquid or spray or any other dry formulations.

For parenteral administration, such as subcutaneous injection, the carrier preferably comprises water, saline, alcohol, a fat, a wax or a buffer.

For oral administration, a carrier preferably comprises of carbohydrate or polypeptide fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and polypeptides such as gelatin and collagen. If desired, disintegrating or solubilizing agents may be added, such as the cross-linked polyvinyl pyrrolidone, agar, alginic acid, or a salt thereof, such as sodium alginate. If desirable, the drug can be delivered in nanocapsules that would protect against proteolysis by proteases. Such carriers enable the compositions herein to be formulated as tablets, pills, dragees, capsules, liquids, gels, syrups, slurries, suspensions, and the like, for ingestion by the patient. Pharmaceutical preparations for oral use can be obtained through a combination of active compounds with solid excipient, suiting mixture is optionally grinding, and processing the mixture of granules, after adding suitable auxiliaries, if desired, to obtain tablets or dragee cores. As the composition may be peptide, such peptides are preferably put into a liposomal formulation to avoid degradation.

Preferably the pharmaceutical formulations herein are administration by intravenous injection or by local applications (e.g., topical or subdermal).

Formulations for topical administration can use a carrier that is a solution, emulsion, and ointment or gel base. The base, for example, may comprise one or more of the following: petrolatum, lanolin, PEGs, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 μm.

Pharmaceutical compositions may also contain diluents such as buffers, antioxidants such as ascorbic acid, low molecular weight (less than about 10 residues) polypeptides, polypeptides, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product is formulated as a lyophilizate using appropriate excipient solutions (e.g., sucrose) as diluents.

Pharmaceutically acceptable formulations include compositions wherein the active ingredients (e.g., a polypeptide comprising of, consisting essentially of, or consisting of an amino acid sequence of (or encoded by) SEQ ID NOs: 1-244, 248-249, or any analog, or homolog thereof) are contained in an effective dose to achieve the intended purpose. The determination of an effective amount or dosage is well within the capability of those skilled in the art. Typically, an effective dose of a polypeptide of the present invention (e.g., a polypeptide comprising of, consisting essentially of, or consisting of an amino acid sequence of (or encoded by) SEQ ID NOs: 1-244, 248-249, or any analog or homolog thereof) for systemic administration is between about 0.001 μg to about 100 g, or more preferably between about 0.01 μg to about 50 g, or more preferably between about 0.1 μg to about 1 g, or more preferably between about 1 mg to about 500 mg per dose. For topical administration, the compositions herein may be delivered at dosage up to about 99, 95, 90, 80, 70, 60, 50, 40, or 30% w/w of the composition.

In some embodiments, the therapeutic effective dosages of SEQ ID NOs: 1-256 are the serum concentrations that in the range of 1-1000 mg/L, 5-500 mg/L, or 10-100 mg/L, or 10-20 mg/L or the active ingredient.

Any of the compositions herein may be co-formulated or co-administered with a second therapeutic agent. Examples of therapeutic agents include, but are not limited to, analgesic, antipyretic medicaments (fever reducers), anesthetics, anti-rheumatic agents, anti-inflammatory agents, antidepressants, anti-neoplastic agents, antimicrobial agents (e.g., antibiotics, antiviral agents, and antifungal agents), pesticides, herbicides, angiogenic agents, anti-angiogenic agents, inhibitors of neurotransmitters or neurotransmitters, any agent known to treat neurodegenerative conditions and wound healing, and combinations thereof.

The concentration of an active ingredient in the composition of the present invention, as applied to plants is preferably within the range of 0.01 to 30.0% by weight, especially 0.1 to 30% % by weight. In a primary composition, the amount of active ingredient can vary widely and can be, for example, from 5 to 95% by weight of the composition.

For any of the compositions herein, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans. Those of ordinary skill in the art are well able to extrapolate from one model (be it an in vitro or an in vivo model). A therapeutically effective dose refers to that amount of active ingredient, for example a polypeptide comprising of, consisting essentially of, or consisting of an amino acid sequence of (or encoded by) SEQ ID NOs: 1-244, and 248-249, or any fragment, analog, or homolog thereof, which ameliorates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutically and physiologically acceptable compositions, which exhibit large therapeutic indices, are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The practitioner, in light of factors related to the subject that requires treatment, will determine the exact dosage. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Long-acting pharmaceutically and physiologically acceptable compositions maybe administered every 3 to 4 days, every week, or once every two weeks depending on half-life and clearance rate of the particular formulation.

Normal dosage amounts may vary from 0.001 μg to 100 g, up to a total dose of about 1 g, depending upon the route of administration. Guidance as to particular dosages and methods of delivery is provided in the literature and generally available to practitioners in the art. Those skilled in the art will employ different formulations for nucleotides than for polypeptides or their inhibitors. Similarly, delivery of polynucleotides or polypeptides will be specific to particular cells, cell types, organism being treated, conditions, locations, etc.

For example, for the prevention or treatment of pain, the appropriate dosage of an anti-pain medicament will depend on the type of condition to be treated, as defined above, the severity and course of the disease, whether the agent is administered for preventive or therapeutic purposes or, as a combination with other drugs, previous therapy, the patient's clinical history and response to the agent, and the discretion of the attending physician. The agent is suitably administered to the patient at one time or over a series of treatments.

Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" in *Toxicokinetics and New Drug Development*, Yacobi et al., eds., Pergamon Press, New York 1989, pp. 42-96. For example, depending on the type and severity of the disease, about 0.001 μg/kg to 1000 mg/kg of a therapeutic agent is an initial candidate dosage for administration to the patient, whether, for example, by one or more separate administrations, or by continuous infusion. A typical daily dosage might range from about 1 g/kg to 100 g/kg or more, depending on the factors mentioned above. For local administration or topical administration lower dosage may be required. For repeated administrations over several days or longer, depending on the condition, the treatment is sustained until a desired suppression of disease symptoms occurs. However, other dosage regimens may be useful. The progress of this therapy is easily monitored by conventional techniques and assays. Guidance as to particular dosages and methods of delivery is provided in the literature; see, for example, U.S. Pat. Nos. 4,657,760; 5,206,344; or U.S. Pat. No. 5,225,212. It is anticipated that different formulations will be effective for different treatment compounds and different disorders, that administration targeting one organ or tissue, for example, may necessitate delivery in a manner different from that to another organ or tissue.

The compositions may be administered in the form of a solid, liquid, gel or gas (aerosol). The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain, in addition to the compositions herein one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Injectable formulations of the compositions herein are preferably sterile. Means for achieving sterility are well known in the art.

For delivery to the dermis and/or epithelium, dermal patches and delivery systems, utilizing active or passive transdermal delivery carriers may be prepared suing well known methods and materials, including, for example, microporous membranes, silicon polymers and diffusion matrixes. Such materials and methods are described, for example, in: *Remington's Pharmaceutical Sciences*, supra.

For use in plants, the compositions of the invention are generally applied to seeds, plants or their habitat. Thus, the compositions herein can be applied directly to the soil before, at or after drilling so that the presence of active compound in the soil can control the growth of pathogens, which may attack the seeds. When the soil is treated directly with a composition herein, it can be applied in any manner which allows it to be intimately mixed with the soil, e.g., by spraying, by broadcasting a solid form of granules, or by applying the active ingredient at the same time as drilling by inserting it in the same drill as the seeds. A suitable application rate is within the range of from 0.005 to 1000 g per hectare, more preferably from 0.10 to 500 g per hectare.

Alternatively, the active compounds can be applied directly to a plant by, for example, spraying or dusting either at the time when a pathogen has begun to appear on the plant or before the appearance of a pathogen as a protective measure. In both such cases the preferred mode of application is by foliar spraying. It is generally important to obtain good control of pathogens in the early stages of plant growth, as this is the time when the plant can be most severely damaged.

The spray or dust can further contain a pre- or post-emergence herbicide if this is thought necessary. Sometimes, it is practicable to treat the roots, bulbs, tubers or other vegetative propagule of a plant before or during planting, for example, by dipping the roots in a suitable liquid or solid composition. When the active compound is applied directly to the plant a suitable rate of application is from 0.002 to 5 kg per hectare, preferably from 0.005 to 1 kg per hectare, or more preferably from 0.01 to 0.05 kg per hectare.

Conditions Affecting Animals and Plants

In some aspects, the present invention relates to uses of compositions such as the peptides disclosed herein (Table V) for modulating, preventing, or treating condition(s) in an organism. Such organisms can be animals and/or plants. Animals are preferably domesticated animals or humans. Plants are preferably crops such as wheat, barley, rice, corn, sugar, or soy; vegetables or fruits, such as apples, pears, citrus fruits, berries and nuts; and/or flowering plants such as roses, gardenias, orchids, carnations, bird of paradise, etc. But other plants or parts of plants are also contemplated herein (e.g., trees for lumber, such as fir, redwoods, pine, etc.)

The conditions that are modulated, prevented, or treated by the compositions herein can be broadly classified as metabolic or mitochondrial conditions. More specifically, such conditions are e.g., thermogenic or pyrogenic conditions. Such conditions can be associated with, for example, pain, temperature regulation, inflammation, neoplastic growth (e.g., cancer), innate immune response activation and ability to fight parasites and pathogens, skin and dermatological conditions, diabetes related disorders, wound healing, undesirable drug side effects, and neurological and neurodegenerative conditions.

Such conditions can occur in a cell, group of cells, or an entire organism to be treated herein.

1. Pain.

In one aspect the present invention relates to treatment of pain. Examples of pain conditions contemplated by the invention include, but are not limited to, headaches (e.g., trigeminal neuralgia, sinusitis, cluster headaches, migraines, etc.), low back pain, cancer pain, arthritis pain, muscle spasm pain (muscle cramps), bone pain, pain resulting from burns, pain associated with bumps, pain associated with bruises, inflammatory pain (from an infection or arthritic disorder), pain from obstructions, myofascial pain, pain from nerve trauma (dystrophy/causalgia), phantom limb pain, entrapment neuropathy (e.g., carpal tunnel syndrome), peripheral neuropathy, and pain from wounds, e.g., surgical, accidental, or self-inflicted wounds.

The pathophysiology of pain can be broadly divided into three categories: (i) nociceptive pain, (ii) neuropathic pain, and (iii) idiopathic pain. (Willis, W. D., 1985, *The Pain System. The Neural Basis of Nociceptive Transmission in the Mammalian Nervous System. Pain and Headache*, vol. 8, Gildenberg P L (Ed.) Karger Publishers, New York).

Nociceptive pain is the result of receptor stimulation by tissue injury. It involves the normal activation of the nociceptive system by noxious stimuli. Examples of nociceptive pain include sprains, bone fractures, burns, bumps, bruises, inflammation (from an infection or arthritic disorder), obstructions, myofascial pain (which may indicate abnormal muscle stresses) headaches, low back pain, cancer pain, and arthritis pain. In some embodiments, the compositions herein are used to prevent or treat nociceptive pain. Preferably, such compositions are an amino acid sequence of (or encoded by) SEQ ID NOs: 1-244, 248-249. In some embodiments, second therapeutic agents such as NSAIDs (Non-Steroidal Anti-Inflammatory Drugs), and/or opioids can be used in combination with the compositions herein to treat nociceptive pain.

Thus, in one aspect, the present invention relates to uses of the compounds herein for treating nociceptive pain. Such methods involve administering one or more of the compositions herein to a subject suffering or susceptible of suffering nociceptive pain. Such composition preferably a polypeptide comprising, consisting essentially of, or consisting of an amino acid sequence selected from the group of SEQ ID NOs: 1-244, 248-249, or from the group of SEQ ID NOs: 1-14, 50-152, and 248-249 or SEQ ID NOs: 1-2 or SEQ ID NO: 1. In one embodiment, such composition comprises a nucleic acid sequence that encodes a polypeptide comprising, consisting essentially of, or consisting of an amino acid sequence selected from the group of SEQ ID NOs: 1-244, 248-249, or from the group of SEQ ID NOs: 1-14, 50-152, and 248-249 or SEQ ID NOs: 1-2 or SEQ ID NO: 1. In one embodiment, such composition comprises an antibody that specifically binds a polypeptide comprising, consisting essentially of, or consisting of an amino acid sequence selected from the group of SEQ ID NOs: 1-244, 248-249, or from the group of SEQ ID NOs: 1-14 50-152, and 248-249 or SEQ ID NOs: 1-2 or SEQ ID NO: 1.

The second category of pain, neuropathic pain, is the result of an injury or malfunction in the peripheral or central nervous system. Examples of neuropathic pain include post herpetic (or post-shingles) neuralgia, reflex sympathetic dystrophy/causalgia (nerve trauma), components of cancer pain, phantom limb pain, entrapment neuropathy (e.g. carpal tunnel syndrome), and peripheral neuropathy most commonly caused by diabetes or chronic alcohol use.

Neuropathic pain is often triggered by an injury, but this injury may or may not involve actual damage to the nervous system. For example, nerves can be infiltrated or compressed by tumors, strangulated by scar tissue, or inflamed by infection, which may cause neuropathic pain. Neuropathic pain may persist for months or years beyond the apparent healing of any damaged tissues. Therefore, neuropathic pain is frequently chronic, not fully reversible, and tends to have a less robust response to treatment with opioids, but may respond to drugs such as anticonvulsants (carbamazepine and valproic acid, and gabapentin) and neuromodulating drugs (including tricyclic antidepressants, such as amitriptyline, imipramine, and desipramine).

The present invention contemplates uses of the compositions herein for treatment of neuropathic pain. In particular, the present invention includes methods for treating neuropathic pain in a subject by administering one or more of the compositions herein to the subject in a therapeutically effective amount to treat or prevent neuropathic pain. In preferred embodiment, the composition herein used to treat neuropathic pain preferably comprise or consist essentially or consisting of a polypeptide comprising, consisting essentially of, or consisting of an amino acid sequence selected from the group of SEQ ID NO: 1-2, or from the group of SEQ ID NOs: 1-14 and 50-244, or SEQ ID NOs: 1-2 or SEQ ID NO: 1. In one embodiment, such composition comprises a nucleic acid sequence that encodes a polypeptide comprising, consisting essentially of, or consisting of an amino acid sequence selected from the group of SEQ ID NOs: 1-244, 248-249, or from the group of SEQ ID NOs: 1-14 and 50-244, or SEQ ID NOs: 1-2 or SEQ ID NO: 1. In one embodiment, such composition comprises an antibody that specifically binds a polypeptide comprising, consisting essentially of, or consisting of an amino acid sequence selected from the group of SEQ ID NO: 1-244, 248-249, or from the group of SEQ ID NOs: 1-14 and 50-244, or SEQ ID NOs: 1-2 or SEQ ID NO: 1.

The third category of pain, idiopathic pain, is a diagnosis of exclusion in which a patient suffers pain for longer than 6 months for which there is no physical cause and no specific mental disorder. Examples of idiopathic pain include, but are not limited to, arthritis, fibromyalgia, chronic fatigue syndrome, irritable bowel syndrome, interstitial cystitis, vulvadynia, carpal tunnel syndrome, etc.

In one aspect, the present invention relates to uses of the compounds herein for treating idiopathic pain. Such methods involve administering one or more of the compositions herein to a subject suffering or susceptible of suffering idiopathic pain. Such composition preferably include a polypeptide comprising, consisting essentially of, or consisting of an amino acid sequence selected from the group of SEQ ID NO: 1-244, 248-249, or from the group of SEQ ID NOs: 1-14 and 50-244, or SEQ ID NOs: 1-2 or SEQ ID NO: 1. In one embodiment, such composition comprises a nucleic acid sequence that encodes a polypeptide comprising, consisting essentially of, or consisting of an amino acid sequence selected from the group of SEQ ID NOs: 1-244, 248-249, or from the group of SEQ ID NOs: 1-14 and 50-244, or SEQ ID NOs: 1-2, or SEQ ID NO: 1. In one embodiment, such composition comprises an antibody that specifically binds a polypeptide comprising, consisting essentially of, or consisting of an amino acid sequence selected from the group of SEQ ID NOs: 1-244, 248-249, or from the group of SEQ ID NOs: 1-14 and 50-244, or SEQ ID NOs: 1-2 or SEQ ID NO: 1.

Any of the compositions herein can be administered either singly or in combination with a second therapeutic agent such as an analgesic pain reliever or anti-inflammatory. In some embodiments, the second therapeutic agent is co-formulated with one or more of the compositions herein.

According to the National Drug Classification (NDC), analgesics can be categorized in to the following group: general analgesic, narcotic analgesic, non-narcotic analgesic, anti-arthritics, anti-migraine/headache, central pain syndrome, NSAID, anti-pyretic, and anti-menstrual pain products. These categories can be combined into broader categories of analgesics entitled: narcotic analgesics, non-narcotic analgesics, and NSAIDs.

The present invention relates to a pharmaceutical formulation comprising the combination of the polypeptides herein with one or more analgesic agents selected from the group consisting of general analgesic, narcotic analgesic, non-narcotic analgesic, anti-arthritics, anti-migraine/headache, central pain syndrome, NSAID, anti-pyretic, and anti-menstrual pain products. The present invention also relates to a pharmaceutical formulation comprising the combination of the polypeptides herein with one or more analgesics selected from the group consisting of narcotic analgesics, non-narcotic analgesics, and NSAIDs. The present invention also relates to methods of treating a subject suffering from pain (e.g., nociceptive pain, neuropathic pain, and idiopathic pain) comprising administered to said subject the one or more compositions herein and the one or more analgesics described herein (either separately or in combination, as a co-formulation or in two separate formulations). Preferably the polypeptides comprise, consist essentially of, or consist of an amino acid sequence selected from the group of SEQ ID NOs: 1-14 and 50-244, or SEQ ID NOs: 1-2 or SEQ ID NO: 1.

Examples of narcotic analgesics include, but are not limited to, Alfentanil; Allylprodine; Alphaprodine; Amiphenazole, Anileridine, Benzoylhydrazone, Benzylmorphine, Benzitramide, Nor-Binaltorphimine, Bremazocine; Bupremorphine; Butorphanol (Stadol); Clonitazene; Codeine; CTOP; Cyclazocine; DAMGO; Desomorphine; Dextromoramide; Dezocine; Diampromide; Dihydrocodeine; Dihydrocodeine enol acetate; Dihydromorphine; Dimenoxadol; Dimepheptanol; Dimethylthiambutene; Dioxaphetyl Butyrate; Dipipanone; Diprenorphine; DPDPE; Eptazocine; Ethoheptazine; Ethylketocyclazocine; Ethylmethylthiambutene; Etonitazene; Etorphine; Fentanyl (Sublimaze, Duragesic); Hydrocodone; Hydromorphone (Dilaudid); Hydroxypethidine; Isomethadone; ketobemidone; Levorphanol; Levallorphan; Lofentanil; Loperamide; Meperidine (Demerol); Meptazinol; Metazocaine; Methadone (Dolophine); Metopon; Morphine (Roxanol); Myrophine; Nalbuphine; Nalmefene; Nalorphine; Naloxone; Naltrindole; Naltrexone; Narceine; Nicomorphine, Norlevorphanol; Normethadone; Normorphine; Norpipanone; Opium; Oxycodone (OxyContin); Oxymorphone; Papaveretum; Papaverine; Pentazocine; Phenadoxone; Phenazocine; Phenoperidine; Piminodine; Pirtramide; Proheptazine; Promedol; Propiram; Propoxyphene (Darvon); Remifentanil; Spiradoline; Sufentanil; Tilidine; U50,488; and U69,593. Some products are combination drugs; codeine/acetaminophen (APAP; Tylenol #3); hydrocodone/acetaminophen (Vicodin); Oxycodone/ASA (Percodan); oxycodone/APAP (Percocet); propoxyphene/ASA (Darvon Compound); propoxyphene/napsylate (Darvocet-N); hydrocodone/ibuprofen (Vicoprofen); pentazocine/naloxone (Talwin-Nx).

Examples of non-narcotic analgesics, include, but are not limited to, Acetaminophen (Paracetamol; Tylenol); aspirin (acetylsalicylic acid; Anacin, Ascriptin, Bayer, Bufferin, Ecotrin, Excedrin); Aminobenzoic Acid; Capsaicin (Zostrix and Zostrix-HP); Carbaspirin Calcium; Choline and Magnesium Salicylates (CMT, Tricosal, Trilisate); Choline Salicylate (Arthropan); Etanercept; Fluprednisolone; Gold sodium Thiomalate; Gold Sodium Thiosulfate; Hyaluronic Acid; Homomethyl Salicylate; Leflunomide; Magnesium Salicylate (Arthritab, Bayer Select, Doan's Pills, Magan, Mobidin, Mobogesic); Menthol; Methorexate; Octyl Salicylate; Oxyphenbutazone; Phenyl Salicylate; Phenylbutazone; Prednisolone; Salicylamide; Salsalate (Amigesic, Anaflex 750, Disalcid, Marthritic; Mono-Gesic, Salflex, Salsitab); Sodium Hyaluronate; Sodium Salicylate; o-Acetylsalicyloyl Chloride; Sodium Thiosalicylate (Thiocyl); Tramadol; Triamcinilone; Triethanolamine Salicylate (Trolamine); Zomepirac. Some products, such as Excedrin, are combination drugs (Excedrin is acetaminophen, ASA, and caffeine). Other non-narcotic gabapentin (Neurontin); lamotrigine and, anti-convulsants and tricyclic anti-depressants such as carbamazepine, pregabalin and duloxetine Examples of NSAIDS include, but are not limited to, Bromfenac Sodium; Celecoxib (Celebrex); Diclofenac Potassium (Cataflam); Diclofenac Sodium (Voltaren, Voltaren XR); Diclofenac Sodium with misoprostol (Arthrotec); Diflunisal (Dolobid); Etodolac (Lodine, Lodine XL); Etadolac; Fenoprofen calcium (Nalfon); Flurbiprofen (Ansaid); Ibuprofen (Motrin, Advil, Nuprin); Indomethacin (Indocin, Indocin SR); Ketoprofen (Actron, Orudis, Orudis KT, Oruvail); Meclofenamate Sodium (Meclomen); Mefenamic acid (Ponstel); Meloxicam (Mobic); Nabumetone (Relafen); Naproxen (Naprosyn, Naprelan, Alleve, Anaprox); Oxaprozin (Daypro); Piroxicam (Feldene); Piroxicam (Feldene); Rofecoxib (Vioxx); Sulindac (Clinoril); Suprofen; Tolmetin Sodium (Tolectin); Valdecoxib (Bextra).

Furthermore, there are various naturally occurring and synthetic opioids that can be used to treat pain. See Table II below.

TABLE II

List of opioid peptides

| Enkephalins | |
| --- | --- |
| [Leu]- enkephalin | YGGFL (SEQ ID NO: 15) |
| [Met]-enkephalin | YGGFM (SEQ ID NO: 16) |
| Rimorphin | YGGFLRRQFKVVT (SEQ ID NO: 248) |
| Leumorphin | KYPKRSSEVAGEGDGDSMGHEDLYKRY GGFLRRIRPKLKWDNQKRYGGFLRRQFK VVTRSQEDPNAYSGELFDA (SEQ ID NO: 249) |
| Endorphins | |
| α-Neoendorphin | YGGFLRKYPK (SEQ ID NO: 17) |
| β-Neoendorphin | YGGPLRKYP (SEQ ID NO: 18) |
| β-human-Endorphin | YGGFMTSEKSQTPLVTLFKNAIIKNAYKKGE (SEQ ID NO: 19) |
| α-human-Endorphin | YGGFMTSEKSQTPLVT (SEQ ID NO: 20) |
| Dynorphins | |
| Dynorphin A | YGGFLRRIRPKLKWDNQ (SEQ ID NO: 21) |
| Dynorphin B | YGGFLRRQFKVVT (SEQ ID NO: 22) |
| Endomorphins | |
| Endomorphin-1 | YPTF (SEQ ID NO: 23) |
| Endomorphin-2 | YPFF (SEQ ID NO: 24) |
| Synthetic peptides | |
| [D-Ala$^2$, N-Me-Phe$^4$, Gly$^5$-ol]- enkephalin (DAMGO; DAGO) | [Tyr-D-Ala-Gly-N-Methyl-Phe-Gly-ol (SEQ ID NO: 25) |
| D-Pen$^{2,5}$]-enkephalin (DPDPE) | [Tyr-D-Pen-Gly-Phe-D-Pen (SEQ ID NO: 26) |
| D-Pen$^{2,5}$]-enkephalin (pCl-DPDPE) | Tyr-D-Pen-Gly-D-Chloro-Phe-D-Pen (SEQ ID NO: 27) |
| [D-Pen$^2$, Pen$^5$]-enkephalin (DPLPE) | Tyr-D-Pen-Gly-Pen-Pen (SEQ ID NO: 28) |
| [D-Ser$^2$, D-Leu$^5$]- enkephalin-Thr (DSLET) | Tyr-D-Ser-Gly-Phe-Leu-Thr (SEQ ID NO: 29) |
| [D-Ala$^2$, D-Leu$^5$]- enkephalin (DADLE) | Tyr-D-Ala-Gly-Phe-D-Leu (SEQ ID NO: 30) |
| Met-enkephalin-Arg-Phe (MERF) | Tyr-Gly-Gly-Phe-Met-Arg-Phe (SEQ ID NO: 31) |
| CTOP | D-Phe-Cys-Tyr-D-Trp-Orn-Thr-Pen-Thr (SEQ ID NO: 32) |
| Ac-RYYRIK | Ac-Arg-Tyr-Arg-Ile-Lys (SEQ ID NO: 33) |

TABLE II-continued

List of opioid peptides

| | |
|---|---|
| ([D-Arg2, Lys4]-Dermorphin1)-amide (DALDA) | Tyr-D-Arg-Phe-Lys (SEQ ID NO: 34) |
| (D-Ala², N-Methyl-Phe⁴, Met(O)⁵-ol]-enkephalin (FK-33824) | Tyr-D-Ala-Gly-N-Methyl-Phe-Gly-ol (SEQ ID NO: 35) |
| [D-Ala², Leu⁵, Cys⁶]- enkephalin (DALCE) | Tyr-D-Ala-Gly-Phe-D-Leu-D-Cys (SEQ ID NO: 36) |
| [D-Ala², Glu⁴]- Deltorphin II | Tyr-D-Ala-Phe-Glu-Val-Val-Pro Gly-amide (SEQ ID NO: 37) |
| [D-Ala2]Deltorphin 1 | Tyr-D-Ala-Phe-Asp-Val-Val-Gly (SEQ ID NO: 38) |
| PL-017 | Tyr-Pro-Methyl-Phe-D-Pro (SEQ ID NO: 39) |
| ICI 174,8674 | N,N-diallyl-Tyr-Aib-Aib-Phe-Leu (SEQ ID NO: 40) |
| Others | |
| Morphiceptin | YPFP (SEQ ID NO: 41) |
| Nociceptin orphanin FQ | FGGFTGARKSARKLANQ (SEQ ID NO: 42) |
| Nocistatin | TEPGLEEVGEIEGQKQLQ (SEQ ID NO: 43) |
| Neuropeptide AF human (NPAF) | AGEGLNSQFWSLAAPQRF (SEQ ID NO: 44) |
| Neuropeptide SF human (NPSF) | SQAFLFQPQRF (SEQ ID NO: 45) |
| Substrate P | RPKPQQFFGLM (SEQ ID NO: 46) |
| β-human-Casomorphin | YPFVEPIP (SEQ ID NO: 47) |
| β-bovine-Casomorphin | YPFPGPI (SEQ ID NO: 48) |

Of the above opioids β-endorphins, enkephalins, and dynorphin are three human endogenous opioids. β-Endorphins are primarily found in the arcuate nucleus of the hypothalamus and in the pituitary gland, a feature that distinguishes this group from the enkephalins, which are not present in that area. Enkephalins may be broken down into two types, methionine enkephalin (met-enkephalin) and leucine enkephalin (leu-enkephalin), and their ratio is 4:1 respectively. They are more widely distributed in the brain than β-endorphins, being present in several areas including hypothalamic nuclei, limbic structures, caudate-putamen, the brain stem, several layers of the dorsal horn, peripheral nerves, and the adrenal medulla. The most powerful of the opioids, dynorphins, are found throughout the central and peripheral nervous systems. Some research supports the theory that they regulate pain at the spinal cord level, influence feeding behavior at the hypothalamic level, and function with other endogenous opioids to regulate the cardiovascular system. Dynorphins also may be involved in inhibiting intestinal motility, a phenomena that occurs when the body perceives pain. The presence of a large precursor to this opioid in the anterior pituitary suggests that it has many peripheral targets. Another opioid called neo-endorphin also is classified in the Dynorphin group.

The endogenous opioid system has been used to treat chronic pain through a technique called neuroaugmentation that involves electrical stimulation of specific areas of the brain to increase the quantity and reactivity of endogenous opioids. Partial or complete pain relief has been noted in patients treated with neuroaugmentation; lower levels of efficacy were observed in severely ill cancer patients. Spinal cord stimulation was found to be successful in treating chronic pain not associated with malignancy.

In some embodiments, the present invention contemplates the use of any of the opioids herein (whether naturally occurring or not) for modulating heat production, innate immune mechanisms, or mitochondrial activity in plants and/or animals as described in more detail herein.

2. Temperature Regulation

In one aspect, the compositions herein can also be used to regulate body temperature of an animal or a plant by modulating the outflow and inflow of heat from the body. Fever, an elevated core body temperature, is the most common thermoregulatory change that often accompanies inflammation and/or infection. One main source of heat in both plants and animals is the mitochondria. Another major source of heat in animals is muscular contraction. However, in plants, it is often difficult to measure their body/appendix temperature because the amount of heat produced is relatively small and the there is a large amount of heat loss to the environment.

In humans, opioids that have been used to alleviate pain have been linked to some degree with temperature regulation in humans. In particular, there is some evidence that suggests a link between the nervous system and thermoregulation (*Thermoregulation, Tenth International Symposium on the Pharmacology of Thermoregulation*. Blatteis C M, Ed., Annal. NY Acad. Sci. vol., 813, 1997), and more specifically between opioid peptides and thermoregulation (Adler M W et al, 1988, *Opioid System and Temperature Regulation*, Annu. Rev. Pharmacol. Toxicol., Vol. 28: 429-450).

In one aspect, the present invention relates to the surprising discovery that analgesics, such as opioids useful in treating pain in humans, can also be used to modulate heat production in plants. Thus, the present invention relates to uses of any of the compositions herein including for example (i) polypeptides comprising, consisting essentially of, or consisting of, an amino acid sequence of SEQ ID NO: 1-244, 248-249, or SEQ ID NO: 1-14 and 50-244, or SEQ ID NO: 1-2 or SEQ ID NO: 1; (ii) nucleic acids encoding any of the above polypeptides; and (iii) antibodies that specifically bind any of the above polypeptide, for modulating heat production in plants (e.g., crops or flowering plants).

Such heat production modulation can be used e.g., to prevent frost damage to the seed and plants. It can also increase the innate immune response of the plants (discussed in more detail below). The above uses can be accomplished by administering to a plant or seed any of the above compositions with an agricultural excipient via spray, drip irrigation or other irrigation, dipping at least a portion of said plant or seed in said composition, coating at least partially said plant or seed with said composition, etc. In another embodiment, a nucleic acid sequence encoding any of the above compositions can be used to transfect plants such that their heat production is regulated.

In another aspect, the present invention relates to methods of using the above compositions for modulating mitochondrial activity in plants and animals. Modulating mitochondrial activity can be used to prevent, treat, or ameliorate mitochondrial conditions in plants and animals.

Examples of mitochondrial conditions include, but are not limited to, Alpers disease (progressive infantile poliodystrophy); Barth syndrome (cardiomyopathy-neutropenia syndrome); lethal infantile cardiomyopathy (LIC); Beta-oxidation defects; carnitine deficiency and disorders; chronic progressive external ophthalmoplegia syndrome (CPEO); Kearns-Sayre syndrome (KSS); lactic acidosis; Leber hereditary optic neuropathy (LHON); Leigh disease (subacute necrotizing encephalomyelopathy); long-chain acyl-CoA dehydrogenase deficiency (LCAD); Luft disease; medium-chain acyl-CoA dehydrogenase deficiency (MCAD); mitochondrial cytopathy; mitochondrial encephalomyopathy lactic acidosis and stroke-like episodes (MELAS); mitochondrial encephalopathy; mitochondrial myopathy; multiple acyl-CoA dehydrogenase deficiency (MAD); glutaric aciduria Type II; myoclonic epilepsy and ragged-red fiber disease (MERRF); myoneurogastointestinal disorder and encephalopathy (MNGIE); neuropathy ataxia and retinitis pigmentosa (NARP); pearson syndrome; pyruvate carboxylase deficiency; pyruvate dehydrogenase deficiency (PHD); and short-chain acyl-CoA dehydrogenase deficiency (SCAD).

Other examples of mitochondrial conditions include respiratory chain disorders such as: Complex I: NADH dehydrogenase (NADH-CoQ reductase) deficiency; Complex II: Succinate dehydrogenase deficiency; Complex III: ubiquinone-cytochrome c oxidoreductase deficiency; Complex IV: cytochrome c oxidase (COX) deficiency; and Complex V: ATP synthase deficiency.

In one embodiment, an organism such as a plant or animal can be diagnosed for the presence of a mitochondrial condition by genetically screening the organism. In some embodiments, the organisms' genetic DNA or mitochondrial DNA can be analyzed. In some embodiments, the organism's RNA, mRNA, siRNA, or cRNA is analyzed.

An organism having by or susceptible of having a mitochondrial condition can then be administered one or more of the compositions disclosed herein to modulate, treat, or prevent the condition. Such compositions include, but are not limited to (i) a polypeptide comprising an amino acid sequence selected from the group consisting of: SEQ ID NO: 1-14 and 50-244 or an analog, homolog, mimetic or salt thereof; (ii) a nucleic acid sequence encoding at least in part a polypeptide comprising an amino acid sequence selected from the group consisting of: SEQ ID NO: 1-14 and 50-244; and (iii) an antibody or antibody fragment that specifically binds a polypeptide comprising an amino acid sequence selected from the group consisting of: SEQ ID NO: 1-14 and 50-244.

3. Inflammation

Acute and chronic pain is frequently associated with inflammation as a result of tissue destruction, abnormal immune reactivity or nerve injury.

In one aspect, the compositions herein can also be used to treat, modulate, or prevent inflammation in an organism. The inflammation can be due to a variety of external or internal insults, such as infectious agents, physical injury, hypoxia, or disease processes in nearly any organ or tissue in the body with one or more of the following symptoms: redness, heat, tenderness/pain, and swelling. Other examples are inflammatory diseases which the compositions herein can be used to treat include those such as rheumatoid arthritis, inflammatory bowel disease, scleroderma, cutaneous lupus erythematosus, systemic lupus erythematosus, type 1 and II diabetes, asthma, multiple sclerosis, abscess, wounds, meningitis, encephalitis, vasculitis, and cardiovascular diseases.

Since the discovery of salicylic acid (SA) as an anti-inflammatory compound and the subsequent synthesis of aspirin (ASA) over a century ago, several classes of structurally diverse compounds have become available for the treatment of human inflammatory disorders. These compounds are collectively known as NSAIDs and share with ASA a common mechanism by which they exert their anti-inflammatory action. Inflammation is now recognized as a type of immune response that directs immune system components to the site of injury or infection and is a major contributor to many diseases. Inflammation can be localized to a wound or an injury site and it can be systemic. Recent studies show a possible link between cardiovascular diseases and inflammation, e.g., the levels of C-reactive polypeptide, a molecular marker of inflammation, rank with cholesterol levels as indicators of future coronary heart disease.

In one aspect, the present invention relates to the use of the compositions herein including for example (i) polypeptides comprising, consisting essentially of, or consisting of, an amino acid sequence of SEQ ID NO: 1-151, or more preferably SEQ ID NO: 1-14, 50-244, 248-249, or more preferably SEQ ID NO: 1-2, or more preferably SEQ ID NO: 1; (ii) nucleic acids encoding any of the above polypeptides; and (iii) antibodies that specifically bind any of the above polypeptide, for the treatment of inflammatory conditions.

In some embodiments, the compositions above can be used in combination with one or more other anti-inflammatory agents to relief the inflammation.

4. Neoplastic Growth

Cell division and growth are essential for development and repair of organs and tissues. However excess or uncontrolled growth is important causes of disease such as cancer. Endogenous opioid peptides have played a role in regulating immunity and tumor growth. In addition to their use in the treatment of pain, opioids, appears to be important in the growth regulation of normal and neoplastic tissue (Rasmussen et al., 2002, NEL. 23:193-198). For example, release of endogenous opioids has been found to stimulate growth of 1 breast cancer in rats and opiate receptor antagonists have reduced the growth of these tumors (Balslev et al., 1989, Am. J. Path., 134:473-479). In another example, cyclooxygenase-2 (COX-2) and the prostaglandins resulting from its enzymatic activity have also been shown to play a role in modulating cell growth and development of human neoplasia. Evidence includes a direct relationship between COX-2 expression and cancer incidence in humans and animal models, increased tumorigenesis after genetic manipulation of COX-2, and significant anti-tumor properties of NSAIDs in animal models and in some human cancers. Moreover, recent data showed that COX-2 and the derived prostaglandins are involved in control of cellular growth, apoptosis, and signal through a group of nuclear receptors named peroxisome proliferator-activated receptors (PPARs; Trifan and Hla, 2003, J. Cell. Mol. Med. 7:207-222; Martinsgreen et al., 1994, Cancer Res. 54:4334-4341).

Thus, any of the compositions herein can also be used for the treat, prevent or modulate aberrant cell growth and in particular, cancer.

Non-limiting examples of cancers that may be modulated, treated, or prevented by the compositions herein include, but are not limited to, breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell leukemia, adenoma, hyperplasia, medullary carcinoma, pheochromocytoma, mucosal neuronms, intestinal ganglioneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforme, leukemias, lymphomas, malignant melanomas, epidermoid carcinomas, and other carcinomas and sarcomas.

The largest class of tumors falls into the ectoderm/endoderm class. This class includes the leading causes of death in humans (bronchogenic carcinoma, colon adenocarcinoma, breast carcinoma and prostate carcinoma and the most frequently occurring (though usually non-lethal) tumors of humans (squamous cell carcinoma of skin and basal cell carcinoma of skin). The other tumor groups are tumors of mesodermal lineage (including all sarcomas) and tumors of neuroectodermal lineage.

Thus, in some embodiments, a composition herein (e.g., SEQ ID NO: 1) can be administered to a subject susceptible of or having cancer to treat, modulate, or prevent the condition. Such compositions include for example (i) polypeptides comprising, consisting essentially of, or consisting of, an amino acid sequence of SEQ ID NO: 1-244, 248-249, or more preferably SEQ ID NO: 1-14 and 50-244, or more preferably SEQ ID NO: 1-2, or more preferably SEQ ID NO: 1; (ii) nucleic acids encoding any of the above polypeptides; and (iii) antibodies that specifically bind any of the above polypeptide, for the treatment of inflammatory conditions.

Such compositions can be administered along with one or more anti-neoplastic agents or be co-formulated with one or more anti-neoplastic agents to increase their therapeutic effect.

Anti-neoplastic agents can be grouped into the following general categories: alkylating agents, anti-metabolites, antimitotic inhibitors, anti-neoplastic antibiotics, hormonal agents, and miscellaneous. Example for an alkylating agent is Mechlorethamine hydrochloride that is used to treat Hodgkin's disease in man. Example for antimetabolites is methotrexate, an inhibitor of dihydrofolate reductase. Examples for mitotic inhibitors are Paclitaxel and docetaxel that are antimicrotubule agents. Examples for antineoplastic antibiotics are Mitoxantrone, an anthracenedione related to the anthracycline antibiotics, Doxorubicin and Bleomycin. Examples for hormonal agents are glucocorticoids.

Additional examples of antineoplastic agents include, but are not limited to: Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Imofosine; Interferon Alfa-2a; Interferon Alfa-2b; Interferon Alfa-n1; Interferon Alfa-n3; Interferon Beta-Ia; Interferon Gamma-Ib; Iproplatin; Irinotecan Hydrochloride; Lanreotide Acetate; Letrozole; Leuprolide Acetate Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycinl, Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

5. Innate Immune System

An organism has inborn defense mechanisms or innate immune system that allows it to defend itself against invasions by pathogens. The compositions herein can also be used to modulate, prevent and/or treat pathogen invasions (bacteria, virus, and fungi, crop pests, etc.) in humans and plants.

In humans, the few microbes that manage to cross the barriers of skin, mucus, cilia, and pH are usually eliminated by innate immune system, which commence immediately upon pathogen entry. If phagocytosis cannot rapidly eliminate pathogen, inflammation is induced with the synthesis of cytokines and acute phase polypeptides. This early-induced response is not antigen-specific. Only if the inflammatory process is unsuccessful at eliminating pathogen, the adaptive immune system is activated.

Plants also possess the mechanism of self-defense against pathogens and other abiotic stresses. (Cohen et al., (2001) Curr. Opin. Immunol. 13:55-62) Salicylic acid plays an important role in the induction of resistance to a broad spectrum of widely different pathogens such as fungi, bacteria or viruses such as the bacteria *Pseudomonas syringae* and the tobacco mosaic virus (TMV). While conventional pesticides targets the pathogens, most non-conventional pest control chemicals (biopesticides) are based on small molecule production either by added genetic material or microorganisms, which increases a plants ability to fight pathogens.

Thus, in some embodiments, the compositions herein are used to increase a seed, plant (e.g., crop) or plant cuttings' innate immune response to pathogen (e.g., bacteria, viruses, fungi, crop pests). This can help reduce crop losses. Other examples of conditions that may result in crop losses that can be preventable or diminished by the compositions herein include stress conditions such as drought, freezing or reduced temperatures, and other unfavorable environmental conditions (see discussion of temperature regulation above).

Examples of plants that may be treated with the compositions herein include, culture plans such as wheat, barley, rye, oats, rice, sorghum and the like; including Chenopodiaceae, e.g., sugar beet and fodder beet; pome and stone fruits and berries, e.g., apples, pears, plums, peaches, almonds, cherries, strawberries, raspberries and blackberries; *Legume*, e.g., beans, lentils, peas, soy beans; Brassicaceae, e.g., rape, mustard, cabbages and turnips. Cucurbitaceae, e.g., pumpkins, gherkins, melons, cucumbers, squashes; fibrous plants, e.g., cotton, flax, hemp, jute; citrus fruits, e.g., orange, lemon, grapefruit, mandarin; vegetables, e.g., spinach, lettuce, asparagus, ground-nuts; carrots, onions, tomatoes, potatoes, hot and sweet peppers; laurel-like plants, e.g., avocado, cinnamon, camphor tree; or plants such as maize, tobacco, nuts, coffee, sugar-cane, tea, vines, hops, bananas, rubber plants, poppy, olive, sunflower, coconut, castor-oil plant, cocoa as well as ornamental plants, e.g., flowers, shrubs, deciduous trees and evergreen trees such as conifers. This list is given with the purpose of illustrating the invention and not to delimiting it thereto.

Thus, in some embodiments, a composition herein can be administered to a plant or animal to prevent or treat a pathogen invasion. Such compositions include for example (i) polypeptides comprising, consisting essentially of, or consisting of, an amino acid sequence of SEQ ID NOs: 1-244, 248-249, or more preferably SEQ ID NOs: 1-14 and 50-244, or more preferably SEQ ID NOs: 1-2, or more preferably SEQ ID NO: 1; (ii) nucleic acids encoding any of the above polypeptides; and (iii) antibodies that specifically bind any of the above polypeptide, for the treatment of inflammatory conditions. Such compositions can further include a veterinary excipient, pharmaceutical excipient or agricultural excipient.

5. Neurological Condition.

Examples of neurological and neurodegenerative conditions that may be modulated, treated, or prevented by the compositions herein include, but are not limited to, anxiety disorder, panic disorder, obsessive-compulsive disorder, post-traumatic stress disorder, social phobia (or social anxiety disorder), specific phobias, and generalized anxiety disorder. Any of the above conditions can also be accompanied by or manifested by other conditions such as depression, drug abuse, alcoholism, Aicardi syndrome, Alzheimer's disease, amnesia, amyotrophic lateral sclerosis (Lou Gehrig's disease), anencephaly, aphasia, arachnoiditis, Arnold Chiari malformation, Batten disease, Bell's Palsy, brachial plexus injury, brain injury, brain tumors, Charcol-Marie tooth disease, dystonia, encephalitis, epilepsy, essential tremor, Guillain-Barre syndrome, hydrocephalus, hyperhidrosis, Krabbes disease, leukodystrophy, meningitis, Moebius syndrome, multiple sclerosis, muscular dystrophy, Parkinson's disease, peripheral neuropathy, postural orthostatic tachycardia syndrome, progressive supranuclear palsy, prosopagnosia, shingles, Shy-Drager syndrome, spasmodic torticollis, spina bifida, spinal muscular atrophy, stiff man syndrome, synesthesia, syringomyelia, thoracic outlet syndrome, tourette syndrome, toxoplasmosis, and trigeminal neurolagia.

V. Screening Assays

As used herein, the term "screening" refers to the use of assays designed to identify agents that alter (e.g., increase or decrease in a statistically significant manner) one or more of the compositions herein (e.g., a polypeptide comprising, consisting essentially of, or consisting of an amino acid sequence of (or encoded by) SEQ ID NOs: 1-244, 248-249, or any of the above with a methionine at the N-terminus). Briefly, in certain embodiments, when the compositions herein are contacted with a known polypeptide in the absence and presence of a candidate agent and under conditions and for a time sufficient for binding to the polypeptide to occur, and the effect of the agent on the binding interaction between the polypeptide and a composition herein is determined. A candidate agent may alter any of the herein described parameters directly (e.g., by physical contact with the polypeptide at a site of ligand binding) or indirectly (e.g., by interaction with one or more proximal or distal sites within the polypeptide, as may according to non-limiting theory alter the described parameter by interacting with other than a site of ligand binding, for instance, electron transfer or UV absorbance, or changing the conformation of the polypeptide. In some embodiments, the candidate agent may be a peptide, polypeptide, polypeptide or small molecules, and in certain preferred embodiments the candidate agent may be a structural mimetic of one or more of the compositions herein. Typically, and in more preferred embodiments such as for high throughput screening, candidate agents are provided as "libraries" or collections of compounds, compositions or molecules. Such molecules typically include compounds known in the art as "small molecules" and having molecular weights less than $10^4$ daltons, preferably less than $10^5$ daltons. For example, members of a library of test compounds can be administered to a plurality of samples, each containing at least one homolog of a polypeptide herein and a known polypeptide as provided herein, and then assayed for their ability to alter at least one of the above-described parameters.

The present invention provides compositions, methods and kits for use in (i) identifying agents that alter a biological effect by the compositions herein, and (ii) identifying peptides and peptidomimetics that function like the compositions herein.

One or more of above peptides can be used to screen small molecules and other compounds (e.g., antibodies, peptides, peptide nucleic acids, and nucleic acids) that interact with SEQ ID NOs: 245-247, 250, 253-256. Such library of compounds can include at least 1, 2, 3, 4, 5, 6, 7, 8, 9, 10, 15, 20, 30, 40, 50, 60 or 70 of the polypeptides herein.

Candidate agents further may be provided as members of a combinatorial library, which preferably includes synthetic agents prepared according to a plurality of predetermined chemical reactions performed in a plurality of reaction vessels. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides. Those having ordinary skill in the art will appreciate that a diverse assortment of such libraries may be prepared according to established procedures, and tested using the known polypeptides as a target.

There are a variety of assay formats known to those of ordinary skill in the art for detecting binding interactions between polypeptides and their cognate ligands. See, e.g., Harlow and Lane, 1988 In: *Antibodies: A Laboratory Manual*, Cold Spring Harbor Laboratory. Within one embodiment, a polypeptide or polypeptide is immobilized on a solid support prior to contact with the ligand. Binding may then be detected using a detection reagent that specifically binds to the polypeptide, for example, at a site known or suspected of being a site of ligand interaction (e.g., an antibody or fragment thereof), or using a detectable portion of the polypeptide (e.g., direct detection of a UV-absorbing moiety, or detection of electron transfer to an acceptor molecule).

A solid support may be any material known to those of ordinary skill in the art. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. A polypeptide may be immobilized on the solid support using a variety of techniques known to those of skill in the art, which are amply described in the patent and scientific literature. In the context of the present invention, the term "immobilization" refers to both non-covalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time.

Binding is generally allowed to occur under solution conditions and for an amount of time sufficient to detect the bound ligand. An appropriate amount of time may generally be determined by assaying the level of binding that occurs over a period of time. After incubating under conditions and for a time sufficient to permit interaction of a polypeptide of the invention and candidate receptor agent, the level of the ligand-receptor binding is detected and compared to the level of binding in the presence and absence the polypeptide of the invention.

For example, following a suitable interval for competitive ligand binding, unbound ligand is removed, and bound ligand is detected using a linked reporter group or a separate detectable marker comprising a reporter group. The method employed for detecting binding depends upon the nature of the reporter group employed. When electron transfer is detected, fluorescence or colorimetric or other techniques may be used. For radiometric quantification of ligand binding (or, e.g., competitive inhibition by a candidate agent of the binding site for a polypeptide comprising, consisting essentially of, or consisting of an amino acid sequence of (or encoded by) SEQ ID NOs: 1-244, 248-249, or any of the above with a methionine at the N-terminus, of a detectably labeled ligand comprising a radioactive group), scintillation counting or auto-radiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

An agent that binds to a polypeptide of the invention and/or to a polypeptide complex comprising a polypeptide of the invention may result in a detectable decrease or increase in binding the polypeptide to its natural receptor. Such altered levels of ligand-receptor binding can be detected by a statistically significant increase or decrease in binding to the receptor. Such agents that interfere with the ligand-receptor binding may be used as inhibitors of the compositions herein.

One or more of above peptides can be used to screen small molecules and other compounds (e.g., antibodies, peptides, peptide nucleic acids, and nucleic acids) that interact with SEQ ID NOs: 245-247, 250, 253-256. Such library of compounds can include at least 1, 2, 3, 4, 5, 6, 7, 8, 9, 10, 15, 20, 30, 40, 50, 60 or 70 of the polypeptides herein.

The present invention provides compositions, methods and kits for use in a phage display peptide library in which a library of variants of a peptide SEQ ID NOs: 1-244, 248-249, is expressed on the outside of a phage virion, and the DNA encoding each variant resides inside the virus. This creates a physical linkage between each variant protein sequence and the DNA encoding it, which allows rapid partitioning based on binding affinity to a given target molecule (antibodies, enzymes, cell-surface receptors, etc.) by an in vitro selection process called panning (Whaley et al., 2000, Nature 405:665-668).

The present invention also provides methods for identifying lead compounds for treatment of mitochondrial and metabolic conditions such as pain, inflammation, fever, Alzheimer's disease and any other disease mentioned herein. Such methods involve the use of a thermogenic plant for studying thermoregulation activity by candidate agents. Examples of thermogenic plants include those such as the *Sauromatum guttatum*, members of the Araceae family, *Amorphophallus konjac, Arum italicum, A. dioscoridis, Dracunculus vulgaris*; lotus (Nelumbonaceae), Dutchman's pipes (Aristolochiaceae), palms (Arecaceae and Cyclanthaceae), custard apples (Annonaceae), magnolias (Magnoliaceae), *Illicium* (Illiciaceae), *Rafflesia* (Rafflesiaceae), winter's bark (Winteraceae) and cycads (Cycadaceae).

In one example, using *Sauromatum guttatum* as the experimental module, on the day of inflorescence-opening, the *Sauromatum* appendix (a 20-40 cm-long, slender organ) becomes warm, reaching a 32° C. temperature (Skubatz et al., 1991, Plant Physiol. 95:1084-1088). The heat generated by the appendix is generated by the mitochondria. This mitochondrial activity can be triggered by the addition of phenolic compounds, including but not limited to, salicylic acid, aspirin, and 2,6-dihydroxybenzoic acid. Test agents can be applied to the plant and the plant's temperature may be monitored in vivo.

Test agents (e.g., polypeptide, such as those disclosed herein) that can module (increase, decrease, sustain, or shorten) heat generated by the plants can be used as lead compounds in animal models to test their ability to treat/modulate a metabolic condition. In some embodiments, small molecules or mimetics of the test compounds are applied to the plants. A small molecule or mimetic that has the same effect as a test agent such as a polypeptide may be then tested in an animal model for its ability to treat/modulate a metabolic condition. In some embodiments, such test compounds are agonists, antagonists and/or other modulators of mitochondrial activities.

Administration

The compositions (including formulations) herein can be administered systemically or locally to a plant or animal by any means known in the art. For example, to an animal such as a human, the compositions herein can be administered parenterally (which includes subcutaneously, intravenously, intramuscularly, intrasternally, intracavernously, intrathecally, and intraurethrally), intracranially, intraorbitally, intracapsularly, intraspinally, intracisternally, intrapulmonaryly (via inhalation), orally, intravenously, intra-arterially, intramedullary, intrathecally, intraventricularly, intrameatally, transdermally, subcutaneously, intraperitoneally, intranasally, enterally, vaginally, sublingually, or rectally. Preferably, the compositions herein are administered to an animal topically, subdermally or intravenously. In some embodiments, the composition/formulations herein are administered using insert(s), bead(s), timed-release formulation(s), patch(es) or fast-release formulation(s).

For plants, the compositions herein can be administered by any method known in the art, including, but not limited to, spray, drip irrigation or other irrigation, dipping at least a portion of said plant or seed in said composition, coating at least partially said plant or seed with said composition, etc. In another embodiment, a nucleic acid sequence encoding any of the above compositions can be used to transfect plants such that their heat production is regulated.

The compositions/formulations herein are preferably administered in an effective dose. It will be evident to those skilled in the art that the number, frequency, and duration of administration will be dependent upon the response of the host.

For therapeutic delivery, agents at concentrations of about 0.01 µg/kg to about 1000 mg/kg body weight may be administered, typically by the intradermal, subcutaneous, intramuscular or intravenous route, or by other routes. A preferred dosage is about 1 µg/kg to about 1000 mg/kg, or about 5 µg/kg to about 500 mg/kg, or about 10 µg/kg to about 100 mg/kg.

For agricultural delivery, agents may be administered at a concentration that is agriculturally therapeutically effective, e.g., about 50-3000 gram per hectare, preferably from about 50-1500 gram per hectare, and more preferably from about 150-300 gram per hectare. Assuming a composition is comprised of 100% active ingredients, then, in general, the amount of the subject composition used will range from about 0.005% to 25% of the weight of the seed, and more preferably, from about 0.01% to about 10% of the weight of the seed. In yet another embodiment the amount of the subject composition used will be in the range of 0.01% to 1% of the active ingredients relative to the weight of the seed, or 0.05% to 0.5%.

EXAMPLES

Example 1

A total of forty (40) male Sprague Dawley rats (Harlan Sprague Dawley Inc., Indianapolis, Ind., USA) were used in the study. The rats are specific pathogen free and approximately 250 grams upon arrival. The rats were housed in the vivarium in clear polycarbonate plastic cages (48×27×20 cm); 2 rats per cage until a few days prior to surgery at which point they were singularly housed for the remainder of the study procedures. The bedding material is irradiated corn-cob bedding (Bed-O-Cob, The Andersons, Maumee, Ohio, USA) that was changed weekly. The rats were acclimated for two weeks prior to the commencement of the experimental procedures. The room in which the rats were housed throughout the study was supplied with HEPA filtered air at the rate of 10-15 air changes per hour. The temperature was maintained at 18-26° C. with a relative humidity of 30-70%. Illumination is approximately 300 lumens/$m^2$ at 1 m above floor level on a 12-hour light/dark cycle. The rats had ad libitum access to oval pellet Certified Picolab Rodent Diet 20 (PMI Feeds Inc., Richmond, Ind., USA) and deionized water.

All rats were anesthetized with Inhalation anesthetic (Isoflurane). The plantar aspect of the foot was cleaned and prepped for aseptic surgery. The animals were placed in ventral recumbancy. A 1-246 cm longitudinal incision was made with a #11 blade, through the skin and fascia of the plantar aspect of the foot, starting 0.5 cm from the proximal edge of the heel and extending towards the toes. The plantaris muscle was elevated and incised longitudinally. The muscle origin and insertion remained intact. Gentle pressure was applied for hemostatis, if needed. The skin was closed with suture material and the wound site covered with a triple antibiotic ointment. The rats were allowed to recover in their cage until regaining full mobility.

On days 1 and 3 post-surgery, animals were dosed with the appropriate test or control compound (Table III).

TABLE III

Treatment groups for the first study of the analgesic property of SEQ ID NO: 1 on post-operative pain in rats.

| Group No. | Surgery | Treatment | Dose | Route |
|---|---|---|---|---|
| 1 | Sham (No surgery) | Vehicle 0.17% DMSO, 0.05% Silwet in H2O | 0.1 mL | Topical |
| 2 | Brennan model | Vehicle | 0.1 mL | Topical |
| 3 | Brennan model | Morphine in PBS | 5 mg/kg | Subcutaneous |
| 4 | Brennan model | SEQ ID NO: 1 in vehicle | 150 µg/0.15 mL | Topical |
| 5 | Brennan model | SEQ ID NO: 1 in PBS | 150 µg/0.1 mL | Subdermal |

On days 1 and 3 post-surgery, the rats underwent Von Frey testing for mechanical allodynia. Tactile sensitivity (i.e. mechanical allodynia) was measured using calibrated filaments touched to the plantar surface of the affected limb.

Procedurally, the rats were placed in a plastic cage with a wire mesh bottom and allowed to acclimate for 5 to 10 minutes. Once the animals settled, the plantar surface of the right hind paw was touched with a 2.0 g von Frey filaments. In the absence of a paw withdrawal response to the initially selected filament, a stronger stimulus was presented; in the event of paw withdrawal, the next weaker stimulus was chosen. In this fashion, the resulting pattern of positive and negative responses was used to determine the paw withdrawal threshold.

FIG. 1. Data were analyzed using a one-way ANOVA followed by Newman-Keuls' Multiple Comparison. Statistical significance was p<0.05. It shows that SEQ ID NO: 1 was able to significantly reduce pain. Abbreviations: TA, test article, which is SEQ ID NO: 1; sderm, sub-dermal injection; top, topical application; veh, vehicle; surg, surgery; morph, morphine. The rats appeared relaxed and with less anxiety.

Example 2

In a second independent study the rat hind paw withdrawal sensitivity was again evaluated after 3 h and 3 day post-surgery when the rats had received SEQ ID NO: 1 at three different concentrations: 1, 15 and 50 mg/kg. The dosing route was subdermal injection adjacent to the wound site. The rats received one dose 3 hours after the surgery and on Day 3 post-surgery, group 3 was dosed again as described in the Table IV. Pain measurements were taken 15-20 min after application of the drug. Baseline pain behavior was measured as follows: Withdrawal responses to mechanical stimulation were determined using von Frey filaments applied from underneath the cage through openings (12×12 mm in the plastic mesh floor to an area adjacent to the intended incision. Each von Frey filament (Target force of 0.008 g to 300 g) was applied once starting with 0.008 g filament and continuing until a withdrawal response occurred or 300 g force was reached. The median force producing a response, determined from three tests given over a 10-min period was considered the withdrawal threshold.

Figure 2:
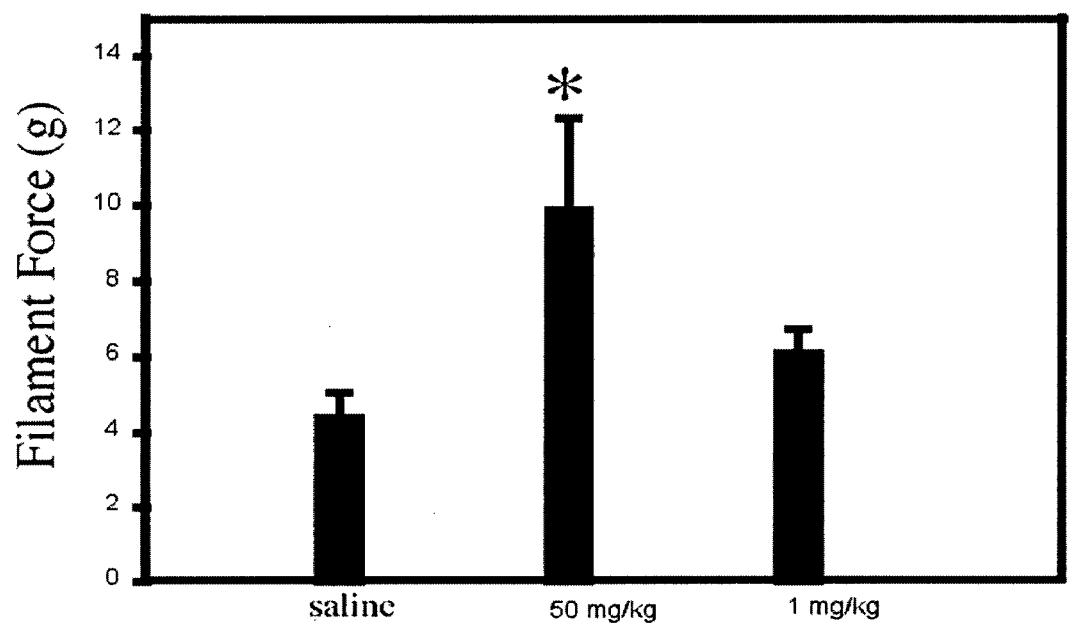
FIG. 2 illustrates the efficacy of SEQ ID NO: 1 in relieving pain in rats 3 h after surgery

FIG. 2 illustrates withdrawal results show that SEQ ID NO: 1 has analgesic and property 3 h after surgery. In the saline treated animals, the control, 3-hour post-surgery were 25.1, 4.4 and 12.7 g, indicating significant hyperalgesic response immediately after surgery which subsided by Day-3. In the animals treated with 50 and 15 mg/kg doses of SEQ ID NO: 1 subdermally, the pre-dose, pre-surgery responses were 30.2 and 28.1 g, which were comparable to the saline treated group indicating uniformity of the pain response in all the three groups. The withdrawal response in the 50 mg/kg SEQ ID NO: 1 administered on Day-1 was 9.9 g compared to the 4.4 g for the saline group at the same time-point, indicating a 125% effect. The data expressed as mean±SE, were analyzed using ANOVA followed by Tukey-HSD Multiple Comparison Test. Statistical significance was p<0.05.

Figure 3:
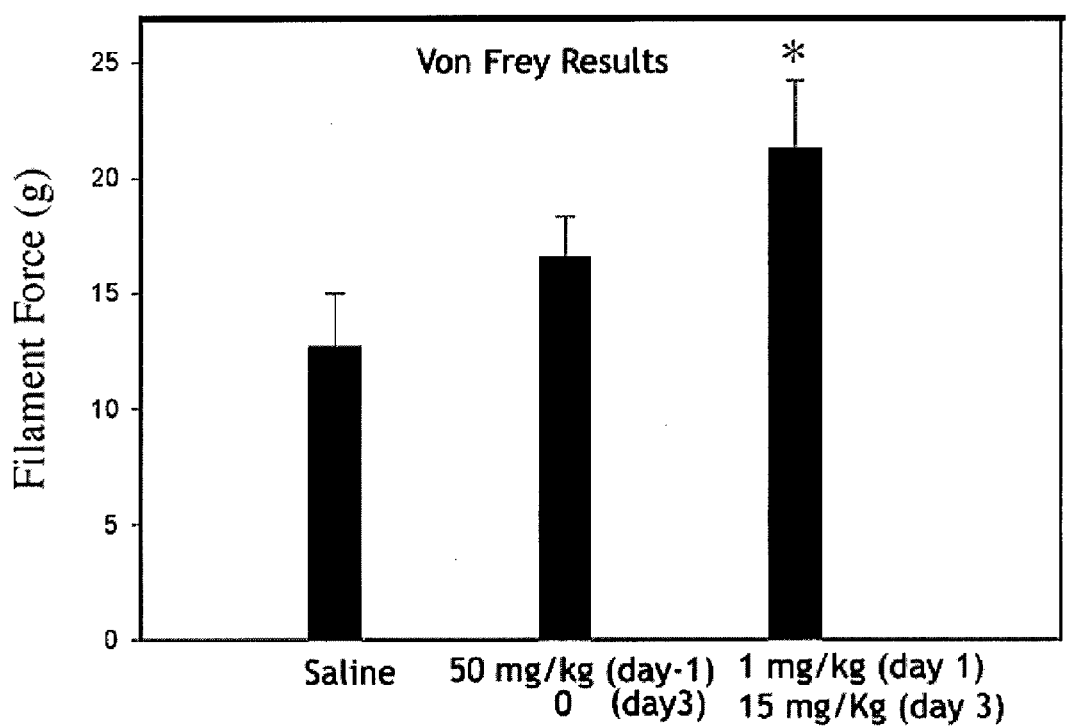
FIG. 3 illustrates the efficacy of SEQ ID NO: 1 in relieving pain in rats after surgery

FIG. 3 Withdrawal results show that SEQ ID NO: 1 has analgesic and property on Day 3 post-surgery. The group, which did not receive any further dosing showed a 31% increase in response time on Day 3, compared to the saline group at the respective time point. In the group of animals administered with 1 mg/kg NPL/PA2 on day 1 post-surgery, the 3-hour post surgery measurements showed a 39% increase in the pain threshold. On Day-3, when these animals were administered with 15.25 mg/kg of SEQ ID NO: 1 subdermally, the withdrawal response was at 21.3 g, compared to the withdrawal response of saline group at 12.7 g, constituting an increase of 68%. The data expressed as mean±SE, were analyzed using ANOVA followed by Tukey-HSD Multiple Comparison Test. Statistical significance was p<0.05.

TABLE IV

Treatment groups for the first study of the analgesic property of SEQ ID NO: 1 on post-operative pain in rats.

| Group | Number of Animals Male | Route | Time of Dosing | Concentration (mg/kg) |
|---|---|---|---|---|
| 1 | 10 | saline, vehicle | Day 1, 3 h after surgery | 0 |
| 2 | 10 | subdermal | Day 1, 3 h after surgery | 50 mg/kg |
| 3 | 10 | subdermal | Day 1, 3 h after surgery Day 3 | 1 mg/kg 15 mg/kg |

Example 3

An adult male subject suffering from chronic pain as a result from of multiple fractures to both tibia and fibula in both legs and severe traumatic soft tissue damage was topically administered a composition containing a polypeptide of SEQ ID NO: 1 at regions experiencing pain (mostly knees and ankles). The pharmaceutical formulation administered comprised of 5 µM of SEQ ID NO: 1 in 0.01% Silwet L-77. Relief was noticed within 15 min. after administration of a single dose of about 5 µg/10 cm2 of SEQ ID NO: 1. The relief lasted for more than a week. A scaled score of 1 to 10 was used to evaluate treatment efficacy where a score of 10 represented a patient with sever pain discomfort and complete inability to walk. A scaled score of 1 represented a patient experiencing no pain and able to freely walk or move the legs. Prior to treatment, the patient scored an 8-9 representing chronic pain and difficulties in walking long distance. After the treatment, the patient scored a 2-3 representing a significant decrease in pain. Treatment efficacy lasted for about 10 days.

Example 4

Figure 4:
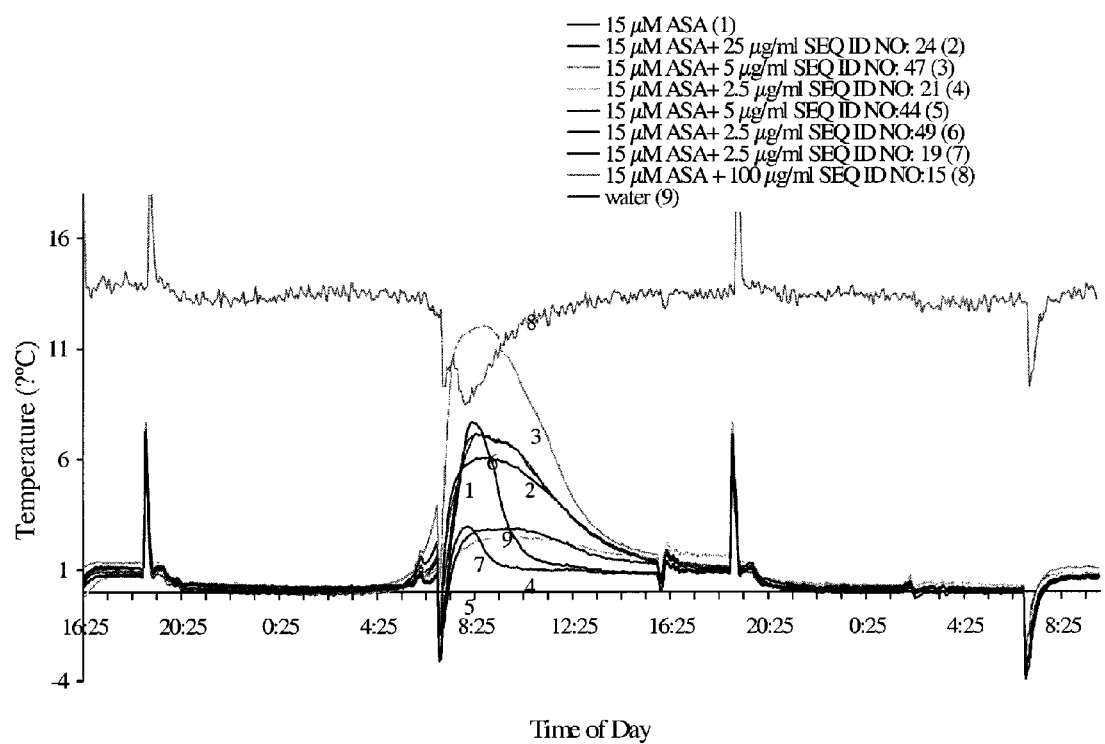
FIG. 4 illustrates heat production by *Sauromatum guttatum* appendix treated with aspirin (ASA) and various opioid peptides and the neurotoxic peptide β-amyloid peptide (Aβ 1-42).

FIG. 4 illustrates modulation of heat generated by aspirin (ASA) in *Sauromatum guttatum* appendix in the presence of various opioid peptides and the Alzheimer's peptide, Aβ 1-42. One day before heat-production, sections of the appendix were placed in different aqueous solutions containing ASA with or without an opioid peptide. [Leu]-Enkephalin, SEQ ID NO: 15; Human β-Endorphin; SEQ ID NO: 19; Dynorphin A, SEQ ID NO: 21; Endomorphin 2, SEQ ID NO: 24; Neuropeptide AF, SEQ ID NO: 44; β-human-Casomorphin, SEQ ID NO: 47; Alzheimer's peptide, SEQ ID NO: 48. Sections of the appendix were placed in distilled water that was not generated any heat is the control (9). Temperature was recorded with thermocouples attached to the section every 5 min. The y-axis is the appendix temperature above ambient and the x-axis shows the time of the day. This figure illustrates that opioid peptides and the neurotoxic Alzheimer's peptide, Aβ 1-42 can modulate thermogenicity in plants as well as animals and act as mitochondrial modulators.

Example 5

Figure 5:
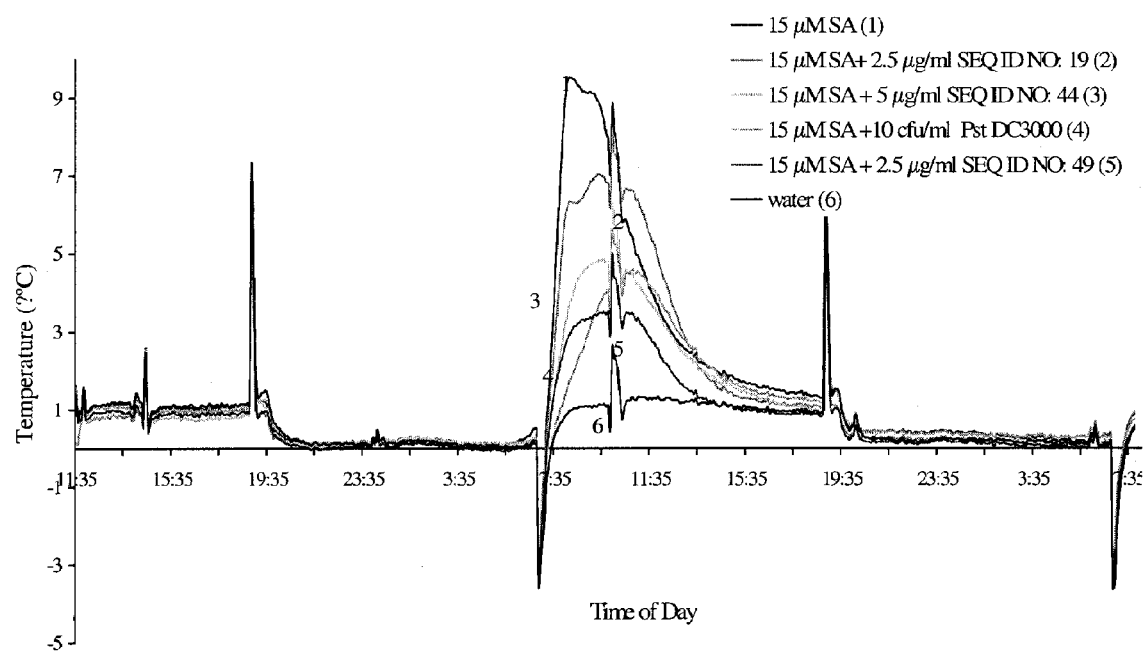
FIG. 5 illustrates heat production by *Sauromatum guttatum* appendix treated with salicylic acid (SA) in the presence of human opioid peptides (β-Endorphin and Neuropeptide AF) and, β-amyloid peptide, (Aβ 1-42); and a plant virulent bacterial pathogen (Pst DC3000).

FIG. 5 illustrates modulation of heat generated by salicylic acid (SA) in the presence of human opioid peptides (β-Endorphin, SEQ ID NO: 19 and Neuropeptide AF, SEQ ID NO: 44) and, the Alzheimer's peptide, Aβ 1-42, SEQ ID NO: 49, and, a plant virulent bacterial pathogen (Pst DC3000). One day before heat-production, sections of the appendix were placed in different aqueous solutions containing salicylic acid (SA) with or without a peptide or with the bacterial plant pathogen, *Pseudomonas syringae* pv. Tomato, DC3000. Sections from the appendix were placed in distilled water that was not generated any heat is the control (water). Temperature was recorded with thermocouples attached to the sections every 5 min. The y-axis is the appendix temperature above ambient and the x-axis shows the time of the day. This figure illustrates that these peptides modulate thermogenicity in plants as well as animals and act as mitochondrial modulators.

Example 6

Figure 6:
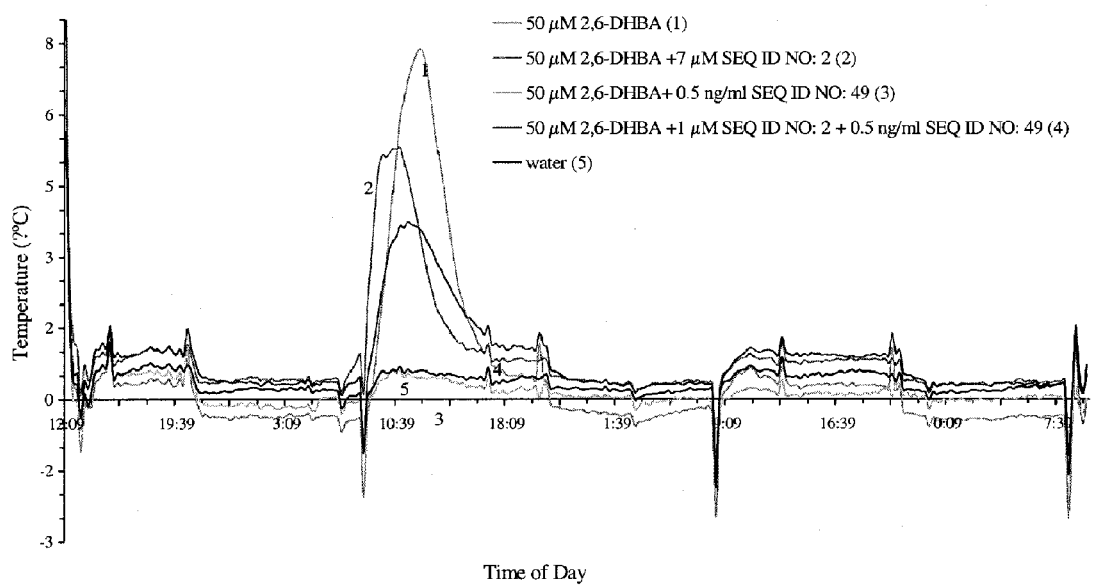
FIG. 6 illustrates heat production by *Sauromatum guttatum* appendix treated with 2,6-dihydroxybenzoic acid (2,6-DHBA) in the presence of β-amyloid peptide (Aβ 1-42), SEQ ID NO: 2, and SEQ ID NO: 1.

FIG. 6 illustrates modulation of heat generated by 2,6-dihydroxybenzoic acid in the presence of the Alzheimer's peptide, Aβ 1-42, SEQ ID NO: 49 and a plant gene derived sequence in the *Sauromatum guttatum* appendix. One day before heat-production, sections of the appendix were placed in different solutions containing 2,6-dihydroxybenzoic acid (2,6-DHBA) with or without SEQ ID NO: 2 (FLPSEFGVDVDR) and SEQ ID NO: 51. Heat-production was monitored with thermocouples attached to the sections. A section placed in distilled water that was not generated any heat is the control (water). The y-axis is the appendix temperature above ambient and x-axis shows the time of the day. The temperature was recorded every 5 min. Moreover, in a second experiment, application of SEQ ID NO: 2 up to 50 μM did not generate heat (data not shown). This figure illustrates that these peptides modulate thermogenicity in plants as well as animals and act as mitochondrial modulators.

Example 7

Administration of 10 μm of SEQ ID NO: 1 in 0.01% Silwet L-77 to *Arabidopsis thaliana* plants induces early flowering and abundance of flowers and pods.

Example 8

Seeds of *Arabidopsis* ecotype Columbia (Col-0) were planted in potting soil. Plants were cultivated in a growth chamber with 10-h d (200 μmol m$^{-2}$ s$^{-1}$ at 22° C.) and 14-h night (18° C.) cycles and 80% RH. Once a week plants were supplied with water and modified one-half strength Hoagland nutrient solution: 2 mM KNO 5 mM Ca(NO$_3$)$_2$ and trace elements, pH 7.

A virulent plant pathogen, Pst *Pseudomonas syringae* pv tomato, DC3000 was grown at 28° C. on King's medium B containing 40 mg/L tetracycline. Plants were inoculated with 1×10$^7$ cfu/ml of the pathogen in 0.01% Silwet L77 (v/v) (a surfactant) and distilled water 5 weeks after sowing. The bacterial suspension or a control solution (0.01% Silwet L77 in water) was then sprayed on the plant once.

Disease symptoms in *Arabidopsis* are water-soaked, spreading lesions, sometimes surrounded by chlorotic margin that eventually lead to yield loss and plant death.

To test the efficacy of SEQ ID NO: 15, some healthy and some disease plants were sprayed with salicylic acid in 0.01% Silwet L77; some healthy and some disease plants were sprayed with SEQ ID NO: 15 in 0.01%. Silwet L77, and some healthy and some disease plants were sprayed with salicylic acid in combination with SEQ ID NO: 15 in 0.01%. Silwet L77. A control group of some healthy and some disease plants were sprayed with water in 0.01%. Silwet L77.

Symptoms of plants were classified by the percentage of infected leaves and the severity of the infection.

It was noted that application of 20 μl salicylic acid at a concentration of 1 mM and 20 μl SEQ ID NO: 15 to the leaves is enough to trigger systemic resistance to the virulent bacteria concentration. TABLE V. Sequence listings.

| SEQ ID NO | Sequence |
|---|---|
| 1 | FLPS |
| 2 | FLPSEFGVDVDR |
| 3 | KRFLPSEFGVDVDR |
| 4 | KRFFPSEFGLDVDR |
| 5 | KRFLPSEFGFDVDH |
| 6 | KRFFPSEFGNDVDK |
| 7 | KRFFPSEFGTDVDR |
| 8 | KRFLPSEFGMDPPR |
| 9 | KRFLPSEFGMDPAL |
| 10 | RRFLPSEFGLDPDH |
| 11 | KRFLPSEFGMDPDI |
| 12 | KRFFPSEFGNDVDR |
| 13 | KKFYPSEFGNDVDR |
| 14 | VKRFFPSEFGLDVDR |
| 15 | YGGFL |
| 16 | YGGFM |
| 17 | YGGFLRKYPK |
| 18 | YGGPLRKYP |
| 19 | YGGFMTSEKSQTPLVTLFKNAIIKNAYKKGE |
| 20 | YGGFMTSEKSQTPLVT |
| 21 | YGGFLRRIRPKLKWDNQ |
| 22 | YGGFLRRQFKVVT |
| 23 | YPTF |
| 24 | YPFF |
| 25 | Tyr-D-Ala-Gly-N-Methyl-Phe-Gly-ol - |
| 26 | Tyr-D-Pen-Gly-Phe-D-Pen |
| 27 | Tyr-D-Pen-Gly-D-Chloro-Phe-D-Pen |
| 28 | Tyr-D-Pen-Gly-Pen-Pen |
| 29 | Tyr-D-Ser-Gly-Phe-Leu-Thr |
| 30 | Tyr-D-Ala-Gly-Phe-D-Leu |
| 31 | Tyr-Gly-Gly-Phe-Met-Arg-Phe |
| 32 | D-Phe-Cys-Tyr-D-Trp-Orn-Thr-Pen-Thr - |

| SEQ ID NO | Sequence |
|---|---|
| 33 | Ac-Arg-Tyr-Arg-Ile-Lys |
| 34 | Tyr-D-Arg-Phe-Lys |
| 35 | Tyr-D-Ala-Gly-N-Methyl-Phe-Gly-ol |
| 36 | Tyr-D-Ala-Gly-Phe-D-Leu-D-Cys |
| 37 | Tyr-D-Ala-Phe-Glu-Val-Val-Pro Gly-amide |
| 38 | Tyr-D-Ala-Phe-Asp-Val-Val-Gly |
| 39 | Tyr-Pro-Methyl-Phe-D-Pro |
| 40 | N,N-diallyl-Tyr-Aib-Aib-Phe-Leu |
| 41 | YPFP |
| 42 | FGGFTGARKSARKLANQ |
| 43 | TEPGLEEVGEIEGQKQLQ |
| 44 | AGEGLNSQFWSLAAPQRF |
| 45 | SQAFLFQPQRF |
| 46 | RPKPQQFFGLM |
| 47 | YPFVEPIP |
| 48 | YTPFPGPI |
| 49 | DAEFRHDSGYEVHHQKLVFFAEDVGSNKGAIIGLMVGGVVIA |
| 50 | NPFLPS |
| 51 | NPYLPS |
| 52 | NPWLPS |
| 53 | NPHLPS |
| 54 | DPFLPS |
| 55 | DPYLPS |
| 56 | DPWLPS |
| 57 | DPHLPS |
| 58 | FLPPPPSS |
| 59 | YLPPPPSS |
| 60 | WLPPPPSS |
| 61 | HLPPPPSS |
| 62 | GIPYTY |
| 63 | SIPYTY |
| 64 | TIPYTY |
| 65 | GVPYTY |
| 66 | GIPFTY |
| 67 | NIPFTY |
| 68 | GIPFTF |
| 69 | GIPHTY |
| 70 | YTIKAVDD |
| 71 | YTINAVDD |
| 72 | YTIEAVDD |
| 73 | YTINSVDD |
| 74 | YTIRAAND |
| 75 | YTIKTIDD |
| 76 | FTIKAAND |
| 77 | FTIKAVDD |
| 78 | SFGVEASELYPDVKYT |
| 79 | SWGLEASELYPDVKYT |
| 80 | SFGVEATALYPDVKYT |
| 81 | HAVFVNG |
| 82 | HCVFVKG |
| 83 | HSVFVNG |
| 84 | HSAFVKG |
| 85 | HAAFVRG |
| 86 | HAGYIRG |
| 87 | HTAFVKG |
| 88 | HSSYVKG |
| 89 | |
| 90 | DFTSFTIDPSFG |
| 91 | CFAGLFLFVPCLGGCH |
| 92 | HCGGLCPVFLFLGAFC |
| 93 | GAPYAAFC |
| 94 | GFSPDITFSTFD |
| 95 | TLFYGAFC |
| 96 | PLSYGAFF |
| 97 | PLSYGGFY |
| 98 | GAFYGAFM |
| 99 | FFAGYFLP |
| 100 | CFGGYYLP |
| 101 | CFAAYFAG |
| 102 | CFAGYFLT |
| 103 | FFAGYSLP |
| 104 | YFGGYSLP |
| 105 | MFAGYFAG |
| 106 | YFAGYALP |
| 107 | WFADFFLP |

| SEQ ID NO | Sequence |
|---|---|
| 108 | PLFYGAFF |
| 109 | PLYYGGFC |
| 110 | TGYIGKFLV |
| 111 | TGYIGKFIV |
| 112 | TGYIGKFVA |
| 113 | TGYIGKYIV |
| 114 | TGYIGKYLV |
| 115 | TGYIGRHV |
| 116 | TGYLGRHV |
| 117 | TGYIGKRIV |
| 118 | TGFIGKRIV |
| 119 | VLFKGIYGT |
| 120 | VIFKGIYGT |
| 121 | AVFKGIYGT |
| 122 | VIYKGIYGT |
| 123 | VLYKGIYGT |
| 124 | VHRGIYGT |
| 125 | VHRGLYGT |
| 126 | TYKVDPYLESAEVGFS |
| 127 | TYKVDPYLESAELGWS |
| 128 | TYKVDPYLATAEVGFS |
| 129 | TYKVDPYLESAEVGFS |
| 130 | TYKVDPYLESAELGWS |
| 131 | TYKVDPYLATAEVGFS |
| 132 | KIYLIK |
| 133 | KIYLVK |
| 134 | RIYLIK |
| 135 | RIYLVK |
| 136 | KILYIK |
| 137 | KVLYIK |
| 138 | KVLYIR |
| 139 | IKKEWL |
| 140 | IKNEWL |
| 141 | TKKEWL |
| 142 | LKEWI |
| 143 | IKDEWL |
| 144 | IKGEWL |
| 145 | ILEEWK |
| 146 | LWEKKI |
| 147 | LWENKI |
| 148 | LWEKKT |
| 149 | IWEKL |
| 150 | LWEDKI |
| 151 | LWEGKI |
| 152 | KWEELI |
| 153 | SPLF |
| 154 | RDVDVGFESPLFRK |
| 155 | PFPY |
| 156 | SPLFPN |
| 157 | SPLYPN |
| 158 | SPLWPN |
| 159 | SPLHPN |
| 160 | SPLFPD |
| 161 | SPLYPD |
| 162 | SPLWPD |
| 163 | SPLHPD |
| 164 | SSPPPPLF |
| 165 | SSPPPPLY |
| 166 | SSPPPPLW |
| 167 | SSPPPPLH |
| 168 | GTYPIG |
| 169 | YTYPIS |
| 170 | YTYPIT |
| 171 | YTYPVG |
| 172 | YTFPIG |
| 173 | YTFPIN |
| 174 | FTFPIG |
| 175 | YTHPIG |
| 176 | DDVAKITY |
| 177 | DDVANITY |
| 178 | DDVAEITY |
| 179 | DDVSNITY |
| 180 | DNAARITY |
| 181 | DDITKITY |
| 182 | DNAAKITF |

| SEQ ID NO | Sequence |
|---|---|
| 183 | GNVFVAH |
| 184 | GKVFVCH |
| 185 | GNVFVSH |
| 186 | GKVFASH |
| 187 | GVFAAH |
| 188 | GRIYGAH |
| 189 | GKVFATH |
| 190 | GKVYSSH |
| 191 | GKVYSSH |
| 192 | CFAYFAG |
| 193 | CFAGYFLT |
| 194 | FFAGYSLP |
| 195 | YFGGYSLP |
| 196 | MFAGYFAG |
| 197 | PLFYGAFF |
| 198 | PLYYGGFC |
| 199 | GAFYAAFC |
| 200 | TLFYGAFC |
| 201 | PLSYGAFF |
| 202 | PLSYGGFY |
| 203 | GAFYGAFM |
| 204 | PLAYGAFY |
| 205 | PLFFDAFW |
| 206 | FFAGYFPL |
| 207 | CFGGYYLP |
| 208 | VLFKGIYGT |
| 209 | VIFKGIYGT |
| 210 | AVFKGIYTG |
| 211 | VIYKGIYGT |
| 212 | VLYKGIYGT |
| 213 | VHRGIYGT |
| 214 | VHRGLYGT |
| 215 | VIRKGIYGT |
| 216 | VIRKGIFGT |
| 217 | TGYIGKFLV |
| 218 | TGYIGKFIV |
| 219 | TGYIGKFVA |
| 220 | TGYIGKYIV |
| 221 | TGYIGKYLV |
| 222 | TGYIGRHV |
| 223 | TGYLGRHV |
| 224 | KILYIK |
| 225 | KVLYIK |
| 226 | KILYIR |
| 227 | KVLYIR |
| 228 | KIYLIR |
| 229 | KIYLVK |
| 230 | RIYLVK |
| 231 | LWEKKI |
| 232 | LWENKI |
| 233 | LWEKKT |
| 234 | IWEKL |
| 235 | LWEDKI |
| 236 | LWEGKI |
| 237 | KWEELI |
| 238 | IKKEWL |
| 239 | IKNEWL |
| 240 | TKKEL |
| 241 | LKEKL |
| 242 | IKDEWL |
| 243 | IKGEWL |
| 244 | ILEEWK |
| 245 | MDKKSRVLIVGGTGFIGKRIVKASLALGHPTYVLFRPEALSYID KVQMLISFKQLGAKLLEASLDDHQGLVDVVKQVDVVISAVSG GLVRHHILDQLKLVEAIKEAGNIKRFLPSEFGMDPDVVEDPLE PGNITFIDKRKVRRAIEAATIPYTYVSSNMFAGFFAGSLAQLQD APRMMPARDKVLIYGDGNVKGVYVDEDDAGIYIVKSIDDPRT LNKTVYIRPPMNILSQKEVVEIWERLSGLSLEKIYVSEDQLLNM KDKSYVEKMARCHLYHFFIKGDLYNFEIGPNATEGTKLYPEV KYTTMDSYM ERYL |
| 246 | MGESKRTEKTRVLVVGATGYIGKRIVRACLAEGHETYVLQRP EIGLEIEKVQLFLSFKKLGARIVEGSFSDHQSLVSAVKLVDVVV SAMSGVHFRSHNILVQLKLVEAIKEAGNVKRFLPSEFGMDPPR MGHALPPGRETFDQKMERQAIEAAGIPYTYVVGACFAAYFAG NLSQMVTLLPPKEKVNIYGDGNVKVVFADEDDIAKYTAKTLN DPRTLNKTVNIRPPDNVLTQLELVQIWEKLTGKELEKTNIAAQ DFLANIEQMEIPHQAGIGHFYHIFYEGCLTDHEVGEDEEASSLY PDVKYKRMDDYLRMFL |
| 247 | MATEKSKILVIGGTGYLGKFLVEASAKAGHSTFALVREATLSD PVKGKTVQSFKDLGVTILHGDLNDHESLVKAIKQVDVVISTVG SMQILDQTKIISAIKEAGNVKRFLPSEFGVDVDRTSAVEPAKSA FAGKIQIRRTIEAEGIPYTYAVTGCFGGYYLPTLVQFEPGLTSPP RDKVTILGDGNAKAVINKEEDIAAYTIKAVDDPRTLNKILYIKP SNNTLSMNEIVTLWEKKIGKSLEKTHLPEEQLLKSIQESPIPINV VLSINHAVFVNG DTNISIEPSFGVEASELYPDVKYTSVDEYLSYFA |

-continued

| SEQ ID NO | Sequence |
|---|---|
| 248 | YGGFLRRQPKVVT |
| 249 | KYPKRSSEVAGEGDGDSMGHEDLYKRYGGFLRRIRPKLKWD NQKRYGGFLRRQFKVVTRSQEDPNAYSGELFDA |
| 250 | MAWQGLVLAACLLMFPSTTADCLSRCSLCAVKTQDGPKPINP LICSLQCQAALLPSEEWERCQSFSFFTPSTLGLNDKEDLGSKSV GEGPYSELAKLSGSFLKELEKSKFLPSISTKENTLSKSLEEKL RGLSDGFREGAESELMRDAQLNDGAMETGTLYLAEEDPKEQ VKR YGGFLRKYPKRSSEVAGEGDGDSMGHEDLYKR YGGFLR RIRPKLKWDNQKRYGGFLRRQFKVVTRSQEDPNAYSGELFDA |
| 251 | ttt ctg ccc tca |
| 252 | ttt ctg ccc tca gaa ttt gga gta gac gta gac aga |
| 253 | MVKKIANDVSNKLFPLPKGFGDFVGIEDHIKAIKSILCLESKEA RIMVGIWGQSGIGKSTIGRALFSQLSSQFHHRAFITYKSTSGSD VSGMKLSWEKELLSEILGQKDIKIDHFGVVEQRLKHKKVLILL DDVDNLEFLKTLVGKAEWFGSGSRIIVITQDKQLLKAHEIDLV YEVELPSQGLALKMISQYAfGKDSPPDDFKELAFEVAELVGSL PLGLSVLGSSLKGRDKDEWVKMMPRLRNDSDDKIEETLRVGY DRLNKKNRDNVKELLEDDVGLTMLADKSLIRITPDGDIEMHN LLEKLGREIDRAKSKGNPAKQFLTNFEDIQEVVTEKTGTETV LGIRVPPTVLFSTRPLLVINEESFKGMQIGLWSKIDLPQGLVYLP LKLKLLKWNYCPLKSLPSTFKAFYLVNLIMKYSKLEKLWEGT LPLGSLKKMDLGCSNNLKEIPDLSLAINLEELNLSKCESLVTLP SSIQNAIKLRTLYCSGVLLIDLKSLEGMCNLEYLSVDWSSMEG TQGLIYLPRKLKRLWWDYCPVKRLPSNFKAEYLVELRMENSD LEKLWDGTQPLGSLKEMYLHGSKYLKEIPDLSLAINLERLYLF GCESLVTLPSSIQNATKLINLDMRDCKKLESFPTDLNLESLEYL NLTGCPNLRNFPAIKMGCSYFEILQDRNEIEVEDCFWNKNLPA GLDYLDCLMRCMPCEFRPEYLTFLDVSGCKHEKLWEGIQIHA LLDGYELAGHLDGSIETPAPTLTTNNVVSANPQYTLWKRQDR LIFSALIGAISPPVQPLVSRATKASQIWKTLTNTYAKSSYDHIKQ LRTQIKQLLKKGTKTIDEYVLSHTTLLDQLAILGKPMEHIEEQVE RILEGLPEDYKTVVDQIEGKDNTPSITEIHERLINHEAKLLSTAA LSSSSLPMSANVAQQRHHNNNRNNNQNKNRTQGNTYTNWW QPSANNKSGQRPFKPYLGKCQICNVQGHSARRCPQLQAMQPS SSSSASTFTPWQPRANLAMGAPYTANNWLLDSGATHHITSDL NALALHQPYNGDDVMIADGTSLKITKTGSTFLPSNARDLTLNK VLYVPDIQKNLVSVYRLCNTNQVSVEFFPASFQVKDLNTGTLL LQGRTKDELYEWPVTNPKATALFTTPSPKTTLSSWHSRLGHPS SSILNTLISKFSLPVSVSASNKLACSDCFINKSHKLPFSISSIKSTS PLEYIFSDVWMSPILSPDNYKYYLQKSQVKSTFIAFKALVENRF QAKIRTLYSDNGGEFIALREFLVSNGISHLTSPPHTPEHNGLSER KHRHIVETGLTLLTQASVPREYWPYAFAAAVYLINRMPTPVLS MESPFQKLFGSKPNYERLRVFGCLCFPWLRPYTHNKLEERSRR CVFLGYSTQAYLCFDVEHKRLYTSRHVVFDEASFPSNLTSQ NSLPTVTFEQSSSPLVTPILSSSSVLPSCLSSPCTVLHQQQPPVTT PNSPHSSQPTTSPAPLSPHRSTTMDFQVPQPTAPNENGPEPEAQ SPPIGPLSNPTHEAFIGPLPNPNRNPTNEIEPTPAPHPKPVKPTTT TTTPNRTTVSDASHQPTAPQQNQHNMKTRAKNNIKPNTKFS LTATLPNRSPSEPTNVTQALKDKKWRFAMSDEFDAQQRNHT WDLVPHESQLLVGCKWVFKLKYLPNGAIDKYKARLVAKGFN QQYGVDYAETFSPVIKSTTIRLVLDVAVKKDWEIKQLDVNNA FLQGTLTEEVYMAQPPGFLDKDRPTHVCRLRKAIYGLKQAPRA WYMELKQHLFNIGFVNSLSDASLFIYWSDKSSIDAVLTSLAER FSIKDPTDLHYFLGIEATRTKQGLHLMQRKYIKDLLAKHNMA DAKPVLTPLPTSPKLTLHGGTKLNDASEYRSVVGSLQYLAFTR PDIAYAVNRLSQLMPQPTEDHWQAAKRVLRYLAGTSTHDWA GDSDDYVSTNAYVIYLGKNPISWSSKKQRGVARSSTESEYRA VANAASEVKWLCSLLSKLHIRLPIRPSIFCDNIGATYLCNAPVF HSRMKHIAIDYHFVRNMIQSGALRVSHVSTRDQLADALTKPLS RAHFQSARFKIGVRQLPPS |
| 254 | MSTSSLRRQMKNIVHNYSEAEIKVREATSNDPWGPSSSLMSEI ADLTYNVVAFSEIMSMIWKRLNDHGKNWRHVYKAMTLMEY LIKTGSERVSQQCKENMYAVQTLKDFQYVDRDGKDQGVNVR EKAKQLVALLRDEDRLREERAHALKTKEKLAQTATASSAAVG SGPPPEAEQAWPQSSGEEELQLQLALAMSKEEADQPPSCGPED DVQLQLALSLSREEHDKEERIRRGDDLRLQMAIEESKRETGGK EESSLMDLADVFTTPAPPQASDPWGGPASVPTAVPVAAAASD PWGAPAVPPAADPWGGAAPTPASGDPWRPAAPTGPSVDPWG GTPAPAAGEGPTSDPWGSADGGAPVSGPPSSDPWAPAPAFSDP WGGSPAKPSSNGTAVGGFDTEPDEFSDFDRLRTALPTSGSSTG ELELLAGEVPARSPGAFDMSGVGGSLAESVGSPPPAATPTPTPP TRKTPESFLGPNAALVDLDSLVSRPGPTPPGAKASNPFLPSGAP ATGPSVTNPFQPAPPATLTLNQLRLSPVPPVPGAPPTYISPLGG GPGLPPMMPPGPPAPNTNPFLL |
| 255 | MEPPLPVGAQPLATVEGMEMKGPLREPCALTLAQRNGQYELII QLHEKEQHVQDIIPINSHFRCVQEAEETLLIDIASNSGCKIRVQG DWIRERRFEIPDEEHCLKFLSAVLAAQKAQSQLLVPEQKDSSS WYQKLDTKDKPSVFSGLLGFEDNFSSMNLDKKINSQNQPTGIH REPPPPPPFSVNKMLPREKEASNKEQPKVTNTMRKLFVPNTQSG QREGLIKHILAKREKEYVNIQTFRFFVGTWNVNGQSPDSGLEP WLNCDPNPPDIYCIGFQELDLSTEAEFYFESVKEQEWSMAVER GLHSKAKYKKVQLVRLVGMMLLIFARKDQCRYIRDIATETVG TGIMGKMGNKGGVAVRFVFHNTTFCIVNSHLAAHVEDFERRN QDYKDICARMSFVVPNQTLPQLNIMKHEVVIWGDLNYRLCMP DANEVKSLINKKDLQRLLKFDQLNIQRTQKKAFVDFNEGEIKF IPTYKYDSKTDRWDSSGKCRVPAWCDRILWRGTNVNQLNYR SHMELKTSDHKPVSALFHIGVKVVDERRYRKVFEDSVRIMDR MENDFLPSLELSRREFEVFENVKFRQLQKEKFQISNNGQVPCHF SFIPKLNDSQYCKPWLRAEPFEGYLEPNETVDISLDVYVSKDS VTLINSGEDKIEDILVLHLDRGKDYFLTISGNYLPSCFGTSLEAL CRMKRPIREVPVTKLIDLEEDSFLEKEKSLLQMVPLDEGASERP LQVPKEIWLLVDHLFKYACHQEDLFQTPGMQEELQQIIDCLDT SIPETIPGSNHSVAEALLIFLEALPEPVICYELYQRCLDSAYDPRI CRQVISQLPRCHRNVFRYLMAFLRELLKFSEYNSVNANMIATL FTSLLLRPPPNLMARQTPSDRQRAIQFLLGFLLGSEED |
| 256 | MSESGNTTSMPGCGRMCALRSTWSKRAFLVACKDGALTSDG RCPQYGCGALVSITKGVQQPKKTASAKVVKCLCWVQPARWC EKHSKGPASPNGSVTTKRSNSARAAPAPLPYKKQTCDVVVTV GPLELVYPALVSEELPTTVAATPTKVEEVPIPELPLWLAPAWM VEQPYAATPEVLCLTQREEFALLKKRLTRKGKLLQRRATHAR FEARAALARVRAATQRKVEEVTALVIKGRRILAAHQLLRELEE VAPLSQAQEQLVASSCAAAAARQEECASFLRRAKAWRKSISA TPPVAATAVASKKVVSATMPWAHLGLSLGGLLAVPTLDGTLGA KQWNAKTIATWVLKPVVSCVQSVHAKVRDWLHSQPEVGVT NTKVPLVLPEVCLGVLSPPSLSEEIVDNPQETSQSGIWHPEMGV RNIYVFHDDSWETSPEEDENYTYTFSRQCGIPYLLVEGRGAEE RKNTILGWDFSLHNDGFEFLPSPEEGYTKELVTPVALEEEDKY STASSCGFFSLDDVSSAITIQCPGLLSADADVHFFDGPGYRCSS RPRDFRPPVVRGCDYESRVKASIQRKIENPLQERFITVLREKRK KNKKKEFHSFSACFAFKRKQIQWPPTPNEMVNEWEEYCIAQA WLPFEVVVTDEIEDVTPLYPGGRDYNCNSQLLFPLAPLSTVYC DDSCFHPNDGWTTDGNGKHFRLSPQFVLPDVPIPIVHRVTRQL PQFLYDLGIGDLTCNSGYQAENLQEEIQERMEDRSEEKPVPSL DTLISKLSKRSTKVKGAGENRYADRHSLTEKAIFHQPGALSRM RSGKEKTIVAANHNSDQISVRMAECGKPVFTPLPRMSDEMLR KFLEKGLGSTSTVALDIGIQXSHIPQGMPTVAFVNVMDTRIEDPL YSSSLCGSYIDLGRDRAKTLCLPLVNFPMSKLAEDVDDVLNGL MLCTHFQDSTKFGVGKPAFQYGTLEFQEFKPSAYSDFSRVRD NWDAIAKQQNTPNDRILAGFSVLGAVSQAYNQALPVFKSVEL VAPPKRKPVVATFQNPTTLGRSNTTRSFRMPTMDLPRSTGRDA PIPIVHRRNNNDVHFDEATPARFSTCDSGLVADTTLAFAKMYQ CKKDAKAGHVLATIDIQECVFEDNRRVALDWLAHGLASFKY DLQLTVDSNPFVGVTLGITVDAFDRLLPQISDEVIAVPLAFQLP TYLFPISKKGFTFQTIDFAAIAGYNFFPHVAAFGRPKIIVYIVSD NDLPASDTWMCLVELHMTRLESSTLACSPTLVLPQAFGGDLP LDLWRGPYTFPLGGGTKRLSTSLDIGTSTTTVSGWRTVSPAAY ALFLGHGGSLVGEVVHTGSAAVSCALHLCISFGGAPPTLEEA LVFPGFRLPSGEGKFHIKVQTPYGRLSTLTPDCALYVYLAGGPI AVAPMSVPYQFCIHLERLVDDGAPPRTIGLIREFNWATINNFKS DDITFAIPARLSDLVLTCGDVTMSTNPLALLIGSCGFFRGNLTV VLEWATFLKAGDKEGTVQLTTCRGMINNVKGVRNAIQKKVV NLSLVGSVSRYLNVGDFTGFAQSGGQVGYDEIFLEFSTNKAKQ IRYLNINVELDENFELYGRTIIPLKNTAPAFASTSSAPNES |

The invention claimed is:

1. A method of treating a condition in an animal said method comprising the step of administering to said animal a composition comprising: a polypeptide comprising: SEQ ID NO: 1, said polypeptide optionally having one conservative amino acid substitution.

2. The method of claim 1 wherein said condition is pain.

3. The method of claim 2 wherein said pain is post-surgery pain.

4. The method of claim 1 wherein said condition is associated with a change in body temperature.

5. The method of claim 4 wherein said condition is fever.

6. The method of claim 1 wherein said polypeptide is between 3-50 amino acids in length.

7. The method of claim 1 wherein said polypeptide consists of SEQ ID NO: 1.

8. The method of claim 1 wherein said composition is formulated for being administered orally.

9. The method of claim 1 wherein said composition is formulated for being administered topically.

10. The method of claim 1 wherein said composition is formulated for being administered intravenously.

\* \* \* \* \*

SEQUENCE LISTING

<160> NUMBER OF SEQ ID NOS: 260

<210> SEQ ID NO 1
<211> LENGTH: 4
<212> TYPE: PRT
<213> ORGANISM: Unknown Organism
<220> FEATURE:
<223> OTHER INFORMATION: Description of Unknown Organism: Arabidopsis
      thaliana or Homo sapiens

<400> SEQUENCE: 1

Phe Leu Pro Ser
1

<210> SEQ ID NO 2
<211> LENGTH: 12
<212> TYPE: PRT
<213> ORGANISM: Arabidopsis thaliana

<400> SEQUENCE: 2

Phe Leu Pro Ser Glu Phe Gly Val Asp Val Asp Arg
1               5                   10

<210> SEQ ID NO 3
<211> LENGTH: 14
<212> TYPE: PRT
<213> ORGANISM: Arabidopsis thaliana

<400> SEQUENCE: 3

Lys Arg Phe Leu Pro Ser Glu Phe Gly Val Asp Val Asp Arg
1               5                   10

<210> SEQ ID NO 4
<211> LENGTH: 14
<212> TYPE: PRT
<213> ORGANISM: Zea mays

<400> SEQUENCE: 4

Lys Arg Phe Phe Pro Ser Glu Phe Gly Leu Asp Val Asp Arg
1               5                   10

<210> SEQ ID NO 5
<211> LENGTH: 14
<212> TYPE: PRT
<213> ORGANISM: Nicotiana tabacum

<400> SEQUENCE: 5

Lys Arg Phe Leu Pro Ser Glu Phe Gly Phe Asp Val Asp His
1               5                   10

<210> SEQ ID NO 6
<211> LENGTH: 14
<212> TYPE: PRT
<213> ORGANISM: Cryptomeria japonica

<400> SEQUENCE: 6

Lys Arg Phe Phe Pro Ser Glu Phe Gly Asn Asp Val Asp Lys
1               5                   10

<210> SEQ ID NO 7
<211> LENGTH: 14
<212> TYPE: PRT
<213> ORGANISM: Forsythia x intermedia

```
<400> SEQUENCE: 7

Lys Arg Phe Phe Pro Ser Glu Phe Gly Thr Asp Val Asp Arg
1               5                   10

<210> SEQ ID NO 8
<211> LENGTH: 14
<212> TYPE: PRT
<213> ORGANISM: Arabidopsis thaliana

<400> SEQUENCE: 8

Lys Arg Phe Leu Pro Ser Glu Phe Gly Met Asp Pro Pro Arg
1               5                   10

<210> SEQ ID NO 9
<211> LENGTH: 14
<212> TYPE: PRT
<213> ORGANISM: Lupinus albus

<400> SEQUENCE: 9

Lys Arg Phe Leu Pro Ser Glu Phe Gly Met Asp Pro Ala Leu
1               5                   10

<210> SEQ ID NO 10
<211> LENGTH: 14
<212> TYPE: PRT
<213> ORGANISM: Oryza sativa

<400> SEQUENCE: 10

Arg Arg Phe Leu Pro Ser Glu Phe Gly Leu Asp Pro Asp His
1               5                   10

<210> SEQ ID NO 11
<211> LENGTH: 14
<212> TYPE: PRT
<213> ORGANISM: Thuja plicata

<400> SEQUENCE: 11

Lys Arg Phe Leu Pro Ser Glu Phe Gly Met Asp Pro Asp Ile
1               5                   10

<210> SEQ ID NO 12
<211> LENGTH: 14
<212> TYPE: PRT
<213> ORGANISM: Arabidopsis thaliana

<400> SEQUENCE: 12

Lys Arg Phe Phe Pro Ser Glu Phe Gly Asn Asp Val Asp Arg
1               5                   10

<210> SEQ ID NO 13
<211> LENGTH: 14
<212> TYPE: PRT
<213> ORGANISM: Glycine max

<400> SEQUENCE: 13

Lys Lys Phe Tyr Pro Ser Glu Phe Gly Asn Asp Val Asp Arg
1               5                   10

<210> SEQ ID NO 14
<211> LENGTH: 15
<212> TYPE: PRT
<213> ORGANISM: Arabidopsis thaliana

<400> SEQUENCE: 14
```

```
Val Lys Arg Phe Phe Pro Ser Glu Phe Gly Leu Asp Val Asp Arg
1               5                   10                  15

<210> SEQ ID NO 15
<211> LENGTH: 5
<212> TYPE: PRT
<213> ORGANISM: Homo sapiens

<400> SEQUENCE: 15

Tyr Gly Gly Phe Leu
1               5

<210> SEQ ID NO 16
<211> LENGTH: 5
<212> TYPE: PRT
<213> ORGANISM: Homo sapiens

<400> SEQUENCE: 16

Tyr Gly Gly Phe Met
1               5

<210> SEQ ID NO 17
<211> LENGTH: 10
<212> TYPE: PRT
<213> ORGANISM: Homo sapiens

<400> SEQUENCE: 17

Tyr Gly Gly Phe Leu Arg Lys Tyr Pro Lys
1               5                   10

<210> SEQ ID NO 18
<211> LENGTH: 9
<212> TYPE: PRT
<213> ORGANISM: Homo sapiens

<400> SEQUENCE: 18

Tyr Gly Gly Pro Leu Arg Lys Tyr Pro
1               5

<210> SEQ ID NO 19
<211> LENGTH: 31
<212> TYPE: PRT
<213> ORGANISM: Homo sapiens

<400> SEQUENCE: 19

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 20
<211> LENGTH: 16
<212> TYPE: PRT
<213> ORGANISM: Homo sapiens

<400> SEQUENCE: 20

Tyr Gly Gly Phe Met Thr Ser Glu Lys Ser Gln Thr Pro Leu Val Thr
1               5                   10                  15

<210> SEQ ID NO 21
<211> LENGTH: 17
<212> TYPE: PRT
<213> ORGANISM: Homo sapiens

<400> SEQUENCE: 21
```

Tyr Gly Gly Phe Leu Arg Arg Ile Arg Pro Lys Leu Lys Trp Asp Asn
1               5                   10                  15

Gln

<210> SEQ ID NO 22
<211> LENGTH: 13
<212> TYPE: PRT
<213> ORGANISM: Homo sapiens

<400> SEQUENCE: 22

Tyr Gly Gly Phe Leu Arg Arg Gln Phe Lys Val Val Thr
1               5                   10

<210> SEQ ID NO 23
<211> LENGTH: 4
<212> TYPE: PRT
<213> ORGANISM: Homo sapiens

<400> SEQUENCE: 23

Tyr Pro Thr Phe
1

<210> SEQ ID NO 24
<211> LENGTH: 4
<212> TYPE: PRT
<213> ORGANISM: Homo sapiens

<400> SEQUENCE: 24

Tyr Pro Phe Phe
1

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Ala
<220> FEATURE:
<221> NAME/KEY: MOD_RES
<222> LOCATION: (4)
<223> OTHER INFORMATION: N-Methyl-Phe
<220> FEATURE:
<221> NAME/KEY: MOD_RES
<222> LOCATION: (5)
<223> OTHER INFORMATION: Gly-ol

<400> SEQUENCE: 25

Tyr Ala Gly Phe Gly
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pen
<220> FEATURE:
<221> NAME/KEY: MOD_RES

```
<222> LOCATION: (5)
<223> OTHER INFORMATION: D-Pen

<400> SEQUENCE: 26

Tyr Xaa Gly Phe Xaa
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pen
<220> FEATURE:
<221> NAME/KEY: MOD_RES
<222> LOCATION: (4)
<223> OTHER INFORMATION: D-Chloro-Phe
<220> FEATURE:
<221> NAME/KEY: MOD_RES
<222> LOCATION: (5)
<223> OTHER INFORMATION: D-Pen

<400> SEQUENCE: 27

Tyr Xaa Gly Phe Xaa
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Pen
<220> FEATURE:
<221> NAME/KEY: MOD_RES
<222> LOCATION: (4)..(5)
<223> OTHER INFORMATION: Pen

<400> SEQUENCE: 28

Tyr Xaa Gly Xaa Xaa
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Ser

<400> SEQUENCE: 29

Tyr Ser Gly Phe Leu Thr
1               5

<210> SEQ ID NO 30
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Ala
<220> FEATURE:
<221> NAME/KEY: MOD_RES
<222> LOCATION: (5)
<223> OTHER INFORMATION: D-Leu

<400> SEQUENCE: 30

Tyr Ala Gly Phe Leu
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Tyr Gly Gly Phe Met Arg Phe
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: D-Phe
<220> FEATURE:
<221> NAME/KEY: MOD_RES
<222> LOCATION: (4)
<223> OTHER INFORMATION: D-Trp
<220> FEATURE:
<221> NAME/KEY: MOD_RES
<222> LOCATION: (5)
<223> OTHER INFORMATION: Orn
<220> FEATURE:
<221> NAME/KEY: MOD_RES
<222> LOCATION: (7)
<223> OTHER INFORMATION: Pen

<400> SEQUENCE: 32

Phe Cys Tyr Trp Xaa Thr Xaa Thr
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Arg

<400> SEQUENCE: 33

Arg Tyr Arg Ile Lys
1               5
```

```
<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Arg

<400> SEQUENCE: 34

Tyr Arg Phe Lys
1

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Ala
<220> FEATURE:
<221> NAME/KEY: MOD_RES
<222> LOCATION: (4)
<223> OTHER INFORMATION: N-Methyl-Phe
<220> FEATURE:
<221> NAME/KEY: MOD_RES
<222> LOCATION: (5)
<223> OTHER INFORMATION: Gly-ol

<400> SEQUENCE: 35

Tyr Ala Gly Phe Gly
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Ala
<220> FEATURE:
<221> NAME/KEY: MOD_RES
<222> LOCATION: (5)
<223> OTHER INFORMATION: D-Leu
<220> FEATURE:
<221> NAME/KEY: MOD_RES
<222> LOCATION: (6)
<223> OTHER INFORMATION: D-Cys

<400> SEQUENCE: 36

Tyr Ala Gly Phe Leu Cys
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)
<223> OTHER INFORMATION: D-Ala
<220> FEATURE:
<221> NAME/KEY: MOD_RES
<222> LOCATION: (8)
<223> OTHER INFORMATION: Gly-amide

<400> SEQUENCE: 37

Tyr Ala Phe Glu Val Val Pro Gly
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Ala

<400> SEQUENCE: 38

Tyr Ala Phe Asp Val Val Gly
1               5

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Methyl-Phe
<220> FEATURE:
<221> NAME/KEY: MOD_RES
<222> LOCATION: (4)
<223> OTHER INFORMATION: D-Pro

<400> SEQUENCE: 39

Tyr Pro Phe Pro
1

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: N,N-diallyl-Tyr
<220> FEATURE:
<221> NAME/KEY: MOD_RES
<222> LOCATION: (2)..(3)
<223> OTHER INFORMATION: Aib

<400> SEQUENCE: 40

Tyr Xaa Xaa Phe Leu
1               5

<210> SEQ ID NO 41
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 41

Tyr Pro Phe Pro
1

<210> SEQ ID NO 42
<211> LENGTH: 17
<212> TYPE: PRT
<213> ORGANISM: Homo sapiens

<400> SEQUENCE: 42

Phe Gly Gly Phe Thr Gly Ala Arg Lys Ser Ala Arg Lys Leu Ala Asn
1               5                   10                  15

Gln

<210> SEQ ID NO 43
<211> LENGTH: 18
<212> TYPE: PRT
<213> ORGANISM: Homo sapiens

<400> SEQUENCE: 43

Thr Glu Pro Gly Leu Glu Glu Val Gly Glu Ile Glu Gly Gln Lys Gln
1               5                   10                  15

Leu Gln

<210> SEQ ID NO 44
<211> LENGTH: 18
<212> TYPE: PRT
<213> ORGANISM: Homo sapiens

<400> SEQUENCE: 44

Ala Gly Glu Gly Leu Asn Ser Gln Phe Trp Ser Leu Ala Ala Pro Gln
1               5                   10                  15

Arg Phe

<210> SEQ ID NO 45
<211> LENGTH: 11
<212> TYPE: PRT
<213> ORGANISM: Homo sapiens

<400> SEQUENCE: 45

Ser Gln Ala Phe Leu Phe Gln Pro Gln Arg Phe
1               5                   10

<210> SEQ ID NO 46
<211> LENGTH: 11
<212> TYPE: PRT
<213> ORGANISM: Homo sapiens

<400> SEQUENCE: 46

Arg Pro Lys Pro Gln Gln Phe Phe Gly Leu Met
1               5                   10

<210> SEQ ID NO 47
<211> LENGTH: 8
<212> TYPE: PRT
<213> ORGANISM: Homo sapiens

<400> SEQUENCE: 47
```

```
Tyr Pro Phe Val Glu Pro Ile Pro
1               5

<210> SEQ ID NO 48
<211> LENGTH: 7
<212> TYPE: PRT
<213> ORGANISM: Bovine

<400> SEQUENCE: 48

Tyr Pro Phe Pro Gly Pro Ile
1               5

<210> SEQ ID NO 49
<211> LENGTH: 42
<212> TYPE: PRT
<213> ORGANISM: Homo sapiens

<400> SEQUENCE: 49

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 50
<211> LENGTH: 6
<212> TYPE: PRT
<213> ORGANISM: Rattus sp.

<400> SEQUENCE: 50

Asn Pro Phe Leu Pro Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asn Pro Tyr Leu Pro Ser
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asn Pro Trp Leu Pro Ser
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 53

Asn Pro His Leu Pro Ser
1               5

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Pro Phe Leu Pro Ser
1               5

<210> SEQ ID NO 55
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asp Pro Tyr Leu Pro Ser
1               5

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Pro Trp Leu Pro Ser
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Pro His Leu Pro Ser
1               5

<210> SEQ ID NO 58
<211> LENGTH: 8
<212> TYPE: PRT
<213> ORGANISM: Arabidopsis thaliana

<400> SEQUENCE: 58

Phe Leu Pro Pro Pro Pro Ser Ser
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                peptide

<400> SEQUENCE: 59

Tyr Leu Pro Pro Pro Pro Ser Ser
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Trp Leu Pro Pro Pro Pro Ser Ser
1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

His Leu Pro Pro Pro Pro Ser Ser
1               5

<210> SEQ ID NO 62
<211> LENGTH: 6
<212> TYPE: PRT
<213> ORGANISM: Arabidopsis thaliana

<400> SEQUENCE: 62

Gly Ile Pro Tyr Thr Tyr
1               5

<210> SEQ ID NO 63
<211> LENGTH: 6
<212> TYPE: PRT
<213> ORGANISM: Thuja plicata

<400> SEQUENCE: 63

Ser Ile Pro Tyr Thr Tyr
1               5

<210> SEQ ID NO 64
<211> LENGTH: 6
<212> TYPE: PRT
<213> ORGANISM: Nicotiana tabacum

<400> SEQUENCE: 64

Thr Ile Pro Tyr Thr Tyr
1               5

<210> SEQ ID NO 65
<211> LENGTH: 6
<212> TYPE: PRT
<213> ORGANISM: Oryza sativa

<400> SEQUENCE: 65

Gly Val Pro Tyr Thr Tyr
1               5
```

```
<210> SEQ ID NO 66
<211> LENGTH: 6
<212> TYPE: PRT
<213> ORGANISM: Solanum tuberosum

<400> SEQUENCE: 66

Gly Ile Pro Phe Thr Tyr
1               5

<210> SEQ ID NO 67
<211> LENGTH: 6
<212> TYPE: PRT
<213> ORGANISM: Lupinus albus

<400> SEQUENCE: 67

Asn Ile Pro Phe Thr Tyr
1               5

<210> SEQ ID NO 68
<211> LENGTH: 6
<212> TYPE: PRT
<213> ORGANISM: Forsythia x intermedia

<400> SEQUENCE: 68

Gly Ile Pro Phe Thr Phe
1               5

<210> SEQ ID NO 69
<211> LENGTH: 6
<212> TYPE: PRT
<213> ORGANISM: Cryptomeria japonica

<400> SEQUENCE: 69

Gly Ile Pro His Thr Tyr
1               5

<210> SEQ ID NO 70
<211> LENGTH: 8
<212> TYPE: PRT
<213> ORGANISM: Arabidopsis thaliana

<400> SEQUENCE: 70

Tyr Thr Ile Lys Ala Val Asp Asp
1               5

<210> SEQ ID NO 71
<211> LENGTH: 8
<212> TYPE: PRT
<213> ORGANISM: Arabidopsis thaliana

<400> SEQUENCE: 71

Tyr Thr Ile Asn Ala Val Asp Asp
1               5

<210> SEQ ID NO 72
<211> LENGTH: 8
<212> TYPE: PRT
<213> ORGANISM: Nicotiana tabacum

<400> SEQUENCE: 72

Tyr Thr Ile Glu Ala Val Asp Asp
1               5

<210> SEQ ID NO 73
```

```
<211> LENGTH: 8
<212> TYPE: PRT
<213> ORGANISM: Glycine max

<400> SEQUENCE: 73

Tyr Thr Ile Asn Ser Val Asp Asp
1               5

<210> SEQ ID NO 74
<211> LENGTH: 8
<212> TYPE: PRT
<213> ORGANISM: Pisum sativum

<400> SEQUENCE: 74

Tyr Thr Ile Arg Ala Ala Asn Asp
1               5

<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Tyr Thr Ile Lys Thr Ile Asp Asp
1               5

<210> SEQ ID NO 76
<211> LENGTH: 8
<212> TYPE: PRT
<213> ORGANISM: Medicago truncatula

<400> SEQUENCE: 76

Phe Thr Ile Lys Ala Ala Asn Asp
1               5

<210> SEQ ID NO 77
<211> LENGTH: 8
<212> TYPE: PRT
<213> ORGANISM: Populus trichocarpa

<400> SEQUENCE: 77

Phe Thr Ile Lys Ala Val Asp Asp
1               5

<210> SEQ ID NO 78
<211> LENGTH: 16
<212> TYPE: PRT
<213> ORGANISM: Arabidopsis thaliana

<400> SEQUENCE: 78

Ser Phe Gly Val Glu Ala Ser Glu Leu Tyr Pro Asp Val Lys Tyr Thr
1               5                   10                  15

<210> SEQ ID NO 79
<211> LENGTH: 16
<212> TYPE: PRT
<213> ORGANISM: Populus trichocarpa

<400> SEQUENCE: 79

Ser Trp Gly Leu Glu Ala Ser Glu Leu Tyr Pro Asp Val Lys Tyr Thr
1               5                   10                  15
```

```
<210> SEQ ID NO 80
<211> LENGTH: 16
<212> TYPE: PRT
<213> ORGANISM: Pyrus communis

<400> SEQUENCE: 80

Ser Phe Gly Val Glu Ala Thr Ala Leu Tyr Pro Asp Val Lys Tyr Thr
1               5                   10                  15

<210> SEQ ID NO 81
<211> LENGTH: 7
<212> TYPE: PRT
<213> ORGANISM: Arabidopsis thaliana

<400> SEQUENCE: 81

His Ala Val Phe Val Asn Gly
1               5

<210> SEQ ID NO 82
<211> LENGTH: 7
<212> TYPE: PRT
<213> ORGANISM: Arabidopsis thaliana

<400> SEQUENCE: 82

His Cys Val Phe Val Lys Gly
1               5

<210> SEQ ID NO 83
<211> LENGTH: 7
<212> TYPE: PRT
<213> ORGANISM: Nicotiana tabacum

<400> SEQUENCE: 83

His Ser Val Phe Val Asn Gly
1               5

<210> SEQ ID NO 84
<211> LENGTH: 7
<212> TYPE: PRT
<213> ORGANISM: Glycine max

<400> SEQUENCE: 84

His Ser Ala Phe Val Lys Gly
1               5

<210> SEQ ID NO 85
<211> LENGTH: 7
<212> TYPE: PRT
<213> ORGANISM: Zea mays

<400> SEQUENCE: 85

His Ala Ala Phe Val Arg Gly
1               5

<210> SEQ ID NO 86
<211> LENGTH: 7
<212> TYPE: PRT
<213> ORGANISM: Oryza sativa

<400> SEQUENCE: 86

His Ala Gly Tyr Ile Arg Gly
1               5

<210> SEQ ID NO 87
<211> LENGTH: 7
```

```
<212> TYPE: PRT
<213> ORGANISM: Solanum tuberosum

<400> SEQUENCE: 87

His Thr Ala Phe Val Lys Gly
1               5

<210> SEQ ID NO 88
<211> LENGTH: 7
<212> TYPE: PRT
<213> ORGANISM: Glycine max

<400> SEQUENCE: 88

His Ser Ser Tyr Val Lys Gly
1               5

<210> SEQ ID NO 89

<400> SEQUENCE: 89

000

<210> SEQ ID NO 90
<211> LENGTH: 12
<212> TYPE: PRT
<213> ORGANISM: Arabidopsis thaliana

<400> SEQUENCE: 90

Asp Phe Thr Ser Phe Thr Ile Asp Pro Ser Phe Gly
1               5                   10

<210> SEQ ID NO 91
<211> LENGTH: 16
<212> TYPE: PRT
<213> ORGANISM: Arabidopsis thaliana

<400> SEQUENCE: 91

Cys Phe Ala Gly Leu Phe Leu Phe Val Pro Cys Leu Gly Gly Cys His
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Cys Gly Gly Leu Cys Pro Val Phe Leu Phe Leu Gly Ala Phe Cys
1               5                   10                  15

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ala Phe Tyr Ala Ala Phe Cys
1               5

<210> SEQ ID NO 94
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Phe Ser Pro Asp Ile Thr Phe Ser Thr Phe Asp
1               5                   10

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Thr Leu Phe Tyr Gly Ala Phe Cys
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Pro Leu Ser Tyr Gly Ala Phe Phe
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Pro Leu Ser Tyr Gly Gly Phe Tyr
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ala Phe Tyr Gly Ala Phe Met
1               5

<210> SEQ ID NO 99
<211> LENGTH: 8
<212> TYPE: PRT
<213> ORGANISM: Arabidopsis thaliana

<400> SEQUENCE: 99

Phe Phe Ala Gly Tyr Phe Leu Pro
1               5
```

```
<210> SEQ ID NO 100
<211> LENGTH: 8
<212> TYPE: PRT
<213> ORGANISM: Arabidopsis thaliana

<400> SEQUENCE: 100

Cys Phe Gly Gly Tyr Tyr Leu Pro
1               5

<210> SEQ ID NO 101
<211> LENGTH: 8
<212> TYPE: PRT
<213> ORGANISM: Arabidopsis thaliana

<400> SEQUENCE: 101

Cys Phe Ala Ala Tyr Phe Ala Gly
1               5

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Cys Phe Ala Gly Tyr Phe Leu Thr
1               5

<210> SEQ ID NO 103
<211> LENGTH: 8
<212> TYPE: PRT
<213> ORGANISM: Solanum tuberosum

<400> SEQUENCE: 103

Phe Phe Ala Gly Tyr Ser Leu Pro
1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Tyr Phe Gly Gly Tyr Ser Leu Pro
1               5

<210> SEQ ID NO 105
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met Phe Ala Gly Tyr Phe Ala Gly
1               5

<210> SEQ ID NO 106
<211> LENGTH: 8
<212> TYPE: PRT
<213> ORGANISM: Oryza sativa
```

<400> SEQUENCE: 106

Tyr Phe Ala Gly Tyr Ala Leu Pro
1               5

<210> SEQ ID NO 107
<211> LENGTH: 8
<212> TYPE: PRT
<213> ORGANISM: Nicotiana tabacum

<400> SEQUENCE: 107

Trp Phe Ala Asp Phe Phe Leu Pro
1               5

<210> SEQ ID NO 108
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Pro Leu Phe Tyr Gly Ala Phe Phe
1               5

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Leu Tyr Tyr Gly Gly Phe Cys
1               5

<210> SEQ ID NO 110
<211> LENGTH: 9
<212> TYPE: PRT
<213> ORGANISM: Arabidopsis thaliana

<400> SEQUENCE: 110

Thr Gly Tyr Ile Gly Lys Phe Leu Val
1               5

<210> SEQ ID NO 111
<211> LENGTH: 9
<212> TYPE: PRT
<213> ORGANISM: Glycine max

<400> SEQUENCE: 111

Thr Gly Tyr Ile Gly Lys Phe Ile Val
1               5

<210> SEQ ID NO 112
<211> LENGTH: 9
<212> TYPE: PRT
<213> ORGANISM: Forsythia x intermedia

<400> SEQUENCE: 112

Thr Gly Tyr Ile Gly Lys Phe Val Ala
1               5

```
<210> SEQ ID NO 113
<211> LENGTH: 9
<212> TYPE: PRT
<213> ORGANISM: Arabidopsis thaliana

<400> SEQUENCE: 113

Thr Gly Tyr Ile Gly Lys Tyr Ile Val
1               5

<210> SEQ ID NO 114
<211> LENGTH: 9
<212> TYPE: PRT
<213> ORGANISM: Nicotiana sylvestris

<400> SEQUENCE: 114

Thr Gly Tyr Ile Gly Lys Tyr Leu Val
1               5

<210> SEQ ID NO 115
<211> LENGTH: 8
<212> TYPE: PRT
<213> ORGANISM: Oryza sativa

<400> SEQUENCE: 115

Thr Gly Tyr Ile Gly Arg His Val
1               5

<210> SEQ ID NO 116
<211> LENGTH: 8
<212> TYPE: PRT
<213> ORGANISM: Zea mays

<400> SEQUENCE: 116

Thr Gly Tyr Leu Gly Arg His Val
1               5

<210> SEQ ID NO 117
<211> LENGTH: 9
<212> TYPE: PRT
<213> ORGANISM: Thuja plicata

<400> SEQUENCE: 117

Thr Gly Tyr Ile Gly Lys Arg Ile Val
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Gly Phe Ile Gly Lys Arg Ile Val
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119
```

```
Val Leu Phe Lys Gly Ile Tyr Gly Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Val Ile Phe Lys Gly Ile Tyr Gly Thr
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ala Val Phe Lys Gly Ile Tyr Gly Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Val Ile Tyr Lys Gly Ile Tyr Gly Thr
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Val Leu Tyr Lys Gly Ile Tyr Gly Thr
1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Val His Arg Gly Ile Tyr Gly Thr
1               5

<210> SEQ ID NO 125
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 125

Val His Arg Gly Leu Tyr Gly Thr
1               5

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Tyr Lys Val Asp Pro Tyr Leu Glu Ser Ala Glu Val Gly Phe Ser
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Thr Tyr Lys Val Asp Pro Tyr Leu Glu Ser Ala Glu Leu Gly Trp Ser
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Thr Tyr Lys Val Asp Pro Tyr Leu Ala Thr Ala Glu Val Gly Phe Ser
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Tyr Lys Val Asp Pro Tyr Leu Glu Ser Ala Glu Val Gly Phe Ser
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Thr Tyr Lys Val Asp Pro Tyr Leu Glu Ser Ala Glu Leu Gly Trp Ser
1               5                   10                  15
```

```
<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Thr Tyr Lys Val Asp Pro Tyr Leu Ala Thr Ala Glu Val Gly Phe Ser
1               5                   10                  15

<210> SEQ ID NO 132
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Lys Ile Tyr Leu Ile Lys
1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Lys Ile Tyr Leu Val Lys
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Arg Ile Tyr Leu Ile Lys
1               5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Arg Ile Tyr Leu Val Lys
1               5

<210> SEQ ID NO 136
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136
```

```
Lys Ile Leu Tyr Ile Lys
1               5

<210> SEQ ID NO 137
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Lys Val Leu Tyr Ile Lys
1               5

<210> SEQ ID NO 138
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Lys Val Leu Tyr Ile Arg
1               5

<210> SEQ ID NO 139
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ile Lys Lys Glu Trp Leu
1               5

<210> SEQ ID NO 140
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Lys Asn Glu Trp Leu
1               5

<210> SEQ ID NO 141
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Lys Lys Glu Trp Leu
1               5

<210> SEQ ID NO 142
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 142

Leu Lys Glu Trp Ile
1               5

<210> SEQ ID NO 143
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ile Lys Asp Glu Trp Leu
1               5

<210> SEQ ID NO 144
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ile Lys Gly Glu Trp Leu
1               5

<210> SEQ ID NO 145
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile Leu Glu Glu Trp Lys
1               5

<210> SEQ ID NO 146
<211> LENGTH: 6
<212> TYPE: PRT
<213> ORGANISM: Betula pendula

<400> SEQUENCE: 146

Leu Trp Glu Lys Lys Ile
1               5

<210> SEQ ID NO 147
<211> LENGTH: 6
<212> TYPE: PRT
<213> ORGANISM: Forsythia x intermedia

<400> SEQUENCE: 147

Leu Trp Glu Asn Lys Ile
1               5

<210> SEQ ID NO 148
<211> LENGTH: 6
<212> TYPE: PRT
<213> ORGANISM: Solanum tuberosum
```

-continued

```
<400> SEQUENCE: 148

Leu Trp Glu Lys Lys Thr
1               5

<210> SEQ ID NO 149
<211> LENGTH: 5
<212> TYPE: PRT
<213> ORGANISM: Arabidopsis thaliana

<400> SEQUENCE: 149

Ile Trp Glu Lys Leu
1               5

<210> SEQ ID NO 150
<211> LENGTH: 6
<212> TYPE: PRT
<213> ORGANISM: Nicotiana sylvestris

<400> SEQUENCE: 150

Leu Trp Glu Asp Lys Ile
1               5

<210> SEQ ID NO 151
<211> LENGTH: 6
<212> TYPE: PRT
<213> ORGANISM: Glycine max

<400> SEQUENCE: 151

Leu Trp Glu Gly Lys Ile
1               5

<210> SEQ ID NO 152
<211> LENGTH: 6
<212> TYPE: PRT
<213> ORGANISM: Lupinus albus

<400> SEQUENCE: 152

Lys Trp Glu Glu Leu Ile
1               5

<210> SEQ ID NO 153
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ser Pro Leu Phe
1

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Arg Asp Val Asp Val Gly Phe Glu Ser Pro Leu Phe Arg Lys
1               5                   10

<210> SEQ ID NO 155
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Pro Phe Pro Tyr
1

<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ser Pro Leu Phe Pro Asn
1               5

<210> SEQ ID NO 157
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ser Pro Leu Tyr Pro Asn
1               5

<210> SEQ ID NO 158
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Pro Leu Trp Pro Asn
1               5

<210> SEQ ID NO 159
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ser Pro Leu His Pro Asn
1               5

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160
```

```
Ser Pro Leu Phe Pro Asp
1               5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ser Pro Leu Tyr Pro Asp
1               5

<210> SEQ ID NO 162
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ser Pro Leu Trp Pro Asp
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Pro Leu His Pro Asp
1               5

<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ser Ser Pro Pro Pro Pro Leu Phe
1               5

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ser Ser Pro Pro Pro Pro Leu Tyr
1               5

<210> SEQ ID NO 166
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 166

Ser Ser Pro Pro Pro Pro Leu Trp
1               5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ser Ser Pro Pro Pro Pro Leu His
1               5

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Thr Tyr Pro Ile Gly
1               5

<210> SEQ ID NO 169
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Tyr Thr Tyr Pro Ile Ser
1               5

<210> SEQ ID NO 170
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Tyr Thr Tyr Pro Ile Thr
1               5

<210> SEQ ID NO 171
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Tyr Thr Tyr Pro Val Gly
1               5
```

```
<210> SEQ ID NO 172
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Tyr Thr Phe Pro Ile Gly
1               5

<210> SEQ ID NO 173
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Tyr Thr Phe Pro Ile Asn
1               5

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Phe Thr Phe Pro Ile Gly
1               5

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Tyr Thr His Pro Ile Gly
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Asp Asp Val Ala Lys Ile Thr Tyr
1               5

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177
```

```
Asp Asp Val Ala Asn Ile Thr Tyr
1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Asp Val Ala Glu Ile Thr Tyr
1               5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Asp Val Ser Asn Ile Thr Tyr
1               5

<210> SEQ ID NO 180
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Asp Asn Ala Ala Arg Ile Thr Tyr
1               5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asp Asp Ile Thr Lys Ile Thr Tyr
1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Asn Ala Ala Lys Ile Thr Phe
1               5

<210> SEQ ID NO 183
<211> LENGTH: 7
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 183

Gly Asn Val Phe Val Ala His
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gly Lys Val Phe Val Cys His
1               5

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Gly Asn Val Phe Val Ser His
1               5

<210> SEQ ID NO 186
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Lys Val Phe Ala Ser His
1               5

<210> SEQ ID NO 187
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly Val Phe Ala Ala His
1               5

<210> SEQ ID NO 188
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gly Arg Ile Tyr Gly Ala His
1               5
```

```
<210> SEQ ID NO 189
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Gly Lys Val Phe Ala Thr His
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Lys Val Tyr Ser Ser His
1               5

<210> SEQ ID NO 191
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Lys Val Tyr Ser Ser His
1               5

<210> SEQ ID NO 192
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Cys Phe Ala Tyr Phe Ala Gly
1               5

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196
```

```
<400> SEQUENCE: 196

000

<210> SEQ ID NO 197
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Pro Leu Phe Tyr Gly Ala Phe Phe
1               5

<210> SEQ ID NO 198
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Pro Leu Tyr Tyr Gly Gly Phe Cys
1               5

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Ala Phe Tyr Ala Ala Phe Cys
1               5

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 204

Pro Leu Ala Tyr Gly Ala Phe Tyr
1               5

<210> SEQ ID NO 205
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Pro Leu Phe Phe Asp Ala Phe Trp
1               5

<210> SEQ ID NO 206
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Phe Phe Ala Gly Tyr Phe Pro Leu
1               5

<210> SEQ ID NO 207

<400> SEQUENCE: 207

000

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Val Leu Phe Lys Gly Ile Tyr Gly Thr
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Val Ile Phe Lys Gly Ile Tyr Gly Thr
1               5

<210> SEQ ID NO 210
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 210

Ala Val Phe Lys Gly Ile Tyr Thr Gly
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Val Ile Tyr Lys Gly Ile Tyr Gly Thr
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Val Leu Tyr Lys Gly Ile Tyr Gly Thr
1               5

<210> SEQ ID NO 213
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Val His Arg Gly Ile Tyr Gly Thr
1               5

<210> SEQ ID NO 214
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Val His Arg Gly Leu Tyr Gly Thr
1               5

<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Val Ile Arg Lys Gly Ile Tyr Gly Thr
1               5
```

```
<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Val Ile Arg Lys Gly Ile Phe Gly Thr
1               5

<210> SEQ ID NO 217
<211> LENGTH: 9
<212> TYPE: PRT
<213> ORGANISM: Arabidopsis thaliana

<400> SEQUENCE: 217

Thr Gly Tyr Ile Gly Lys Phe Leu Val
1               5

<210> SEQ ID NO 218
<211> LENGTH: 9
<212> TYPE: PRT
<213> ORGANISM: Arabidopsis thaliana

<400> SEQUENCE: 218

Thr Gly Tyr Ile Gly Lys Phe Ile Val
1               5

<210> SEQ ID NO 219
<211> LENGTH: 9
<212> TYPE: PRT
<213> ORGANISM: Forsythia x intermedia

<400> SEQUENCE: 219

Thr Gly Tyr Ile Gly Lys Phe Val Ala
1               5

<210> SEQ ID NO 220
<211> LENGTH: 9
<212> TYPE: PRT
<213> ORGANISM: Arabidopsis thaliana

<400> SEQUENCE: 220

Thr Gly Tyr Ile Gly Lys Tyr Ile Val
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Thr Gly Tyr Ile Gly Lys Tyr Leu Val
1               5

<210> SEQ ID NO 222
<211> LENGTH: 8
<212> TYPE: PRT
<213> ORGANISM: Zea mays

<400> SEQUENCE: 222
```

-continued

Thr Gly Tyr Ile Gly Arg His Val
1               5

<210> SEQ ID NO 223
<211> LENGTH: 8
<212> TYPE: PRT
<213> ORGANISM: Oryza sativa

<400> SEQUENCE: 223

Thr Gly Tyr Leu Gly Arg His Val
1               5

<210> SEQ ID NO 224
<211> LENGTH: 6
<212> TYPE: PRT
<213> ORGANISM: Arabidopsis thaliana

<400> SEQUENCE: 224

Lys Ile Leu Tyr Ile Lys
1               5

<210> SEQ ID NO 225
<211> LENGTH: 6
<212> TYPE: PRT
<213> ORGANISM: Zea mays

<400> SEQUENCE: 225

Lys Val Leu Tyr Ile Lys
1               5

<210> SEQ ID NO 226
<211> LENGTH: 6
<212> TYPE: PRT
<213> ORGANISM: Glycine max

<400> SEQUENCE: 226

Lys Ile Leu Tyr Ile Arg
1               5

<210> SEQ ID NO 227
<211> LENGTH: 6
<212> TYPE: PRT
<213> ORGANISM: Pyrus communis

<400> SEQUENCE: 227

Lys Val Leu Tyr Ile Arg
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Lys Ile Tyr Leu Ile Arg
1               5

<210> SEQ ID NO 229
<211> LENGTH: 6
<212> TYPE: PRT
<213> ORGANISM: Artificial Sequence
<220> FEATURE:
<223> OTHER INFORMATION: Description of Artificial Sequence: Synthetic -continued

```
      peptide

<400> SEQUENCE: 229

Lys Ile Tyr Leu Val Lys
1               5

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Arg Ile Tyr Leu Val Lys
1               5

<210> SEQ ID NO 231
<211> LENGTH: 6
<212> TYPE: PRT
<213> ORGANISM: Arabidopsis thaliana

<400> SEQUENCE: 231

Leu Trp Glu Lys Lys Ile
1               5

<210> SEQ ID NO 232
<211> LENGTH: 6
<212> TYPE: PRT
<213> ORGANISM: Zea mays

<400> SEQUENCE: 232

Leu Trp Glu Asn Lys Ile
1               5

<210> SEQ ID NO 233
<211> LENGTH: 6
<212> TYPE: PRT
<213> ORGANISM: Arabidopsis thaliana

<400> SEQUENCE: 233

Leu Trp Glu Lys Lys Thr
1               5

<210> SEQ ID NO 234
<211> LENGTH: 5
<212> TYPE: PRT
<213> ORGANISM: Arabidopsis thaliana

<400> SEQUENCE: 234

Ile Trp Glu Lys Leu
1               5

<210> SEQ ID NO 235
<211> LENGTH: 6
<212> TYPE: PRT
<213> ORGANISM: Nicotiana sylvestris

<400> SEQUENCE: 235

Leu Trp Glu Asp Lys Ile
1               5

<210> SEQ ID NO 236
<211> LENGTH: 6
```

```
<212> TYPE: PRT
<213> ORGANISM: Glycine max

<400> SEQUENCE: 236

Leu Trp Glu Gly Lys Ile
1               5

<210> SEQ ID NO 237
<211> LENGTH: 6
<212> TYPE: PRT
<213> ORGANISM: Lupinus albus

<400> SEQUENCE: 237

Lys Trp Glu Glu Leu Ile
1               5

<210> SEQ ID NO 238
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ile Lys Lys Glu Trp Leu
1               5

<210> SEQ ID NO 239
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ile Lys Asn Glu Trp Leu
1               5

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Thr Lys Lys Glu Leu
1               5

<210> SEQ ID NO 241
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Leu Lys Glu Lys Leu
1               5

<210> SEQ ID NO 242
<211> LENGTH: 6
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 242

Ile Lys Asp Glu Trp Leu
1               5

<210> SEQ ID NO 243
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Ile Lys Gly Glu Trp Leu
1               5

<210> SEQ ID NO 244
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ile Leu Glu Glu Trp Lys
1               5

<210> SEQ ID NO 245
<211> LENGTH: 314
<212> TYPE: PRT
<213> ORGANISM: Arabidopsis thaliana

<400> SEQUENCE: 245

Met Asp Lys Lys Ser Arg Val Leu Ile Val Gly Gly Thr Gly Phe Ile
1               5                   10                  15

Gly Lys Arg Ile Val Lys Ala Ser Leu Ala Leu Gly His Pro Thr Tyr
            20                  25                  30

Val Leu Phe Arg Pro Glu Ala Leu Ser Tyr Ile Asp Lys Val Gln Met
        35                  40                  45

Leu Ile Ser Phe Lys Gln Leu Gly Ala Lys Leu Leu Glu Ala Ser Leu
    50                  55                  60

Asp Asp His Gln Gly Leu Val Asp Val Val Lys Gln Val Asp Val Val
65                  70                  75                  80

Ile Ser Ala Val Ser Gly Gly Leu Val Arg His His Ile Leu Asp Gln
                85                  90                  95

Leu Lys Leu Val Glu Ala Ile Lys Glu Ala Gly Asn Ile Lys Arg Phe
            100                 105                 110

Leu Pro Ser Glu Phe Gly Met Asp Pro Asp Val Val Glu Asp Pro Leu
        115                 120                 125

Glu Pro Gly Asn Ile Thr Phe Ile Asp Lys Arg Lys Val Arg Arg Ala
    130                 135                 140

Ile Glu Ala Ala Thr Ile Pro Tyr Thr Tyr Val Ser Ser Asn Met Phe
145                 150                 155                 160

Ala Gly Phe Phe Ala Gly Ser Leu Ala Gln Leu Gln Asp Ala Pro Arg
                165                 170                 175
```

```
Met Met Pro Ala Arg Asp Lys Val Leu Ile Tyr Gly Asp Gly Asn Val
            180                 185                 190

Lys Gly Val Tyr Val Asp Glu Asp Ala Gly Ile Tyr Ile Val Lys
        195                 200                 205

Ser Ile Asp Asp Pro Arg Thr Leu Asn Lys Thr Val Tyr Ile Arg Pro
    210                 215                 220

Pro Met Asn Ile Leu Ser Gln Lys Glu Val Val Glu Ile Trp Glu Arg
225                 230                 235                 240

Leu Ser Gly Leu Ser Leu Glu Lys Ile Tyr Val Ser Glu Asp Gln Leu
                245                 250                 255

Leu Asn Met Lys Asp Lys Ser Tyr Val Glu Lys Met Ala Arg Cys His
            260                 265                 270

Leu Tyr His Phe Phe Ile Lys Gly Asp Leu Tyr Asn Phe Glu Ile Gly
        275                 280                 285

Pro Asn Ala Thr Glu Gly Thr Lys Leu Tyr Pro Glu Val Lys Tyr Thr
    290                 295                 300

Thr Met Asp Ser Tyr Met Glu Arg Tyr Leu
305                 310

<210> SEQ ID NO 246
<211> LENGTH: 316
<212> TYPE: PRT
<213> ORGANISM: Arabidopsis thaliana

<400> SEQUENCE: 246

Met Gly Glu Ser Lys Arg Thr Glu Lys Thr Arg Val Leu Val Val Gly
1               5                   10                  15

Ala Thr Gly Tyr Ile Gly Lys Arg Ile Val Arg Ala Cys Leu Ala Glu
            20                  25                  30

Gly His Glu Thr Tyr Val Leu Gln Arg Pro Glu Ile Gly Leu Glu Ile
        35                  40                  45

Glu Lys Val Gln Leu Phe Leu Ser Phe Lys Lys Leu Gly Ala Arg Ile
    50                  55                  60

Val Glu Gly Ser Phe Ser Asp His Gln Ser Leu Val Ser Ala Val Lys
65                  70                  75                  80

Leu Val Asp Val Val Ser Ala Met Ser Gly Val His Phe Arg Ser
                85                  90                  95

His Asn Ile Leu Val Gln Leu Lys Leu Val Glu Ala Ile Lys Glu Ala
            100                 105                 110

Gly Asn Val Lys Arg Phe Leu Pro Ser Glu Phe Gly Met Asp Pro Pro
        115                 120                 125

Arg Met Gly His Ala Leu Pro Pro Gly Arg Glu Thr Phe Asp Gln Lys
    130                 135                 140

Met Glu Arg Gln Ala Ile Glu Ala Ala Gly Ile Pro Tyr Thr Tyr Val
145                 150                 155                 160

Val Gly Ala Cys Phe Ala Ala Tyr Phe Ala Gly Asn Leu Ser Gln Met
                165                 170                 175

Val Thr Leu Leu Pro Pro Lys Glu Lys Val Asn Ile Tyr Gly Asp Gly
            180                 185                 190

Asn Val Lys Val Val Phe Ala Asp Glu Asp Ile Ala Lys Tyr Thr
        195                 200                 205

Ala Lys Thr Leu Asn Asp Pro Arg Thr Leu Asn Lys Thr Val Asn Ile
    210                 215                 220

Arg Pro Pro Asp Asn Val Leu Thr Gln Leu Glu Leu Val Gln Ile Trp
225                 230                 235                 240
```

```
Glu Lys Leu Thr Gly Lys Glu Leu Glu Lys Thr Asn Ile Ala Ala Gln
                245                 250                 255

Asp Phe Leu Ala Asn Ile Glu Gln Met Glu Ile Pro His Gln Ala Gly
            260                 265                 270

Ile Gly His Phe Tyr His Ile Phe Tyr Glu Gly Cys Leu Thr Asp His
        275                 280                 285

Glu Val Gly Glu Asp Glu Ala Ser Ser Leu Tyr Pro Asp Val Lys
    290                 295                 300

Tyr Lys Arg Met Asp Asp Tyr Leu Arg Met Phe Leu
305                 310                 315

<210> SEQ ID NO 247
<211> LENGTH: 310
<212> TYPE: PRT
<213> ORGANISM: Arabidopsis thaliana

<400> SEQUENCE: 247

Met Ala Thr Glu Lys Ser Lys Ile Leu Val Ile Gly Gly Thr Gly Tyr
1               5                   10                  15

Ile Gly Lys Phe Leu Val Glu Ala Ser Ala Lys Ala Gly His Ser Thr
            20                  25                  30

Phe Ala Leu Val Arg Glu Ala Thr Leu Ser Asp Pro Val Lys Gly Lys
        35                  40                  45

Thr Val Gln Ser Phe Lys Asp Leu Gly Val Thr Ile Leu His Gly Asp
    50                  55                  60

Leu Asn Asp His Glu Ser Leu Val Lys Ala Ile Lys Gln Val Asp Val
65                  70                  75                  80

Val Ile Ser Thr Val Gly Ser Met Gln Ile Leu Asp Gln Thr Lys Ile
                85                  90                  95

Ile Ser Ala Ile Lys Glu Ala Gly Asn Val Lys Arg Phe Leu Pro Ser
            100                 105                 110

Glu Phe Gly Val Asp Val Asp Arg Thr Ser Ala Val Glu Pro Ala Lys
        115                 120                 125

Ser Ala Phe Ala Gly Lys Ile Gln Ile Arg Arg Thr Ile Glu Ala Glu
    130                 135                 140

Gly Ile Pro Tyr Thr Tyr Ala Val Thr Gly Cys Phe Gly Gly Tyr Tyr
145                 150                 155                 160

Leu Pro Thr Leu Val Gln Phe Glu Pro Gly Leu Thr Ser Pro Pro Arg
                165                 170                 175

Asp Lys Val Thr Ile Leu Gly Asp Gly Asn Ala Lys Ala Val Ile Asn
            180                 185                 190

Lys Glu Glu Asp Ile Ala Ala Tyr Thr Ile Lys Ala Val Asp Asp Pro
        195                 200                 205

Arg Thr Leu Asn Lys Ile Leu Tyr Ile Lys Pro Ser Asn Asn Thr Leu
    210                 215                 220

Ser Met Asn Glu Ile Val Thr Leu Trp Glu Lys Lys Ile Gly Lys Ser
225                 230                 235                 240

Leu Glu Lys Thr His Leu Pro Glu Glu Gln Leu Leu Lys Ser Ile Gln
                245                 250                 255

Glu Ser Pro Ile Pro Ile Asn Val Val Leu Ser Ile Asn His Ala Val
            260                 265                 270

Phe Val Asn Gly Asp Thr Asn Ile Ser Ile Glu Pro Ser Phe Gly Val
        275                 280                 285

Glu Ala Ser Glu Leu Tyr Pro Asp Val Lys Tyr Thr Ser Val Asp Glu
```

```
                290                 295                 300

Tyr Leu Ser Tyr Phe Ala
305                 310

<210> SEQ ID NO 248
<211> LENGTH: 13
<212> TYPE: PRT
<213> ORGANISM: Homo sapiens

<400> SEQUENCE: 248

Tyr Gly Gly Phe Leu Arg Arg Gln Phe Lys Val Val Thr
1               5                   10

<210> SEQ ID NO 249
<211> LENGTH: 74
<212> TYPE: PRT
<213> ORGANISM: Homo sapiens

<400> SEQUENCE: 249

Lys Tyr Pro Lys Arg Ser Ser Glu Val Ala Gly Glu Gly Asp Gly Asp
1               5                   10                  15

Ser Met Gly His Glu Asp Leu Tyr Lys Arg Tyr Gly Gly Phe Leu Arg
            20                  25                  30

Arg Ile Arg Pro Lys Leu Lys Trp Asp Asn Gln Lys Arg Tyr Gly Gly
        35                  40                  45

Phe Leu Arg Arg Gln Phe Lys Val Val Thr Arg Ser Gln Glu Asp Pro
    50                  55                  60

Asn Ala Tyr Ser Gly Glu Leu Phe Asp Ala
65                  70

<210> SEQ ID NO 250
<211> LENGTH: 253
<212> TYPE: PRT
<213> ORGANISM: Homo sapiens

<400> SEQUENCE: 250

Met Ala Trp Gln Gly Leu Val Leu Ala Ala Cys Leu Leu Met Phe Pro
1               5                   10                  15

Ser Thr Thr Ala Asp Cys Leu Ser Arg Cys Ser Leu Cys Ala Val Lys
            20                  25                  30

Thr Gln Asp Gly Pro Lys Pro Ile Asn Pro Leu Ile Cys Ser Leu Gln
        35                  40                  45

Cys Gln Ala Ala Leu Leu Pro Ser Glu Glu Trp Glu Arg Cys Gln Ser
    50                  55                  60

Phe Ser Phe Phe Thr Pro Ser Thr Leu Gly Leu Asn Asp Lys Glu Asp
65                  70                  75                  80

Leu Gly Ser Lys Ser Val Gly Glu Gly Pro Tyr Ser Glu Leu Ala Lys
                85                  90                  95

Leu Ser Gly Ser Phe Leu Lys Glu Leu Glu Lys Ser Lys Phe Leu Pro
            100                 105                 110

Ser Ile Ser Thr Lys Glu Asn Thr Leu Ser Lys Ser Leu Glu Glu Lys
        115                 120                 125

Leu Arg Gly Leu Ser Asp Gly Phe Arg Glu Gly Ala Glu Ser Glu Leu
    130                 135                 140

Met Arg Asp Ala Gln Leu Asn Asp Gly Ala Met Glu Thr Gly Thr Leu
145                 150                 155                 160

Tyr Leu Ala Glu Glu Asp Pro Lys Glu Gln Val Lys Arg Tyr Gly Gly
                165                 170                 175
```

```
Phe Leu Arg Lys Tyr Pro Lys Arg Ser Ser Glu Val Ala Gly Glu Gly
            180                 185                 190

Asp Gly Asp Ser Met Gly His Glu Asp Leu Tyr Lys Arg Tyr Gly Gly
        195                 200                 205

Phe Leu Arg Arg Ile Arg Pro Lys Leu Lys Trp Asp Asn Gln Lys Arg
    210                 215                 220

Tyr Gly Gly Phe Leu Arg Arg Gln Phe Lys Val Val Thr Arg Ser Gln
225                 230                 235                 240

Glu Asp Pro Asn Ala Tyr Ser Gly Glu Leu Phe Asp Ala
                245                 250

<210> SEQ ID NO 251
<211> LENGTH: 12
<212> TYPE: DNA
<213> ORGANISM: Arabidopsis thaliana

<400> SEQUENCE: 251
tttctgccct ca                                                          12

<210> SEQ ID NO 252
<211> LENGTH: 36
<212> TYPE: DNA
<213> ORGANISM: Arabidopsis thaliana

<400> SEQUENCE: 252
tttctgccct cagaatttgg agtagacgta gacaga                                36

<210> SEQ ID NO 253
<211> LENGTH: 2087
<212> TYPE: PRT
<213> ORGANISM: Arabidopsis thaliana

<400> SEQUENCE: 253

Met Val Lys Lys Ile Ala Asn Asp Val Ser Asn Lys Leu Phe Pro Leu
  1               5                  10                  15

Pro Lys Gly Phe Gly Asp Phe Val Gly Ile Glu Asp His Ile Lys Ala
             20                  25                  30

Ile Lys Ser Ile Leu Cys Leu Glu Ser Lys Glu Ala Arg Ile Met Val
         35                  40                  45

Gly Ile Trp Gly Gln Ser Gly Ile Gly Lys Ser Thr Ile Gly Arg Ala
     50                  55                  60

Leu Phe Ser Gln Leu Ser Ser Gln Phe His His Arg Ala Phe Ile Thr
 65                  70                  75                  80

Tyr Lys Ser Thr Ser Gly Ser Asp Val Ser Gly Met Lys Leu Ser Trp
                 85                  90                  95

Glu Lys Glu Leu Leu Ser Glu Ile Leu Gly Gln Lys Asp Ile Lys Ile
            100                 105                 110

Asp His Phe Gly Val Val Glu Gln Arg Leu Lys His Lys Lys Val Leu
        115                 120                 125

Ile Leu Leu Asp Asp Val Asp Asn Leu Glu Phe Leu Lys Thr Leu Val
    130                 135                 140

Gly Lys Ala Glu Trp Phe Gly Ser Gly Ser Arg Ile Ile Val Ile Thr
145                 150                 155                 160

Gln Asp Lys Gln Leu Leu Lys Ala His Glu Ile Asp Leu Val Tyr Glu
                165                 170                 175

Val Glu Leu Pro Ser Gln Gly Leu Ala Leu Lys Met Ile Ser Gln Tyr
            180                 185                 190
```

-continued

```
Ala Phe Gly Lys Asp Ser Pro Pro Asp Asp Phe Lys Glu Leu Ala Phe
            195                 200                 205
Glu Val Ala Glu Leu Val Gly Ser Leu Pro Leu Gly Leu Ser Val Leu
    210                 215                 220
Gly Ser Ser Leu Lys Gly Arg Asp Lys Asp Glu Trp Val Lys Met Met
225                 230                 235                 240
Pro Arg Leu Arg Asn Asp Ser Asp Lys Ile Glu Glu Thr Leu Arg
            245                 250                 255
Val Gly Tyr Asp Arg Leu Asn Lys Lys Asn Arg Asp Asn Val Lys Glu
            260                 265                 270
Leu Leu Glu Asp Asp Val Gly Leu Thr Met Leu Ala Asp Lys Ser Leu
    275                 280                 285
Ile Arg Ile Thr Pro Asp Gly Asp Ile Glu Met His Asn Leu Leu Glu
    290                 295                 300
Lys Leu Gly Arg Glu Ile Asp Arg Ala Lys Ser Lys Gly Asn Pro Ala
305                 310                 315                 320
Lys Arg Gln Phe Leu Thr Asn Phe Glu Asp Ile Gln Glu Val Val Thr
            325                 330                 335
Glu Lys Thr Gly Thr Glu Thr Val Leu Gly Ile Arg Val Pro Pro Thr
            340                 345                 350
Val Leu Phe Ser Thr Arg Pro Leu Leu Val Ile Asn Glu Glu Ser Phe
    355                 360                 365
Lys Gly Met Gln Ile Gly Leu Trp Ser Lys Ile Asp Leu Pro Gln Gly
    370                 375                 380
Leu Val Tyr Leu Pro Leu Lys Leu Lys Leu Leu Lys Trp Asn Tyr Cys
385                 390                 395                 400
Pro Leu Lys Ser Leu Pro Ser Thr Phe Lys Ala Glu Tyr Leu Val Asn
            405                 410                 415
Leu Ile Met Lys Tyr Ser Lys Leu Glu Lys Leu Trp Glu Gly Thr Leu
            420                 425                 430
Pro Leu Gly Ser Leu Lys Lys Met Asp Leu Gly Cys Ser Asn Asn Leu
    435                 440                 445
Lys Glu Ile Pro Asp Leu Ser Leu Ala Ile Asn Leu Glu Glu Leu Asn
    450                 455                 460
Leu Ser Lys Cys Glu Ser Leu Val Thr Leu Pro Ser Ser Ile Gln Asn
465                 470                 475                 480
Ala Ile Lys Leu Arg Thr Leu Tyr Cys Ser Gly Val Leu Leu Ile Asp
            485                 490                 495
Leu Lys Ser Leu Glu Gly Met Cys Asn Leu Glu Tyr Leu Ser Val Asp
            500                 505                 510
Trp Ser Ser Met Glu Gly Thr Gln Gly Leu Ile Tyr Leu Pro Arg Lys
    515                 520                 525
Leu Lys Arg Leu Trp Trp Asp Tyr Cys Pro Val Lys Arg Leu Pro Ser
    530                 535                 540
Asn Phe Lys Ala Glu Tyr Leu Val Glu Leu Arg Met Glu Asn Ser Asp
545                 550                 555                 560
Leu Glu Lys Leu Trp Asp Gly Thr Gln Pro Leu Gly Ser Leu Lys Glu
            565                 570                 575
Met Tyr Leu His Gly Ser Lys Tyr Leu Lys Glu Ile Pro Asp Leu Ser
            580                 585                 590
Leu Ala Ile Asn Leu Glu Arg Leu Tyr Leu Phe Gly Cys Glu Ser Leu
    595                 600                 605
```

-continued

```
Val Thr Leu Pro Ser Ser Ile Gln Asn Ala Thr Lys Leu Ile Asn Leu
    610                 615                 620

Asp Met Arg Asp Cys Lys Lys Leu Glu Ser Phe Pro Thr Asp Leu Asn
625                 630                 635                 640

Leu Glu Ser Leu Glu Tyr Leu Asn Leu Thr Gly Cys Pro Asn Leu Arg
                645                 650                 655

Asn Phe Pro Ala Ile Lys Met Gly Cys Ser Tyr Phe Glu Ile Leu Gln
                660                 665                 670

Asp Arg Asn Glu Ile Glu Val Glu Asp Cys Phe Trp Asn Lys Asn Leu
            675                 680                 685

Pro Ala Gly Leu Asp Tyr Leu Asp Cys Leu Met Arg Cys Met Pro Cys
    690                 695                 700

Glu Phe Arg Pro Glu Tyr Leu Thr Phe Leu Asp Val Ser Gly Cys Lys
705                 710                 715                 720

His Glu Lys Leu Trp Glu Gly Ile Gln Ile His Ala Leu Leu Asp Gly
                725                 730                 735

Tyr Glu Leu Ala Gly His Leu Asp Gly Ser Ile Glu Thr Pro Ala Pro
                740                 745                 750

Thr Leu Thr Thr Asn Asn Val Val Ser Ala Asn Pro Gln Tyr Thr Leu
            755                 760                 765

Trp Lys Arg Gln Asp Arg Leu Ile Phe Ser Ala Leu Ile Gly Ala Ile
    770                 775                 780

Ser Pro Pro Val Gln Pro Leu Val Ser Arg Ala Thr Lys Ala Ser Gln
785                 790                 795                 800

Ile Trp Lys Thr Leu Thr Asn Thr Tyr Ala Lys Ser Ser Tyr Asp His
                805                 810                 815

Ile Lys Gln Leu Arg Thr Gln Ile Lys Gln Leu Lys Lys Gly Thr Lys
            820                 825                 830

Thr Ile Asp Glu Tyr Val Leu Ser His Thr Thr Leu Leu Asp Gln Leu
    835                 840                 845

Ala Ile Leu Gly Lys Pro Met Glu His Glu Glu Gln Val Glu Arg Ile
850                 855                 860

Leu Glu Gly Leu Pro Glu Asp Tyr Lys Thr Val Val Asp Gln Ile Glu
865                 870                 875                 880

Gly Lys Asp Asn Thr Pro Ser Ile Thr Glu Ile His Glu Arg Leu Ile
                885                 890                 895

Asn His Glu Ala Lys Leu Leu Ser Thr Ala Ala Leu Ser Ser Ser Ser
                900                 905                 910

Leu Pro Met Ser Ala Asn Val Ala Gln Gln Arg His Asn Asn Asn Asn
    915                 920                 925

Arg Asn Asn Asn Gln Asn Lys Asn Arg Thr Gly Asn Thr Tyr Thr
930                 935                 940

Asn Asn Trp Gln Pro Ser Ala Asn Asn Lys Ser Gly Gln Arg Pro Phe
945                 950                 955                 960

Lys Pro Tyr Leu Gly Lys Cys Gln Ile Cys Asn Val Gln Gly His Ser
                965                 970                 975

Ala Arg Arg Cys Pro Gln Leu Gln Ala Met Gln Pro Ser Ser Ser Ser
            980                 985                 990

Ser Ala Ser Thr Phe Thr Pro Trp Gln Pro Arg Ala Asn Leu Ala Met
        995                 1000                1005

Gly Ala Pro Tyr Thr Ala Asn Asn Trp Leu Leu Asp Ser Gly Ala Thr
    1010                1015                1020

His His Ile Thr Ser Asp Leu Asn Ala Leu Ala Leu His Gln Pro Tyr
```

-continued

```
            1025                1030                1035                1040
Asn Gly Asp Asp Val Met Ile Ala Asp Gly Thr Ser Leu Lys Ile Thr
                1045                1050                1055
Lys Thr Gly Ser Thr Phe Leu Pro Ser Asn Ala Arg Asp Leu Thr Leu
            1060                1065                1070
Asn Lys Val Leu Tyr Val Pro Asp Ile Gln Lys Asn Leu Val Ser Val
        1075                1080                1085
Tyr Arg Leu Cys Asn Thr Asn Gln Val Ser Val Glu Phe Phe Pro Ala
    1090                1095                1100
Ser Phe Gln Val Lys Asp Leu Asn Thr Gly Thr Leu Leu Leu Gln Gly
1105                1110                1115                1120
Arg Thr Lys Asp Glu Leu Tyr Glu Trp Pro Val Thr Asn Pro Lys Ala
            1125                1130                1135
Thr Ala Leu Phe Thr Thr Pro Ser Pro Lys Thr Thr Leu Ser Ser Trp
        1140                1145                1150
His Ser Arg Leu Gly His Pro Ser Ser Ser Ile Leu Asn Thr Leu Ile
    1155                1160                1165
Ser Lys Phe Ser Leu Pro Val Ser Val Ser Ala Ser Asn Lys Leu Ala
1170                1175                1180
Cys Ser Asp Cys Phe Ile Asn Lys Ser His Lys Leu Pro Phe Ser Ile
1185                1190                1195                1200
Ser Ser Ile Lys Ser Thr Ser Pro Leu Glu Tyr Ile Phe Ser Asp Val
            1205                1210                1215
Trp Met Ser Pro Ile Leu Ser Pro Asp Asn Tyr Lys Tyr Tyr Leu Gln
        1220                1225                1230
Lys Ser Gln Val Lys Ser Thr Phe Ile Ala Phe Lys Ala Leu Val Glu
    1235                1240                1245
Asn Arg Phe Gln Ala Lys Ile Arg Thr Leu Tyr Ser Asp Asn Gly Gly
1250                1255                1260
Glu Phe Ile Ala Leu Arg Glu Phe Leu Val Ser Asn Gly Ile Ser His
1265                1270                1275                1280
Leu Thr Ser Pro Pro His Thr Pro Glu His Asn Gly Leu Ser Glu Arg
            1285                1290                1295
Lys His Arg His Ile Val Glu Thr Gly Leu Thr Leu Leu Thr Gln Ala
        1300                1305                1310
Ser Val Pro Arg Glu Tyr Trp Pro Tyr Ala Phe Ala Ala Ala Val Tyr
    1315                1320                1325
Leu Ile Asn Arg Met Pro Thr Pro Val Leu Ser Met Glu Ser Pro Phe
1330                1335                1340
Gln Lys Leu Phe Gly Ser Lys Pro Asn Tyr Glu Arg Leu Arg Val Phe
1345                1350                1355                1360
Gly Cys Leu Cys Phe Pro Trp Leu Arg Pro Tyr Thr His Asn Lys Leu
            1365                1370                1375
Glu Glu Arg Ser Arg Arg Cys Val Phe Leu Gly Tyr Ser Thr Gln Thr
        1380                1385                1390
Ala Tyr Leu Cys Phe Asp Val Glu His Lys Arg Leu Tyr Thr Ser Arg
    1395                1400                1405
His Val Val Phe Asp Glu Ala Ser Phe Pro Phe Ser Asn Leu Thr Ser
1410                1415                1420
Gln Asn Ser Leu Pro Thr Val Thr Phe Glu Gln Ser Ser Ser Pro Leu
1425                1430                1435                1440
Val Thr Pro Ile Leu Ser Ser Ser Ser Val Leu Pro Ser Cys Leu Ser
            1445                1450                1455
```

```
Ser Pro Cys Thr Val Leu His Gln Gln Gln Pro Pro Val Thr Thr Pro
        1460                1465                1470

Asn Ser Pro His Ser Ser Gln Pro Thr Thr Ser Pro Ala Pro Leu Ser
1475                1480                1485

Pro His Arg Ser Thr Thr Met Asp Phe Gln Val Pro Gln Pro Thr Ala
    1490                1495                1500

Pro Asn Glu Asn Gly Pro Glu Pro Glu Ala Gln Ser Pro Pro Ile Gly
1505                1510                1515                1520

Pro Leu Ser Asn Pro Thr His Glu Ala Phe Ile Gly Pro Leu Pro Asn
            1525                1530                1535

Pro Asn Arg Asn Pro Thr Asn Glu Ile Glu Pro Thr Pro Ala Pro His
        1540                1545                1550

Pro Lys Pro Val Lys Pro Thr Thr Thr Thr Thr Pro Asn Arg Thr
    1555                1560                1565

Thr Val Ser Asp Ala Ser His Gln Pro Thr Ala Pro Gln Gln Asn Gln
1570                1575                1580

His Asn Met Lys Thr Arg Ala Lys Asn Asn Ile Lys Lys Pro Asn Thr
1585                1590                1595                1600

Lys Phe Ser Leu Thr Ala Thr Leu Pro Asn Arg Ser Pro Ser Glu Pro
            1605                1610                1615

Thr Asn Val Thr Gln Ala Leu Lys Asp Lys Lys Trp Arg Phe Ala Met
        1620                1625                1630

Ser Asp Glu Phe Asp Ala Gln Gln Arg Asn His Thr Trp Asp Leu Val
    1635                1640                1645

Pro His Glu Ser Gln Leu Leu Val Gly Cys Lys Trp Val Phe Lys Leu
1650                1655                1660

Lys Tyr Leu Pro Asn Gly Ala Ile Asp Lys Tyr Lys Ala Arg Leu Val
1665                1670                1675                1680

Ala Lys Gly Phe Asn Gln Gln Tyr Gly Val Asp Tyr Ala Glu Thr Phe
            1685                1690                1695

Ser Pro Val Ile Lys Ser Thr Thr Ile Arg Leu Val Leu Asp Val Ala
        1700                1705                1710

Val Lys Lys Asp Trp Glu Ile Lys Gln Leu Asp Val Asn Asn Ala Phe
    1715                1720                1725

Leu Gln Gly Thr Leu Thr Glu Glu Val Tyr Met Ala Gln Pro Pro Gly
    1730                1735                1740

Phe Ile Asp Lys Asp Arg Pro Thr His Val Cys Arg Leu Arg Lys Ala
1745                1750                1755                1760

Ile Tyr Gly Leu Lys Gln Ala Pro Arg Ala Trp Tyr Met Glu Leu Lys
            1765                1770                1775

Gln His Leu Phe Asn Ile Gly Phe Val Asn Ser Leu Ser Asp Ala Ser
        1780                1785                1790

Leu Phe Ile Tyr Trp Ser Asp Lys Ser Ser Ile Asp Ala Val Leu Thr
    1795                1800                1805

Ser Leu Ala Glu Arg Phe Ser Ile Lys Asp Pro Thr Asp Leu His Tyr
1810                1815                1820

Phe Leu Gly Ile Glu Ala Thr Arg Thr Lys Gln Gly Leu His Leu Met
1825                1830                1835                1840

Gln Arg Lys Tyr Ile Lys Asp Leu Leu Ala Lys His Asn Met Ala Asp
            1845                1850                1855

Ala Lys Pro Val Leu Thr Pro Leu Pro Thr Ser Pro Lys Leu Thr Leu
        1860                1865                1870
```

His Gly Gly Thr Lys Leu Asn Asp Ala Ser Glu Tyr Arg Ser Val Val
            1875                1880                1885

Gly Ser Leu Gln Tyr Leu Ala Phe Thr Arg Pro Asp Ile Ala Tyr Ala
        1890                1895                1900

Val Asn Arg Leu Ser Gln Leu Met Pro Gln Pro Thr Glu Asp His Trp
1905                1910                1915                1920

Gln Ala Ala Lys Arg Val Leu Arg Tyr Leu Ala Gly Thr Ser Thr His
            1925                1930                1935

Asp Trp Ala Gly Asp Ser Asp Asp Tyr Val Ser Thr Asn Ala Tyr Val
        1940                1945                1950

Ile Tyr Leu Gly Lys Asn Pro Ile Ser Trp Ser Ser Lys Lys Gln Arg
            1955                1960                1965

Gly Val Ala Arg Ser Ser Thr Glu Ser Glu Tyr Arg Ala Val Ala Asn
    1970                1975                1980

Ala Ala Ser Glu Val Lys Trp Leu Cys Ser Leu Leu Ser Lys Leu His
1985                1990                1995                2000

Ile Arg Leu Pro Ile Arg Pro Ser Ile Phe Cys Asp Asn Ile Gly Ala
                2005                2010                2015

Thr Tyr Leu Cys Ala Asn Pro Val Phe His Ser Arg Met Lys His Ile
            2020                2025                2030

Ala Ile Asp Tyr His Phe Val Arg Asn Met Ile Gln Ser Gly Ala Leu
        2035                2040                2045

Arg Val Ser His Val Ser Thr Arg Asp Gln Leu Ala Asp Ala Leu Thr
    2050                2055                2060

Lys Pro Leu Ser Arg Ala His Phe Gln Ser Ala Arg Phe Lys Ile Gly
2065                2070                2075                2080

Val Arg Gln Leu Pro Pro Ser
            2085

<210> SEQ ID NO 254
<211> LENGTH: 575
<212> TYPE: PRT
<213> ORGANISM: Homo sapiens

<400> SEQUENCE: 254

Met Ser Thr Ser Ser Leu Arg Arg Gln Met Lys Asn Ile Val His Asn
1               5                   10                  15

Tyr Ser Glu Ala Glu Ile Lys Val Arg Glu Ala Thr Ser Asn Asp Pro
            20                  25                  30

Trp Gly Pro Ser Ser Ser Leu Met Ser Glu Ile Ala Asp Leu Thr Tyr
        35                  40                  45

Asn Val Val Ala Phe Ser Glu Ile Met Ser Met Ile Trp Lys Arg Leu
    50                  55                  60

Asn Asp His Gly Lys Asn Trp Arg His Val Tyr Lys Ala Met Thr Leu
65                  70                  75                  80

Met Glu Tyr Leu Ile Lys Thr Gly Ser Glu Arg Val Ser Gln Gln Cys
                85                  90                  95

Lys Glu Asn Met Tyr Ala Val Gln Thr Leu Lys Asp Phe Gln Tyr Val
            100                 105                 110

Asp Arg Asp Gly Lys Asp Gln Gly Val Asn Val Arg Glu Lys Ala Lys
        115                 120                 125

Gln Leu Val Ala Leu Leu Arg Asp Glu Asp Arg Leu Arg Glu Glu Arg
    130                 135                 140

Ala His Ala Leu Lys Thr Lys Glu Lys Leu Ala Gln Thr Ala Thr Ala
145                 150                 155                 160

-continued

```
Ser Ser Ala Ala Val Gly Ser Gly Pro Pro Glu Ala Glu Gln Ala
                165                 170                 175

Trp Pro Gln Ser Ser Gly Glu Glu Leu Gln Leu Gln Leu Ala Leu
            180                 185                 190

Ala Met Ser Lys Glu Glu Ala Asp Gln Pro Pro Ser Cys Gly Pro Glu
        195                 200                 205

Asp Asp Val Gln Leu Gln Leu Ala Leu Ser Leu Ser Arg Glu Glu His
    210                 215                 220

Asp Lys Glu Glu Arg Ile Arg Arg Gly Asp Asp Leu Arg Leu Gln Met
225                 230                 235                 240

Ala Ile Glu Glu Ser Lys Arg Glu Thr Gly Gly Lys Glu Glu Ser Ser
                245                 250                 255

Leu Met Asp Leu Ala Asp Val Phe Thr Thr Pro Ala Pro Pro Gln Ala
            260                 265                 270

Ser Asp Pro Trp Gly Pro Ala Ser Val Pro Thr Ala Val Pro Val
        275                 280                 285

Ala Ala Ala Ala Ser Asp Pro Trp Gly Ala Pro Ala Val Pro Pro Ala
    290                 295                 300

Ala Asp Pro Trp Gly Gly Ala Ala Pro Thr Pro Ala Ser Gly Asp Pro
305                 310                 315                 320

Trp Arg Pro Ala Ala Pro Thr Gly Pro Ser Val Asp Pro Trp Gly Gly
                325                 330                 335

Thr Pro Ala Pro Ala Ala Gly Glu Gly Pro Thr Ser Asp Pro Trp Gly
            340                 345                 350

Ser Ala Asp Gly Gly Ala Pro Val Ser Gly Pro Pro Ser Ser Asp Pro
        355                 360                 365

Trp Ala Pro Ala Pro Ala Phe Ser Asp Pro Trp Gly Gly Ser Pro Ala
    370                 375                 380

Lys Pro Ser Ser Asn Gly Thr Ala Val Gly Gly Phe Asp Thr Glu Pro
385                 390                 395                 400

Asp Glu Phe Ser Asp Phe Asp Arg Leu Arg Thr Ala Leu Pro Thr Ser
                405                 410                 415

Gly Ser Ser Thr Gly Glu Leu Glu Leu Leu Ala Gly Glu Val Pro Ala
            420                 425                 430

Arg Ser Pro Gly Ala Phe Asp Met Ser Gly Val Gly Gly Ser Leu Ala
        435                 440                 445

Glu Ser Val Gly Ser Pro Pro Ala Ala Thr Pro Thr Pro Thr Pro
    450                 455                 460

Pro Thr Arg Lys Thr Pro Glu Ser Phe Leu Gly Pro Asn Ala Ala Leu
465                 470                 475                 480

Val Asp Leu Asp Ser Leu Val Ser Arg Pro Gly Pro Thr Pro Pro Gly
                485                 490                 495

Ala Lys Ala Ser Asn Pro Phe Leu Pro Ser Gly Ala Pro Ala Thr Gly
            500                 505                 510

Pro Ser Val Thr Asn Pro Phe Gln Pro Ala Pro Ala Thr Leu Thr
        515                 520                 525

Leu Asn Gln Leu Arg Leu Ser Pro Val Pro Val Pro Gly Ala Pro
    530                 535                 540

Pro Thr Tyr Ile Ser Pro Leu Gly Gly Gly Pro Gly Leu Pro Pro Met
545                 550                 555                 560

Met Pro Pro Gly Pro Pro Ala Pro Asn Thr Asn Pro Phe Leu Leu
                565                 570                 575
```

-continued

```
<210> SEQ ID NO 255
<211> LENGTH: 900
<212> TYPE: PRT
<213> ORGANISM: Homo sapiens

<400> SEQUENCE: 255

Met Glu Pro Pro Leu Pro Val Gly Ala Gln Pro Leu Ala Thr Val Glu
1               5                   10                  15

Gly Met Glu Met Lys Gly Pro Leu Arg Glu Pro Cys Ala Leu Thr Leu
            20                  25                  30

Ala Gln Arg Asn Gly Gln Tyr Glu Leu Ile Ile Gln Leu His Glu Lys
        35                  40                  45

Glu Gln His Val Gln Asp Ile Ile Pro Ile Asn Ser His Phe Arg Cys
    50                  55                  60

Val Gln Glu Ala Glu Glu Thr Leu Leu Ile Asp Ile Ala Ser Asn Ser
65                  70                  75                  80

Gly Cys Lys Ile Arg Val Gln Gly Asp Trp Ile Arg Glu Arg Arg Phe
                85                  90                  95

Glu Ile Pro Asp Glu Glu His Cys Leu Lys Phe Leu Ser Ala Val Leu
            100                 105                 110

Ala Ala Gln Lys Ala Gln Ser Gln Leu Leu Val Pro Glu Gln Lys Asp
        115                 120                 125

Ser Ser Ser Trp Tyr Gln Lys Leu Asp Thr Lys Asp Lys Pro Ser Val
    130                 135                 140

Phe Ser Gly Leu Leu Gly Phe Glu Asp Asn Phe Ser Ser Met Asn Leu
145                 150                 155                 160

Asp Lys Lys Ile Asn Ser Gln Asn Gln Pro Thr Gly Ile His Arg Glu
                165                 170                 175

Pro Pro Pro Pro Pro Phe Ser Val Asn Lys Met Leu Pro Arg Glu Lys
            180                 185                 190

Glu Ala Ser Asn Lys Glu Gln Pro Lys Val Thr Asn Thr Met Arg Lys
        195                 200                 205

Leu Phe Val Pro Asn Thr Gln Ser Gly Gln Arg Glu Gly Leu Ile Lys
    210                 215                 220

His Ile Leu Ala Lys Arg Glu Lys Glu Tyr Val Asn Ile Gln Thr Phe
225                 230                 235                 240

Arg Phe Phe Val Gly Thr Trp Asn Val Asn Gly Gln Ser Pro Asp Ser
                245                 250                 255

Gly Leu Glu Pro Trp Leu Asn Cys Asp Pro Asn Pro Pro Asp Ile Tyr
            260                 265                 270

Cys Ile Gly Phe Gln Glu Leu Asp Leu Ser Thr Glu Ala Phe Phe Tyr
        275                 280                 285

Phe Glu Ser Val Lys Glu Gln Glu Trp Ser Met Ala Val Glu Arg Gly
    290                 295                 300

Leu His Ser Lys Ala Lys Tyr Lys Lys Val Gln Leu Val Arg Leu Val
305                 310                 315                 320

Gly Met Met Leu Leu Ile Phe Ala Arg Lys Asp Gln Cys Arg Tyr Ile
                325                 330                 335

Arg Asp Ile Ala Thr Glu Thr Val Gly Thr Gly Ile Met Gly Lys Met
            340                 345                 350

Gly Asn Lys Gly Gly Val Ala Val Arg Phe Val Phe His Asn Thr Thr
        355                 360                 365

Phe Cys Ile Val Asn Ser His Leu Ala Ala His Val Glu Asp Phe Glu
    370                 375                 380
```

-continued

```
Arg Arg Asn Gln Asp Tyr Lys Asp Ile Cys Ala Arg Met Ser Phe Val
385                 390                 395                 400

Val Pro Asn Gln Thr Leu Pro Gln Leu Asn Ile Met Lys His Glu Val
            405                 410                 415

Val Ile Trp Gly Asp Leu Asn Tyr Arg Leu Cys Met Pro Asp Ala Asn
            420                 425                 430

Glu Val Lys Ser Leu Ile Asn Lys Lys Asp Leu Gln Arg Leu Leu Lys
            435                 440                 445

Phe Asp Gln Leu Asn Ile Gln Arg Thr Gln Lys Lys Ala Phe Val Asp
450                 455                 460

Phe Asn Glu Gly Glu Ile Lys Phe Ile Pro Thr Tyr Lys Tyr Asp Ser
465                 470                 475                 480

Lys Thr Asp Arg Trp Asp Ser Ser Gly Lys Cys Arg Val Pro Ala Trp
                485                 490                 495

Cys Asp Arg Ile Leu Trp Arg Gly Thr Asn Val Asn Gln Leu Asn Tyr
            500                 505                 510

Arg Ser His Met Glu Leu Lys Thr Ser Asp His Lys Pro Val Ser Ala
            515                 520                 525

Leu Phe His Ile Gly Val Lys Val Val Asp Glu Arg Arg Tyr Arg Lys
            530                 535                 540

Val Phe Glu Asp Ser Val Arg Ile Met Asp Arg Met Glu Asn Asp Phe
545                 550                 555                 560

Leu Pro Ser Leu Glu Leu Ser Arg Arg Glu Phe Val Phe Glu Asn Val
                565                 570                 575

Lys Phe Arg Gln Leu Gln Lys Glu Lys Phe Gln Ile Ser Asn Asn Gly
            580                 585                 590

Gln Val Pro Cys His Phe Ser Phe Ile Pro Lys Leu Asn Asp Ser Gln
            595                 600                 605

Tyr Cys Lys Pro Trp Leu Arg Ala Glu Pro Phe Glu Gly Tyr Leu Glu
610                 615                 620

Pro Asn Glu Thr Val Asp Ile Ser Leu Asp Val Tyr Val Ser Lys Asp
625                 630                 635                 640

Ser Val Thr Ile Leu Asn Ser Gly Glu Asp Lys Ile Glu Asp Ile Leu
                645                 650                 655

Val Leu His Leu Asp Arg Gly Lys Asp Tyr Phe Leu Thr Ile Ser Gly
            660                 665                 670

Asn Tyr Leu Pro Ser Cys Phe Gly Thr Ser Leu Glu Ala Leu Cys Arg
            675                 680                 685

Met Lys Arg Pro Ile Arg Glu Val Pro Val Thr Lys Leu Ile Asp Leu
690                 695                 700

Glu Glu Asp Ser Phe Leu Glu Lys Glu Lys Ser Leu Leu Gln Met Val
705                 710                 715                 720

Pro Leu Asp Glu Gly Ala Ser Glu Arg Pro Leu Gln Val Pro Lys Glu
                725                 730                 735

Ile Trp Leu Leu Val Asp His Leu Phe Lys Tyr Ala Cys His Gln Glu
            740                 745                 750

Asp Leu Phe Gln Thr Pro Gly Met Gln Glu Glu Leu Gln Gln Ile Ile
            755                 760                 765

Asp Cys Leu Asp Thr Ser Ile Pro Glu Thr Ile Pro Gly Ser Asn His
770                 775                 780

Ser Val Ala Glu Ala Leu Leu Ile Phe Leu Glu Ala Leu Pro Glu Pro
785                 790                 795                 800
```

```
Val Ile Cys Tyr Glu Leu Tyr Gln Arg Cys Leu Asp Ser Ala Tyr Asp
                805                 810                 815

Pro Arg Ile Cys Arg Gln Val Ile Ser Gln Leu Pro Arg Cys His Arg
            820                 825                 830

Asn Val Phe Arg Tyr Leu Met Ala Phe Leu Arg Glu Leu Leu Lys Phe
        835                 840                 845

Ser Glu Tyr Asn Ser Val Asn Ala Asn Met Ile Ala Thr Leu Phe Thr
    850                 855                 860

Ser Leu Leu Leu Arg Pro Pro Asn Leu Met Ala Arg Gln Thr Pro
865                 870                 875                 880

Ser Asp Arg Gln Arg Ala Ile Gln Phe Leu Gly Phe Leu Leu Gly
                885                 890                 895

Ser Glu Glu Asp
            900

<210> SEQ ID NO 256
<211> LENGTH: 1621
<212> TYPE: PRT
<213> ORGANISM: Blackcurrant reversion virus

<400> SEQUENCE: 256

Met Ser Glu Ser Gly Asn Thr Thr Ser Met Pro Gly Cys Gly Arg Met
1               5                   10                  15

Cys Ala Leu Arg Ser Thr Trp Ser Lys Arg Ala Phe Leu Val Ala Cys
            20                  25                  30

Lys Asp Gly Ala Leu Thr Ser Asp Gly Arg Cys Pro Gln Tyr Gly Cys
        35                  40                  45

Gly Ala Leu Val Ser Ile Thr Lys Gly Val Gln Gln Pro Lys Lys Thr
    50                  55                  60

Ala Ser Ala Lys Val Val Lys Cys Leu Cys Trp Val Gln Pro Ala Arg
65                  70                  75                  80

Trp Cys Glu Lys His Ser Lys Gly Pro Ala Ser Pro Asn Gly Ser Val
                85                  90                  95

Thr Thr Lys Arg Ser Asn Ser Ala Arg Ala Ala Pro Ala Pro Leu Pro
            100                 105                 110

Tyr Lys Lys Gln Thr Cys Asp Val Val Thr Val Gly Pro Leu Glu
        115                 120                 125

Leu Val Tyr Pro Ala Leu Val Ser Glu Glu Leu Pro Thr Pro Val Ala
    130                 135                 140

Ala Thr Pro Thr Lys Val Glu Glu Val Pro Ile Pro Glu Leu Pro Leu
145                 150                 155                 160

Trp Leu Ala Pro Ala Trp Met Val Glu Gln Pro Tyr Ala Ala Thr Pro
                165                 170                 175

Glu Val Leu Cys Leu Thr Gln Arg Glu Glu Phe Ala Leu Leu Lys Lys
            180                 185                 190

Arg Leu Thr Arg Lys Gly Lys Leu Leu Gln Arg Arg Ala Thr His Ala
        195                 200                 205

Arg Phe Glu Ala Arg Ala Ala Leu Ala Arg Val Arg Ala Ala Thr Gln
    210                 215                 220

Arg Lys Val Glu Glu Val Thr Ala Leu Val Ile Lys Gly Arg Arg Ile
225                 230                 235                 240

Leu Ala Ala His Gln Leu Leu Arg Glu Leu Glu Val Ala Pro Leu
                245                 250                 255

Ser Gln Ala Gln Glu Gln Leu Val Ala Ser Ser Cys Ala Ala Ala
            260                 265                 270
```

```
Ala Arg Gln Glu Glu Cys Ala Ser Phe Leu Arg Arg Ala Lys Ala Trp
        275                 280                 285

Arg Lys Ser Ile Ser Ala Thr Pro Pro Val Ala Ala Thr Ala Val Ala
        290                 295                 300

Ser Lys Val Val Ser Ala Thr Met Pro Trp Ala His Leu Gly Leu Ser
305                 310                 315                 320

Leu Gly Gly Leu Leu Ala Val Pro Thr Leu Asp Gly Thr Leu Gly Ala
                325                 330                 335

Lys Gln Trp Asn Ala Lys Thr Ile Ala Thr Trp Val Leu Lys Pro Val
                340                 345                 350

Val Ser Cys Val Gln Ser Val His Ala Lys Val Arg Asp Trp Leu His
        355                 360                 365

Ser Gln Pro Glu Val Gly Val Thr Asn Thr Lys Val Pro Leu Val Leu
        370                 375                 380

Pro Glu Val Cys Leu Gly Val Leu Ser Pro Ser Leu Ser Glu Glu
385                 390                 395                 400

Ile Val Asp Asn Pro Gln Glu Thr Ser Gln Ser Gly Ile Trp His Pro
                405                 410                 415

Glu Met Gly Val Arg Asn Ile Tyr Val Phe His Asp Ser Trp Glu
                420                 425                 430

Thr Ser Pro Glu Glu Asp Glu Asn Tyr Thr Tyr Thr Phe Ser Arg Gln
        435                 440                 445

Cys Gly Ile Pro Tyr Leu Leu Val Glu Gly Arg Gly Ala Glu Glu Arg
        450                 455                 460

Lys Asn Thr Ile Leu Gly Trp Asp Phe Ser Leu His Asn Asp Gly Phe
465                 470                 475                 480

Glu Phe Leu Pro Ser Pro Glu Glu Gly Tyr Thr Lys Glu Leu Val Thr
                485                 490                 495

Pro Val Ala Leu Glu Glu Asp Lys Tyr Ser Thr Ala Ser Ser Cys
        500                 505                 510

Gly Phe Phe Ser Leu Asp Asp Val Ser Ser Ala Ile Thr Ile Gln Cys
        515                 520                 525

Pro Gly Leu Leu Ser Ala Asp Ala Asp Val His Phe Phe Asp Gly Pro
530                 535                 540

Gly Tyr Arg Cys Ser Ser Arg Pro Arg Asp Phe Arg Pro Pro Val Val
545                 550                 555                 560

Arg Gly Cys Asp Tyr Glu Ser Arg Val Lys Ala Ser Ile Gln Arg Lys
                565                 570                 575

Ile Glu Asn Pro Leu Gln Glu Arg Phe Ile Thr Val Leu Arg Glu Lys
                580                 585                 590

Arg Lys Lys Asn Lys Lys Glu Phe His Ser Phe Ser Ala Cys Phe
        595                 600                 605

Ala Phe Lys Arg Lys Gln Ile Gln Trp Pro Thr Pro Asn Glu Met
        610                 615                 620

Val Asn Glu Trp Glu Glu Tyr Cys Ile Ala Gln Ala Trp Leu Pro Phe
625                 630                 635                 640

Glu Val Val Thr Asp Glu Ile Glu Asp Val Thr Pro Leu Tyr Pro
                645                 650                 655

Gly Gly Arg Asp Tyr Asn Cys Asn Ser Gln Leu Leu Phe Pro Leu Ala
                660                 665                 670

Pro Leu Ser Thr Val Tyr Cys Asp Asp Ser Cys Phe His Pro Asn Asp
                675                 680                 685
```

-continued

```
Gly Trp Thr Thr Asp Gly Asn Gly Lys His Phe Arg Leu Ser Pro Gln
    690                 695                 700
Phe Val Leu Pro Asp Val Pro Ile Pro Ile Val His Arg Val Thr Arg
705                 710                 715                 720
Gln Leu Pro Gln Phe Leu Tyr Asp Leu Gly Ile Gly Asp Leu Thr Cys
                725                 730                 735
Asn Ser Gly Tyr Gln Ala Glu Asn Leu Gln Glu Glu Ile Gln Glu Arg
                740                 745                 750
Met Glu Asp Arg Ser Glu Glu Lys Pro Val Pro Ser Leu Asp Thr Leu
            755                 760                 765
Ile Ser Lys Leu Ser Lys Arg Ser Thr Lys Val Lys Gly Ala Gly Glu
770                 775                 780
Asn Arg Tyr Ala Asp Arg His Ser Leu Thr Glu Lys Ala Ile Phe His
785                 790                 795                 800
Gln Pro Gly Ala Leu Ser Arg Met Arg Ser Gly Lys Glu Lys Thr Ile
                805                 810                 815
Val Ala Ala Asn His Asn Ser Asp Gln Ile Ser Val Arg Met Ala Glu
                820                 825                 830
Cys Gly Lys Pro Val Phe Thr Pro Leu Pro Arg Met Ser Asp Glu Met
            835                 840                 845
Leu Arg Lys Phe Leu Glu Lys Gly Leu Gly Ser Thr Ser Thr Val Ala
850                 855                 860
Leu Asp Ile Gly Ile Gln Ser His Ile Pro Gln Gly Met Pro Thr Val
865                 870                 875                 880
Ala Phe Val Asn Val Met Asp Thr Arg Ile Glu Asp Pro Leu Tyr Ser
                885                 890                 895
Ser Leu Cys Gly Ser Tyr Ile Asp Leu Gly Arg Asp Arg Ala Lys Thr
                900                 905                 910
Leu Cys Leu Pro Leu Val Asn Phe Pro Met Ser Lys Leu Ala Glu Asp
            915                 920                 925
Val Asp Asp Val Leu Asn Gly Leu Met Leu Cys Thr His Phe Gln Asp
930                 935                 940
Ser Thr Lys Phe Gly Val Gly Lys Pro Ala Phe Gln Tyr Gly Thr Leu
945                 950                 955                 960
Glu Phe Gln Glu Phe Lys Pro Ser Ala Tyr Ser Asp Phe Ser Arg Val
                965                 970                 975
Arg Asp Asn Trp Asp Ala Ile Ala Lys Gln Gln Asn Thr Pro Asn Asp
                980                 985                 990
Arg Ile Leu Ala Gly Phe Ser Val Leu Gly Ala Val Ser Gln Ala Tyr
            995                 1000                1005
Asn Gln Ala Leu Pro Val Phe Lys Ser Val Glu Leu Val Ala Pro Pro
    1010                1015                1020
Lys Arg Lys Pro Val Val Ala Thr Phe Gln Asn Pro Thr Thr Leu Gly
1025                1030                1035                1040
Arg Ser Asn Thr Thr Arg Ser Phe Arg Met Pro Thr Met Asp Leu Pro
                1045                1050                1055
Arg Ser Thr Gly Arg Asp Ala Pro Ile Pro Ile Val His Arg Arg Asn
                1060                1065                1070
Asn Asn Asp Val His Phe Asp Glu Ala Thr Pro Ala Arg Phe Ser Thr
            1075                1080                1085
Cys Asp Ser Gly Leu Val Ala Asp Thr Thr Leu Ala Phe Ala Lys Met
    1090                1095                1100
Tyr Gln Cys Lys Lys Asp Ala Lys Ala Gly His Val Leu Ala Thr Ile
```

```
              1105                1110                1115                1120
Asp Ile Gln Glu Cys Val Phe Glu Asp Asn Arg Arg Val Ala Leu Asp
              1125                1130                1135
Trp Leu Ala His Gly Leu Ala Ser Phe Lys Tyr Asp Leu Gln Leu Thr
              1140                1145                1150
Val Asp Ser Asn Pro Phe Val Gly Val Thr Leu Gly Ile Thr Val Asp
              1155                1160                1165
Ala Phe Asp Arg Leu Leu Pro Gln Ile Ser Asp Glu Val Ile Ala Val
              1170                1175                1180
Pro Leu Ala Phe Gln Leu Pro Thr Tyr Leu Phe Pro Ile Ser Lys Lys
1185                1190                1195                1200
Gly Thr Phe Thr Gln Thr Ile Asp Phe Ala Ala Ile Ala Gly Tyr Asn
              1205                1210                1215
Phe Phe Pro His Val Ala Ala Phe Gly Arg Pro Lys Ile Ile Val Tyr
              1220                1225                1230
Ile Val Ser Asp Asn Asp Leu Pro Ala Ser Asp Thr Trp Met Cys Leu
              1235                1240                1245
Val Glu Leu His Met Thr Arg Leu Glu Ser Ser Thr Leu Ala Cys Ser
              1250                1255                1260
Pro Thr Leu Val Leu Pro Gln Ala Phe Gly Gly Asp Leu Pro Leu Asp
1265                1270                1275                1280
Leu Trp Arg Gly Pro Tyr Thr Phe Pro Leu Gly Gly Thr Lys Arg
              1285                1290                1295
Leu Ser Thr Ser Leu Asp Ile Gly Thr Ser Thr Thr Val Ser Gly
              1300                1305                1310
Trp Arg Thr Val Ser Pro Ala Ala Tyr Ala Leu Phe Leu Gln Gly His
              1315                1320                1325
Gly Gly Ser Leu Val Gly Glu Val Val His Thr Gly Ser Ala Ala Val
              1330                1335                1340
Ser Cys Ala Leu His Leu Cys Ile Ser Phe Gly Gly Ala Pro Pro Thr
1345                1350                1355                1360
Leu Glu Glu Ala Leu Val Phe Pro Gly Phe Arg Leu Pro Ser Gly Glu
              1365                1370                1375
Gly Lys Phe His Ile Lys Val Gln Thr Pro Tyr Gly Arg Leu Ser Thr
              1380                1385                1390
Leu Thr Pro Asp Cys Ala Leu Tyr Val Tyr Leu Ala Gly Gly Pro Ile
              1395                1400                1405
Ala Val Ala Pro Met Ser Val Pro Tyr Gln Phe Cys Ile His Leu Glu
              1410                1415                1420
Arg Leu Val Asp Asp Gly Ala Pro Pro Arg Thr Ile Gly Leu Ile Arg
1425                1430                1435                1440
Glu Phe Asn Trp Ala Thr Ile Asn Asn Phe Lys Ser Asp Asp Ile Thr
              1445                1450                1455
Phe Ala Ile Pro Ala Arg Leu Ser Asp Leu Val Leu Thr Cys Gly Asp
              1460                1465                1470
Val Thr Met Ser Thr Asn Pro Leu Ala Leu Leu Ile Gly Ser Cys Gly
              1475                1480                1485
Phe Phe Arg Gly Asn Leu Thr Val Val Leu Glu Trp Ala Thr Phe Leu
              1490                1495                1500
Lys Ala Gly Asp Lys Glu Gly Thr Val Gln Leu Thr Thr Cys Arg Gly
1505                1510                1515                1520
Met Ile Asn Asn Val Lys Gly Val Arg Asn Ala Ile Gln Lys Lys Val
              1525                1530                1535
```

```
Val Asn Leu Ser Leu Val Gly Ser Val Ser Arg Tyr Leu Asn Val Gly
        1540                1545                1550

Asp Phe Thr Gly Phe Ala Gln Ser Gly Gly Gln Val Gly Tyr Asp Glu
    1555                1560                1565

Ile Phe Leu Glu Phe Ser Thr Asn Lys Ala Lys Gln Ile Arg Tyr Leu
1570                1575                1580

Asn Ile Asn Val Glu Leu Asp Glu Asn Phe Glu Leu Tyr Gly Arg Thr
1585                1590                1595                1600

Ile Ile Pro Leu Lys Asn Thr Ala Pro Ala Phe Ala Ser Thr Ser Ser
            1605                1610                1615

Ala Pro Asn Glu Ser
        1620

<210> SEQ ID NO 257
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Lys Phe Leu Pro Ser
1               5

<210> SEQ ID NO 258
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Phe Leu Pro Ser Ile
1               5

<210> SEQ ID NO 259
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Arg Phe Leu Pro Ser
1               5

<210> SEQ ID NO 260
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Phe Leu Pro Ser Glu
1               5
```